United States Patent [19]

Moon et al.

[11] Patent Number: 5,273,975
[45] Date of Patent: Dec. 28, 1993

[54] HETEROCYCLIC AMINES HAVING CENTRAL NERVOUS SYSTEM ACTIVITY

[75] Inventors: Malcolm W. Moon; Richard F. Heier; Jeanette K. Morris, all of Kalamazoo, Mich.

[73] Assignee: The Upjohn Company, Kalamazoo, Mich.

[21] Appl. No.: 778,204

[22] PCT Filed: May 15, 1990

[86] PCT No.: PCT/US90/02621

§ 371 Date: Dec. 6, 1991

§ 102(e) Date: Dec. 6, 1991

Related U.S. Application Data

[63] Continuation-in-part of Ser. No. 364,374, Jun. 9, 1989, abandoned.

[51] Int. Cl.$^5$ .................. A61K 31/495; A61K 31/50; C07D 513/02; C07D 471/06
[52] U.S. Cl. .................. 514/233.2; 514/253; 514/291; 514/292; 514/293; 514/294; 544/126; 544/361; 546/80; 546/82; 546/83; 546/84; 546/89; 546/94
[58] Field of Search .................. 546/82, 83, 84, 89, 546/94, 80; 544/126, 361; 514/291, 292, 293, 294, 233.2, 253

[56] References Cited

U.S. PATENT DOCUMENTS

| | | | |
|---|---|---|---|
| 4,110,339 | 8/1978 | Bach et al. | 548/436 |
| 4,550,114 | 10/1985 | White | 514/294 |
| 4,808,619 | 2/1989 | Evans et al. | 514/278 |
| 4,952,584 | 8/1990 | Thompson et al. | 514/292 |
| 5,021,438 | 6/1991 | Jange et al. | 514/373 |
| 5,112,830 | 5/1992 | Shutske et al. | 514/291 |

FOREIGN PATENT DOCUMENTS

| | | |
|---|---|---|
| 0153083 | 8/1988 | European Pat. Off. |
| 3346573A | 4/1985 | Fed. Rep. of Germany |
| WO87/04153 | 7/1987 | PCT Int'l Appl. |
| WO88/04292 | 6/1988 | PCT Int'l Appl. |

OTHER PUBLICATIONS

Evans, D. D. et al., "1,3,4,5-Tetrahydrobenz[cd]indoles and Related Compounds. Part V. Some Reactions of 1,2,4,5-Tetrahydropyrrolo[3,2,1-ij]quinolin-6-one", J. S. C. Perkin I, 285-88 (1974).
K. Sempuku, "Tetracyclic Compounds", Chemical Abstract 95:62240y, 1981.

*Primary Examiner*—Mukund J. Shah
*Assistant Examiner*—Matthew V. Grumbling
*Attorney, Agent, or Firm*—Donald L. Corneglio

[57] ABSTRACT

Tricyclic nitrogen containing compounds, having central nervous system activity of the following structural formula:

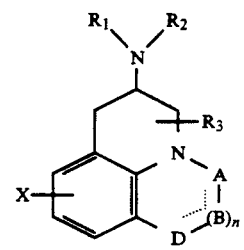

and pharmaceutically acceptable salts thereof wherein $R_1$, $R_2$, and $R_3$ are independently hydrogen, $C_{1-6}$ alkyl, alkenyl, or alkynyl, $C_{3-10}$ cycloalkyl, or $R_1$ and $R_2$ are joined to form a $C_{3-7}$ cyclic amine which can contain additional heteroatoms; X is hydrogen, $C_{1-6}$ alkyl halogen, hydroxy, alkoxy, cyano, carboxamide, carboxyl, or carboalkoxyl; A is $SO_2$, N, CH, $CH_2$, $CHCH_3$, C=O, C=S, C-$SCH_3$, C=NH, C-$NH_2$, C-$NHCH_3$, C—NHCOOCH$_3$, or C—NHCN. B is $CH_2$, CH, C=O, N, NH or N—$CH_3$; n is 0 or 1; and D is CH, $CH_2$, C=O, O, N, NH or N—$CH_3$. These new compounds are suitable for treating schizophrenia, Parkinson's disease, anxiety, depression or as compounds for lowering blood pressure in animal or human hosts.

11 Claims, No Drawings

HETEROCYCLIC AMINES HAVING CENTRAL NERVOUS SYSTEM ACTIVITY

CROSS-REFERENCE TO RELATED APPLICATIONS

This application is the national phase of international application PCT/US90/02621, filed May 15, 1990, which is the continuation-in-part of U.S. Ser. No. 07/364,374, filed Jun. 9, 1989, abandoned.

BACKGROUND OF THE INVENTION

The present invention is directed toward tricyclic nitrogen containing compounds, heterocyclic amines, having central nervous system activity. These new compounds are suitable for treating schizophrenia, Parkinson's disease, anxiety or as compounds for lowering blood pressure.

A series of dihydrophenalenes, tricyclic amine substituted compounds, and related compounds having central nervous system activity were described in PCT Int. Pub. No. WO87/04153 and in PCT Int. Pub. No. WO88/04292. A major difference between those compounds and the present invention is that the subject compounds have at least one nitrogen atom in the tricyclic ring structure which is shared by two of the ring structures. Generally, the subject compounds have exhibited antipsychotic acitivity and better oral bioavailability.

Information Disclosure Statement

PCT Int. Pub. No. WO87/04153 and PCT Int. Pub. No. WO88/04292 each describe tricyclic structures having central nervous system activity.

U.S. Pat. No. 4,110,339 discloses 4-(di-n-propyl-)amino-1,3,4,5-tetrahydrobenz(cd)indole compounds useful as prolactin inhibitors and in the treatment of Parkinsonism. European Patent Application 153,083 and German Patent No. 3,346,573 disclose methoxy substituted 4-(di-n-propyl)amino-1,3,4,5-tetrahydrobenz(cd)indole compounds. These publications disclose nitrogen containing tricyclic ring structures but the nitrogen is not shared by any of the rings.

Evans, D. D., Peters, D. J., J. Chem. Soc., Perkin Trans. 1, pp 285-288 (1974) discloses nitrogen containing tricyclic ring structures where the nitrogen is shared by two ring structures but additionally includes other substituents not common to the subject compounds.

SUMMARY OF THE INVENTION

In the aspect, the present invention is directed toward tricyclic nitrogen containing compounds of Formula I, having central nervous system activity and pharmaceutically acceptable salts. $R_1$, $R_2$, and $R_3$ are independently hydrogen, $C_{1-6}$ alkyl, $C_{3-5}$ alkenyl, or $C_{3-5}$ alkynyl, $C_{3-7}$ cycloalkyl or $C_{4-10}$ cycloalkyl- or phenyl-substituted alkyl, or $R_1$ and $R_2$ are joined to form a $C_{3-7}$ cyclic amine which can contain additional heteroatoms and/or unsaturation. X is hydrogen, $C_{1-6}$ alkyl, halogen, hydroxy, alkoxy, cyano, carboxamide, carboxyl, or carboalkoxyl. A is $SO_2$, N, CH, $CH_2$, $CHCH_3$, C=O, C=S, C—$SCH_3$, C=NH, C—$NH_2$, C—$NHCH_3$, C—$NHCOOCH_3$, or C—NHCN. B is $CH_2$, CH, C=O, N, NH or N—$CH_3$ and n is 0 or 1. D is $CH_2$, C=O, O, N, NH or N—$CH_3$. These new compounds are suitable for treating schizophrenia, Parkinson's disease, anxiety, depression, or as compounds for lowering blood pressure.

In another aspect, the invention is a novel compound of the structural formula XXXV' where W is O or $H_2$ and $R_1'$ and $R_2$ are independently hydrogen or a $C_{1-4}$ alkyl group. This compound is useful as an intermediate in the preparation of compounds of Formula I. Preferred compounds are where W is $H_2$ and $R_1$ and $R_2$ are the same such as $CH_3$ or $C_3H_2$ groups.

In yet another aspect, the present invention is a method for treating central nervous system (CNS) disorders such as anxiety, depression, hypertension and associated high blood pressure, Parkinson's disease and schizophrenia in animal or human hosts by administering a pharmaceutically effective amount of a commond of Formula I including pharmaceutically acceptable salts. Other uses for these compounds include panic attacks, eating disorders, obsessive-compulsive disturbances seen in demantia disorders. In addition, central 5-HT receptor activation are believed to be involved in mediating sexual behavior. These compounds would be useful to stimulate sexual activity and to alleviate impotence.

DETAILED DESCRIPTION OF THE INVENTION

The present invention describes compounds having central nervous system activity. The compounds are identified by a tricyclic ring structure having a nitrogen atom shared by two rings to which an amina substituent ($NR_1R_2$) is attached as structurally depicted by Formula I on the Formula Sheet, below. Generally, these structures include a variety of fused tricyclic organic compounds; structures are shown in the Formula sheets. The systematic names for the ring systems in these compounds may be found by consulting the Ring Systems Handbook, 1988 edition, published by Chemical Abstracts Service. These names are derived by combining the names of benzene or a monocyclic heterocycle with the name of a bicyclic heterocycle to which it is fused. The atoms and bonds common to the fused rings are then specified to distinguish it from isomeric systems with similar names.

Included in the invention are the 5-aminoimidazo-(4,5,1-ij)quinolines and 5-aminoimidazo(4,5-ij)quinolinones of Structure I (compounds 6-71), compounds more simply referred to as imidazoquinolines are imidazoquinolinones or 5-aminoimidazoquinolines and 5-aminoimidazoquinolinones. These particular compounds have been found to be active in various central nervous system screens such as hypothermia and hypoxic stress tests and have been found to be dopamine and serotonin such as, $5HT_{1A}$ receptor binding assay antagonists.

The subject compounds are typically represented by Formula I wherein $R_1$, $R_2$ and $R_3$ are independently hydrogen, $C_{1-6}$ alkyl, $C_{3-5}$ alkenyl, $C_{3-5}$ alkynyl, $C_{3-7}$ cycloalkyl, or $C_{4-C_{10}}$ cycloalkyl- or phenyl-substituted alkyl, or $R_1$ and $R_2$ are joined to form a $C_{3-7}$ cyclic amine which can contain additional heteroatoms and/or unsaturation; X is hydrogen, $C_{1-6}$ alkyl, halogen, hydroxy, alkoxy, cyano, carboxamide, carboxyl, or carboalkoxyl; n is 0 or 1; and A is $SO_2$, N, CH, $CH_2$, CH-halogen, $CHCH_3$, C=O, C=S, C—$SCH_3$, C=NH, C—$NH_2$, C—$NHCH_3$, C—$NHCOOCH_3$, or C—NHCN; B is $CH_2$, CH, CH-halogen, O, C=O, N, NH or N—$CH_3$; n is 0 or 1; and D is CH, $CH_2$, CH-halogen, C=O, O, N, NH or N—$CH_3$.

Examples of "$C_1$-$C_6$ alkyl" are methyl, ethyl, propyl, butyl, pentyl and hexyl and isomeric forms thereof.

Examples of "alkenyl" groups are $C_{3-5}$ straight or branched unsaturated hydrocarbons having at least one double bond such as propenyl or butenyl.

Examples of "alkynyl" groups are $C_{3-5}$ straight or branched unsaturated hydrocarbons having at least one triple bond such as propynyl or butynyl.

Examples of "$C_{3-7}$ cycloalkyl" are cyclopropyl, cyclobutyl, cyclopentyl, cyclohexyl, or cycloheptyl. Examples of cycloalkyl-substituted alkyl include (cyclopropyl)methyl, or (cyclobutyl)methyl. Examples of phenyl-substituted alkyl include phenylmethyl (benzyl), 1-(phenyl)ethyl or 2-(phenyl)ethyl, or 4-phenyl)butyl.

"$C_{3-7}$ cyclic amine" means where the $R_1$ and $R_2$ groups are joined to form a ring including the attached nitrogen atom, examples azetidine, pyrrolidine, piperidine, 2-methylpyrrolidine. This ring may also contain additional "hetero atoms" which are nitrogen, oxygen or sulfur and/or unsaturation, eg piperazine, N-methylpiperazine, morpholine, imidazole.

"Halogen" is defined as being any of F, Cl, Br or I.

"Akoxy" is defined as a $C_{1-6}$ alkyl group attached to an oxygen atom, such as methoxy, ethoxy, isopropoxy.

"Carboxamide" is defined as the group —$CONH_2$.

"Carbozlkoxyl" is defined as the group —COOR, where R is lower alkyl, such as carbomethoxy, carboethoxy.

"Thiocarbonyl" is defined as the group C=S, that is a carbonyl group in which the oxygen atom is replaced by sulfur.

"Sulfonyl" is defined as $SO_2$ in which the sulfur atom is attached to the adjacent ring atom groups.

"Pharmaceutically acceptable salts" are hydrochloride, hydrobromide, hydroiodide, sulfate, phosphate, acetate, propionate, lactate, maleate, malate, succinate, tartrate, cyclohexanesulfamates, methanesulfonates, ethanesulfonates, benzenesulfonates, toluenesulfonates and other pharmaceutically acceptable counter ions for amines. Additionally, the compounds of this invention may be administered in a suitable hydrated form.

The compounds of Formula I may be prepared from methyl-substituted heterocycles of Formula II and substituted 3-aminotetrahydroquinolines of Formula III following the general procedures described in Schemes 1-7. Schemes and Formulas are shown below.

In Formula II, m is 0 or 1; when m is O then a double bond joins N to A. In Formula III, W is O or $H_2$ and D' may be nitro, amino, hydroxy or alkoxy; the remaining groups in Formulas II and III are as defined for I.

Some of the methyl substituted heterocycle intermediates required for the work are described in the chemical literature as indicated. Literature procedures for the syntheses of 3-aminotetrahydroquinolines have been reported and can be used to build the 8-substituted compounds of Structure III required in this work; the compounds of Structure III where D' is nitro, amino, hydroxy or alkoxy are new compounds.

For the preparation of compounds III and for the conversion of compounds II to I, malonate intermediates of Formula VI and VII are required. For the preparation of these compounds a malonic acid diester IV, preferably th edimethyl, diethyl or methyl benzyl diester, is reacted with bromine in carbon tetrachloride to afford the bromomalonic acid diester V. This is reacted with the appropriate amine in a suitable solvent such as methylene chloride, ether, or tetrahydrofuran. After separating the amine hydrochloride by-product and removing any excess amine, the substituted aminomalonate of Formula VI may be used without further purification, or may be purified by chromatography before further use. Amines which have been used in this reaction include dimethylamine, pyrrolidine, piperidine, morpholine, imidazole, 4-methylpiperazine, propylamine, and (R)— and (S)—α-methylbenzylamine to give the intermediates VI listed in Table I. The mixed esters of Table 1 (compounds VIi through VIq) are particularly useful, as the carbobenzyloxy group can be removed by catalytic hydrogenation. Intermediates VId-h give tertiary amine products which can be debenzylated by catalytic hydrogenation to the corresponding secondary amine derivatives.

TABLE 1

| Structures of Aminomalonates of Formula VI | | | |
|---|---|---|---|
| Compound | Amine | R' | R" |
| VIa | dimethylamine | ethyl | ethyl |
| VIb | dipropylamine | ethyl | ethyl |
| VIc | propylamine | ethyl | ethyl |
| VId | (phenylmethyl)methylamine | ethyl | ethyl |
| VIe | (phenylmethyl)propylamine | ethyl | ethyl |
| VIf | benzylamine | ethyl | ethyl |
| VIg | α-(1-phenylethyl)amine | ethyl | ethyl |
| VIh | (R)-α-(1-phenylethyl)amine | ethyl | ethyl |
| VIi | dimethylamine | methyl | benzyl |
| VIj | dipropylamine | methyl | benzyl |
| VIk | pyrrolidine | methyl | benzyl |
| VIm | piperidine | methyl | benzyl |
| VIn | morpholine | methyl | benzyl |
| VIp | imidazole | methyl | benzyl |
| VIq | 4-methylpiperazine | methyl | benzyl |

When a primary amine is reacted with a compound of Formula V, the initally formed product VI may be reacted with an acyl chloride, an alkyl- or benzylchloroformate, or with di t-butyl dicarbonate to give the amindes and carbamates of Formula VII. In formula VII, $R_1'$ is hydrogen, alkyl, alkoxycarbonyl, or benzyloxycarbonyl; compounds VIIe-VIIf (Table 2) have been prepared in this way from compound VIc.

Other aminomalonates of Formula VII may be prepared form dialkyl aminomalonates such as diethyl aminomalonate VIII. Compound VIII reacts with di t-butyl dicarbonate to give carbamate VIIc, a versatile intermediate in which the amine function is protected with the acid-labile t-butoxycarbonyl group. Reductive alkylation of VIII with propionaldehyde using sodium cyanoborohydride can be controlled so as to give secondary amine VIc or tertiary amine VIb as the major product. Compound VIc may be acylated with propionyl chloride to give VIIe or converted to the t-butoxycarbonyl derivative VIIf.

TABLE 2

| Formulas of Aminomalonates of Formula VII | | | | |
|---|---|---|---|---|
| Compound | $R_1'$ | $R_2$ | R' | R" |
| VIIa | H | H | ethyl | ethyl |
| VIIb | H | $CH_3$ | ethyl | ethyl |
| VIIc | $OC(CH_3)_3$ | H | ethyl | ethyl |
| VIId | $C_2H_5$ | H | ethyl | ethyl |
| VIIe | $C_2H_5$ | $C_3H_7$ | ethyl | ethyl |
| VIIf | $OC(CH_3)_3$ | $C_3H_7$ | ethyl | ethyl |

The 2,3,6,7-tetrahydro-1H,5H-benzo(ij)quinolizin-2-amines of the invention, compounds of Formula I where A, B, and D are $CH_2$ may be prepared as shown in Scheme 1 for the preparation of compounds 1-5.

Bromination of 8-methylquinoline (IX) with N-bromosuccinimide afforded 8-(bromomethyl)quinoline (X) which was reacted with diethyl (formylamino)malonate (VIIa) to give XIa ($R_1'=H$). This was hydrogenated using a platinum catalyst to give XIIa which was hydrolyzed to XIIIa. This was hydrolyzed to XIV, methylated to XV, and reduced to give compound 1. Compound XIIIa was also reduced with lithium aluminum hydride to give a mixture of compounds 2 and 3. The propylamino analogues, compounds 4 and 5, were prepared as outlined in Scheme 1 from 8-(bromomethyl)quinoline and diethyl (1-oxopropyl)malonate (VIId).

Analogues may be prepared by substituting aminomalonates VIi–VIq for VIIa and VIId in the above reaction sequence.

The 5,6-dihydro-N,N-dipropyl-4H-imidazo(4,5,1-ij)quinolin-5-amines of the invention, compounds of Formula I where D is nitrogen, A is CH, n is 0 and D and A are joined by a double bond, may be prepared as illustrated in Scheme 2 for the preparation of compound 6. Catalytic hydrogenation of 2-methyl-6-nitroaniline (XVI) using a palladium catalyst afforded 3-methyl-1,2-benzenediamine (XVIII) which was heated with formic acid to give 4-methylbenzimidazole (XVIII). This was heated in dioxane with di-t-butyl dicarbonate and the t-butyl 4-methylbenzimidazole-1-carboxylate (XIXa, R is $OC(CH_3)_3$) thus obtained was brominated with N-bromosuccinimide in carbon tetrachloride to give t-butyl 4-(bromomethyl)benzimidazole-1-carboxylate (XXa). Alkylation of XXa with the potassium salt of diethyl (dipropylamino)-malonate (VIb) in refluxing THF afforded XXIa which was hydrolyzed to XXII using sodium ethoxide in ethanol containing limited amounts of water. Compound XXII was reduced to the alcohol XXIII using lithium aluminum hydride. When XXIII was treated with carbon tetrabromide and triphenylphosphine in methylene chloride compound 6 was obtained directly.

Modifications may be made in this reaction sequence. The hydrolysis of XXIa to XXII may be carried out in two steps; under mild hydrolysis conditions, ethyl-α-(dipropylamino)-1H-benzimidazol-4-propanoate, formed by loss of the t-butoxycarbonyl group, can be obtained as the only reaction product, and this may be subsequently hydrolyzed to XXII. Compound XVIII was reacted with methyl chloroformate to give XIXb (R is $OCH_3$) which was converted to high yield to XXII as shown in Scheme 2. Acetylation of XVIII gave XIXc (R is $CH_3$) which was also converted to XXII, although the yield in this reaction was not as high as when the t-butoxycarbonyl or carbomethoxy protecting groups were used.

The reaction sequence of Scheme 2 may be used to prepare analogues in which the dipropylamine substituent is modified. Using the malonates VIi–VIq in place of diethyl (dipropylamino)malonate (VIb), compounds 7–12 were obtained. In the preparation of these compounds the adduct formed by reacting the malonate with XXa was converted to the methyl α-(substituted amino)-1H-benzimidazole-4-propanoate by hydrogenolysis as described in Example 19.

The sequence may also be used to prepare compounds of Formula I which have a substituent (X) in the benzene ring. For example, using the substituted benzimidazoles, 5-methoxy-4-methylbenzimidazole, 6-methoxy-4-methylbenzimidazole, 4-methoxy-6-methylbenzimidazole and 5-chloro-4-methylbenzimidazole in place of 4-methylbenzimidazole (XVIII), compounds 14–18 were obtained. Compounds 14–16 were treated with hydrobromic acid to give the corresponding phenols 19–21 respectively.

An alternate synthesis of 5,6-dihydro-N,N-dipropyl-4H-imidazo(4,5,1-ij)quinolin-5-amines from 3-aminoquinoline (XXIV) is shown in Scheme 3. Compound XXIV was formylated to give XXV and this was hydrogenated using platinum oxide as catalyst and formylated to give XXVI in good yield. Bromination of XXVI gave the 6-bromo compound XXVII which was nitrated to give XXVIII. Hydrogenation of XXXIX in presence of palladium charcoal gave the triamine XXX, which was treated with formic acid to give compound 22. The primary amine reacted with propionaldehyde and sodium cyanoborohydride to give the mono- and di-propylamine derivatives, compounds 23 and 6 respectively. Catalytic reduction of compound 22 in the presence of formaldehyde gave the previously described dimethylamine analogue (compound 7).

The sequence of Scheme 3 may also be used to prepare compounds of Formula I which have a substituent (X) in the benzene ring. For example, using 3-amino-6-methylquinoline in place of 3-aminoquinoline, compound 24 was obtained. The 3-amino-6-methylquinoline intermediate was prepared using literature procedures from p-toluidine and the sodium salt of nitromalonaldehyde. Other ring-substituted analogues can be prepared by this procedure.

The 5-amino-5,6-dihydro-4H-imidazo(4,5,1-ij)quinolin-2-ones of the invention, compounds where A is carbonyl, n is O, and D is NH or N-(lower alkyl) may be prepared as shown in Scheme 4. Nitroquinoline XXIX, prepared as outlined in Scheme 3, was protected, reduced, and cyclized using phosgene to give the t-butoxycarbonyl-protected imidazoquinolinone XXXIII. This was hydrolyzed to the amine (compound 26) which was alkylated to give the dimethylamino analogue compound 27 and propylamino analogues, compounds 28 and 29. Further alkylation of compounds 27 and 29 using potassium hydride/methyl iodide gave compounds 30 and 31 respectively.

6-Bromo-1,2,3,4-tetrahydro-3-quinolinamine (compound XXIX) was alkylated with propyl iodide to give XXIVa and this was reduced to-1,2,3,4-tetrahydro-$N^3,N^3$-dipropyl-3,8-quinolinediamine, Formula XXXVa where $R_1$ and $R_2$ are $C_3H_7$. Alkylation of XXIX with formaldehyde/formic acid following by catalytic reduction gave the corresponding dimethylamino compound Formula XXXVb where $R_1$ and $R_2$ are $CH_3$. Compound XXXVa has also been prepared from 2-nitrobenzylchloride in Example 67.

Intermediates XXXII, XXXVa and XXXVb may be used for the preparation of the 5-amino-5,6-dihydro-4H-imidazo(4,5,1-ij)quinolines and 5-amino-5,6-dihydro-4H-imidazo(4,5,1-ij)quinolin-2-ones of the invention and in the preparation of a variety of new heterocyclic analogues where the adjacent nitrogen atoms are joined to form a five or six membered heterocyclic ring as shown for compound XXXVa in Scheme 5. Compound XXXVa was reacted with thiophosgene or di-(2-pyridyl)thiocarbonate to give 5-(dipropylamino)-5,6-dihydro-4H-imidazo (4,5,1-ij)quinolin-2-thione (compound 33) which was further alkylated to 5,6-dihydro-2-methylthio-N,N-dipropyl-4H-imidazo(4,5,1-ij)quinoline-5-amine (compound 34). Compounds XXXVa reacted with cyanogen bromide to give compound 35 which was alkylated with methyl iodide to give compound 36. Compound XXXVa reacted with diphenyl cyanocarbonimidate to give compound 37 and with sulfamide to give compound 38.

Compound with a six-membered heterocyclic ring were prepared by reacting compound XXXVa with ethyl bromoacetate to give compound 39, chloroacetic anhydride to give compound 40, butyl glyoxylate to give compound 41, ethyl oxalyl chloride or oxalyl chloride to give compound 42, ethyl bromopropionate to give compound 84, and α-chloropropionyl chloride to give compound 85.

A similar series of compounds (compounds 43-50) were prepared from 1,2,3,4-tetrahydro-$N^3$,$N^3$-dimethyl-3,8-quinolinediamine; other products may be obtained by substituting compound XXXII in these reactions.

The 5-amino-5,6-dihydro-4H-imidazo(4,5,1-ij)quinolin-2-ones of the invention may also be prepared by the route shown in Scheme 6. 3-Methyl-1,2-benzenediamine is reacted with carbonyl diimidazole or phosgene to give 4-methylbenzimidazolone (XXXVI). This is refluxed with phosphorus oxychloride to give XXXVII which is protected and reacted with N-bromosuccinimine to give compound XXXIX. This is coupled with VIIb and the resulting adduct LX is hydrolyzed to LI. Reduction with lithium aluminum hydride alcohol LXII which was treated with carbon tetrabromide/triphenylphosphine to give compound 51. Compound 51 was refluxed in acetic acid to effect conversion to compound 6.

Analogues of compounds 51 and 6 may be prepared by the procedure of Scheme 6. By using malonates VIk-q or VIg in place of VIIc, compounds 52-57 were prepared.

The sequence may also be used to prepare compounds of Formula I which have a substituent (X) in the benzene ring. For example, using the substituted benzimidazoles 2,5-dichloro-4-methylbenzimidazole, 2-chloro-5-methoxy-4-methylbenzimidazole, 2-chloro-6-methoxy-4-methylbenzimidazole and 2-chloro-4-methoxy-6-methylbenzimidazole in place of 2-chloro-4-methylbenzimidazole (XVIII) compounds 58-63 were obtained; these compounds have also been prepared from the ring substituted 1,2,3,4-tetrahydro-3,8-quinolinediamines as described in Examples 82-87.

Compounds with a methyl substituent at position 6 in the imidazoquinoline or imidazoquinolinone ring were prepared from 4-ethylbenzimidazole by the procedure of Scheme 2 (see Example 88) and by converting 2-ethylaniline to 1,2,3,4-tetrahydro-4-methyl-$N^3$,$N^3$-dimethyl-3,8-quinolinediamine using the procedure of Scheme 7 and 4. Compounds with an alkyl substituent at position 4 in the imidazoquinoline or imidazoquinolinone ring were prepared from intermediate XXIII and related primary alcohols by oxidation to the aldehyde, reacting the aldehyde with an alkyl magnesium bromide, and cyclizing the resulting alcohol (see Example 92). Following these procedures, compounds 64-71 were obtained.

The 5-amino-5,6-dihydro-4H-oxazolo(5,4,1-ij)quinolin-2-ones of the invention, compounds where A is carbonyl, n is 0 and D is 0, may be prepared as outlined in Scheme 7 for the preparation of compound 72. 3-Methyl-2-nitroanisole (XLIII) was reduced to XLIV and this was refluxed with acetic anhydride to give XLV. This product was brominated and coupled with VIb to give XLVII. Compound XLVII was refluxed with sodium ethoxide in ethanol to give XLVIII which was converted to the phenol XLIX and reduced with lithium aluminum hydride to L. Compound L was treated with carbonyl diimidazole to give compound 72.

The related compounds 73-79 were prepared by the procedure of Scheme 7 from compound XLVI and the appropriate malonate of Formula VI or VII. Compounds 80 and 82 were prepared by reacting phenol intermediate L with thiophosgene or ethyl bromoacetate.

Compounds 86-93, were prepared from the 4-methyl heterocycle of Formula II by the procedures described in Schemes 2 and 6.

Compounds 95-97 were prepared from 5-(propylamino)-5,6-dihydro-4H-pyrrolo(3,2,1-ij)quinolin-2,3-dione (compound 94) which was prepared as described in Example 118.

6-(Dipropylamino)-2,3,6,7-tetrahydro-5H-pyrido(3,2,1-ij)quinazolin-3-one (compound 98) was prepared in nine steps from 3-methyl-2-nitrobenzoic acid as described in Example 122. Compounds 99-105 were prepared from the same starting material using the procedures described in Examples 123-129.

An alternative procedure for synthesizing the compounds of the invention is shown in Scheme 8. t-Butyl 1,2,3,4-Tetrahydro-5-(dipropylamino)quinoline-1-carboxylate prepared as described in Example 130 is converted to the anion LI which is further reacted as shown in Scheme 8 to yield compounds 87, 92, 95, 97 and 102. The compounds of the invention can be separated by conventional methods into R- and S- isomers; the invention includes both racemic and optically pure products. Resolution can be accomplished using resolving agents such as optically active dibenzoyltartaric acid, camphorsulfonic acid, bis-o-toluoyltartaric acid, tartaric acid, and diacetyl tartaric acid.

A second procedure useful in resolving primary and secondary amine compounds of Formula I involves their conversion to diastereomeric amides using an optically active acid. The diastereomeric amides are separated and the amide bond is cleaved to afford the optically pure Formula I compounds. This procedure is illustrated in Examples 49 and 50 for the preparation of the optical isomers of compound 29 using t-butoxycarbonyl-L-phenylalanine as the resolving agent. For the resolution, racemic compound 26 was coupled to t-butoxycarbonyl-L-phenylalanine and the diastereomeric amide products were separated by chromatography into the (+) and (−) forms; each isomer was carried forward as described in detail for the "(−) isomer" below. The (−) isomer was reacted with trifluoracetic acid to give (−) N-(5,6-dihydro-2-oxo-4H-imidazo(4,5,1-ij)quinolin-5-yl)-L-phenylalanineamide. Edman degradation of this compound, by reaction with phenyl isothiocyanate followed by trifluoracetic acid, removed the phenylalanine residue and afforded the (−) form of compound 26. Further reaction of this product with propionaldehyde and sodium cyanoborohydride gave the (−) form of compound 29, the more active isomer.

Compounds where the $R_3$ substituent is alkyl exist as diastereomers in which the alkyl group and amine substituent ($NR_1R_2$) can be cis or trans to one another. The invention includes the use of such compounds as the isomer mixture (RR, RS, SR SS), the racemic diastereomers (R,R and S,S; or R,S and S,R) and the optically pure diastereomer. The diastereomer mixture can be separated by conventional means, e.g. by silica gel chromatography. The racemic diastereomers thus obtained may be resolved into optically pure compounds using the procedures described above.

The compounds listed below were tested and found to have possible useful antipsychotic activity properties as indicated by their having CNS activity ($ED_{50}$ numbers of less than 50 mg/kg values) in the known hypothermia and/or hypoxic stress tests; several of the compounds have also shown analgesic activity. For these tests, groups of 4 male CF-1 mice are dosed ip (sc in the hypoxic stress and HCl writhing tests) with suspensions or solutions in 0.25% aqueous methylcellulose. Doses of the compound under study began at 100 mg/kg and were decreased at a 0.3 log interval until no responders were obtained. The procedure described by Spearman and Karber, Finney, D. J. "Statistical Methods in Biological Assay", Chapter 20, was used to calculate the $ED_{50}$ and 95% confidence intervals.

In the hypothermia test, abdominal temperature was measured after 45 minutes. Mice with temperatures more than 2 standard deviations below the mean are hypothermic. This test is used to identify compounds which may be useful as antipsychotics or as hypotensives.

In the hypoxic stress test, following compound administration the mice were placed individually in stoppered 125 ml Erlenmeyer flasks 30 min after receiving the test agent. The survival time is recorded. Mice surviving more than the mean $+2$ standard deviations in parallel run controls are scored as showing a drug effect. This test is used to identify compounds which may be useful as anxiolytics.

For determination of analgesic activity, thirty minutes after test compound injection, the mice were injected i.p with 0.15% HCl, 10 ml/kg. Mice were then placed in plastic boxes and observed for fifteen minutes to record the number of animals failing to writhe. If at least three of the mice receiving the test compound failed to writhe, the compound was retested at lower dose levels.

In the hypothermia and hypoxic stress tests, compounds of the invention have been found more potent than related compounds, showing $ED_{50}$'s values as low as 0.05 mg/kg. The compounds also had good activity in the hypothermia test when the animals were dosed orally with the drug.

The dosage regimen for treating patients with the compounds of this invention is selected in accordance with a variety of factors including the type, age, weight, sex, and medical condition of the patient, the severity of the psychosis, the route of administration and the particular compound employed. An ordinarily skilled physician or psychiatrist will readily determine and prescribe the effective amount of compound to prevent or arrest the progress of the condition. In so proceeding, the physician or psychiatrist could employ relatively low dosages at first, subsequently increasing the dose until a maximum response is obtained.

Initial dosages of the compounds of the invention are ordinarily in the area of at least 10 mg up to about 1200 mg per day orally, which may be given in a single dose or in multiple doses. When other forms of administration are employed equivalent doses are administered. When dosages beyond 600 mg are employed, care should be taken with each subsequent dose to monitor possible toxic effects.

The compounds of this invention are administered in oral unit dosage forms such as tablets, capsules, pills, powders, or granules. They may also be introduced parenterally, (e.g., subcutaneously, intravenously, or intramuscularly), using forms known to the pharmaceutical art. They also may be administered rectally or vaginally in such forms as suppositories or bougies. In general, the preferred route of administration is oral.

The compounds of this invention can also be administered as pharmaceutically or therapeutically acceptable salt such as hydrochloride, hydrobromide, hydroiodide, sulfate, phosphate, acetate, propionate, lactate, maleate, malate, succinate, tartrate, cyclohexanesulfamates, methanesulfonates, ethanesulfonates, benzenesulfonates, toluenesulfonates and the like. Additionally, the compounds of this invention may be administered in a suitable hydrated form.

EXAMPLE 1

Benzyl methyl malonate

A mixture of dimethyl malonate (100 g, 0.75 mol) and benzyl alcohol (108 g, 1.0 mol) was heated for 2 h at 180° C. under a distillation head so as to remove the methanol generated in the reaction. The product was then distilled under reduced pressure to give a forerun of 55 g (a mixture of dimethyl malonate and benzyl alcohol) followed by 63 g (40%) of benzyl methyl malonate, bp 105°–115° C./0.2 mm (98% pure by GC). The pot residue consisted of 71 g (33%) of dibenzyl malonate (90% pure by GC).

EXAMPLE 2

Benzyl methyl bromomalonate

Bromine (17.6 g, 0.11 mol) was added to a stirred solution of benzyl methyl malonate (20.8 g, 0.10 mol) in carbon tetrachloride. After 30 minutes the solvent was removed under reduced pressure to give 28 g of product (85% pure by gc, containing 7% benzyl methyl malonate) which was used without further purification.

EXAMPLE 3

Diethyl (dipropylamino)malonate (compound VIb)

Dipropylamine (22.3 g, 0.22 mol) was added to a stirred solution of diethyl bromomalonate (47.8 g, 0.20 mol) in THF (400 mL) and the solution was stirred for 18 hours at room temperature. The precipitate of dipropylamine hydrobromide was filtered off and washed with THF. The THF phase was evaporated and the residual oil was partitioned between ethyl acetate (200 mL) and sodium hydroxide solution (10 mL of 4 N). The ethyl acetate phase was separated, washed with water (2×10 mL), and the solvent was removed under reduced pressure. The residual oil was dissolved in an equal volume of hexane and was applied to a silica gel column (420 g) which was eluted initially with ethyl acetate:hexane (1:20). The concentration of ethyl acetate in the eluant was increased slowly until all the diethyl (dipropylamino)malonate was eluted from the column. Fractions containing the compound as determined by TLC and GC were pooled and the solvent was removed to give diethyl (dipropylamino)malonate as an oil in 80–90% yield.

Compounds VIa and VIc-VIh were obtained using this procedure, but substituting dimethylamine, propylamine, N-methylbenzylamine, N-propylbenzylamine, benzylamine, α-methylbenzylamine, (R)-α-methylbenzylamine for dipropylamine.

Compounds VIi–VIp were obtained using this procedure, but substituting benzyl methyl bromomalonate for diethyl bromomalonate and using dimethylamine, dipropylamine, pyrrolidine, piperidine, morpholine, 4-methylpiperazine and imidazole as the amine reaction component.

EXAMPLE 4

Diethyl (N-(1,1-dimethylethoxycarbonyl)propylamino)malonate (compound VIIf)

Diethyl aminomalonate (21.1 g, 0.1 mol) was dissolved in ethanol and sodium ethoxide in ethanol (50 mL of 1 M) was added. Propionaldehyde (6.6 g, 0.11 mol) and sodium cyanoborohydride (3.6 g, 0.058 mol) were added to the stirred solution. After 30 minutes additional propionaldehyde (6.0 g) and sodium cyanoborohydride (2.6 g) were added to complete the reaction. The solution was evaporated, and the residue was partitioned between ethyl acetate and water. Evaporation of the ethyl acetate gave 25.1 g of diethyl (propylamino)malonate. This was mixed with di t-butyl dicarbonate (34 g, 0.156 mol) and the mixture was heated at 100° C. for 1 hour. The crude product was chromatographed on silica gel using ethyl acetate:hexane as the eluant to give 21.2 g of diethyl (N-(1,1-dimethylethoxycarbonyl)propylamino)malonate as an oil.

Compound VIIe was obtained by following the same procedure, but substituting propionyl chloride for di t-butyl dicarbonate.

EXAMPLE 5

Diethyl (1-oxopropyl)malonate (compound VIId)

Triethylamine (20 g, 0.2 mol) and propionic anhydride (12.54 g, 0.096 mol) were added to diethyl aminomalonate hydrochloride (20.40 g, 0.096 mol) in THF (300 mL) and the reaction was stirred at room temperature for 45 minutes. The solvent was removed under reduced pressure and the crude product was partitioned between ethyl acetate and water. The ethyl acetate phase was separated and evaporated to give 34.64 g of white solid. This was dissolved in hot ethyl acetate (60 mL), hexane (60 mL) was added, and the solution was filtered to remove insoluble material. The solution was cooled to −10° C. and filtered to give 17.63 g (72%) of diethyl (1-oxopropyl)malonate, mp 89°–93° C.

Compound VIIc was obtained by following the same procedure, but substituting di t-butyl dicarbonate for propionic anhydride.

EXAMPLE 6

8-(Bromomethyl)quinoline (compound X)

A mixture of 8-methylquinoline (45 g, 0.314 mol), N-bromosuccinimide (55 g, 0.309 mol) and benzoyl peroxide (1.5 g) in carbon tetrachloride (250 mL) was refluxed for 7 hours. The reaction was filtered and evaporated, and the crude product was crystallized from methanol (70 mL) to give 37.7 g of product. The mother liquors were chromatographed on silica gel in chloroform to give 17 g of material which was crystallized from ethyl acetate:hexane to give an additional 12.0 g of product.

EXAMPLE 7

Diethyl (formylamino)(8-quinolinylmethyl)propanedioate (compound XIa)

Diethyl (formylamino)malonate (22.0 g, 0.108 mol) was added to a stirred solution of sodium ethoxide in ethanol (prepared from 2.4 g of sodium and 250 mL of ethanol, 0.10 mol). After 5 min, 8-(bromomethyl)quinoline (22.0 g, 0.10 mol) was added and the solution was stirred for an additional 15 minutes. The solvent was removed under reduced pressure and the product was partitioned between ethyl acetate and water. The ethyl acetate was removed and the residual oil was crystallized from ether to give 19.9 g (58%) of diethyl (formylamino)(8-quinolinylmethyl)propanedioate, mp 120°–122° C. Anal. Calcd. for $C_{18}H_{20}N_2O_5$: C, 62.78; H, 5.85; N, 8.14. Found: C, 62.53; H, 6.03; N, 8.07.

EXAMPLE 8

N-(2,3,6,7-Tetrahydro-3-oxo-1H,5H-benzo(ij)quinolizin-2-yl)-formamide (compound XIIIa)

Part A. Ethyl 2,3,6,7-tetrahydro-3-oxo-2(formylamino)-1H,5H-benzo(ij)quinolizine-2-carboxylate (compound XIIa)

A mixture of diethyl (formylamino)(8-quinolinylmethyl)malonate (9.2 g, 26.7 mmol) and platinum oxide (0.7 g) in glacial acetic acid (150 mL) was hydrogenated (50 lb initial pressure) for 15 minutes (hydrogen uptake ca. 2 equiv). The mixture was filtered through celite and the solvent removed under reduced pressure. The product was partitioned between ethyl acetate and sodium hydroxide solution. The ethyl acetate phase was washed with water, the ethyl acetate was evaporated, and the product was crystallized from ether to give 7.8 g (97%) of ethyl 2,3,6,7-tetrahydro-3-oxo-2-(formylamino)-1H,5H-benzo(ij)quinolizine-2-carboxylate, mp 103°–106° C. Anal. Calcd. for $C_{16}H_{18}N_2O_4$: C, 63.56; H, 6.00; N, 9.27. Found: C, 63.51; H, 6.09; N, 9.18.

Part B. N-(2,3,6,7-Tetrahydro-3-oxo-1H,5H-benzo(ij)quinolizin-2-yl)formamide (compound XIIIa)

Sodium hydroxide solution (5.0 mL of 4.0 N, 20 mmol) was slowly added to ethyl 2,3,6,7-tetrahydro-3-oxo-2-(formylamino)-1H,5H-benzo(ij)quinolizine-2-carboxylate (3.04 g, 10.0 mmol) in methanol (25 mL). After stirring at room temperature for 30 min, hydrochloric acid (5.0 mL of 4.0 N) was added and the precipitate was filtered off, washed with water and air dried to give 2.4 g of N-(2,3,6,7-tetrahydro-3-oxo-1H,5H-benzo(ij)-quinolizin-2-yl)formamide, mp 149°–152° C. A portion of the product was recrystallized from ethyl acetate for analysis; mp 140°–143°. Anal. Calcd. for $C_{13}H_{14}N_2O_2$: C, 67.81; H, 6.13; N, 12.17. Found: C, 67.67; H, 6.07; N, 11.94.

EXAMPLE 9

2,3,6,7-Tetrahydro-N,N-dimethyl-1H,5H-benzo(ij)-quinolizin-2-amine (Compound 1)

Part A. 2,3,6,7-Tetrahydro-3-oxo-1H,5H-benzo(ij)-quinolizin-2-amine (compound XIV)

A solution of N-(2,3,6,7-tetrahydro-3-oxo-1H,5H-benzo(ij)quinolizin-2-yl)-formamide (0.8 g, 3.4 mmol) in ethanolic hydrogen chloride (10 mL of 4.2 M) was heated at 50° C. for 2 hours. The ethanol was cooled, an equal volume of ether was added, and the precipitate was filtered off and washed with ether to give 0.78 g of 2,3,6,7-tetrahydro-3-oxo-1H,5H-benzo(ij)quinolizin-2-amine hydrochloride, mp 216°-221° C. The product was recrystallized for analysis; mp 219°-222° C. Anal. Calcd. for $C_{12}H_{14}N_2O \cdot HCl$: C, 60.37; H, 6.33; Cl, 14.85; N, 11.74. Found: C, 59.89; H, 6.42; Cl, 15.41; N, 11.68.

Part B. 2,3,6,7-Tetrahydro-N,N-dimethyl-1H,5H-benzo(ij)quinolizin-2-amine (compound 1)

A mixture of 2,3,6,7-tetrahydro-3-oxo-1H,5H-benzo(ij)quinolizin-2-amine (2.0 g), 30% formaldehyde solution (1 mL) and 10% palladium/carbon (0.5 g) in ethanol (150 mL) was hydrogenated (50 lb initial hydrogen pressure) until uptake of hydrogen was complete (2 hours). The solution was filtered to remove the catalyst, evaporated, the crude product was dissolved in ether (300 mL) and lithium aluminum hydride (1.5 g) was added. After 1 hour, ethyl acetate was added, the solvents were removed under reduced pressure, and the product was partitioned between ethyl acetate and water. Evaporation of the ethyl acetate gave an oil which was purified by chromatography on silica gel to give 1.03 g of 2,3,6,7-tetrahydro-N,N-dimethyl-1H,5H-benzo(ij)-quinolizin-2-amine.

The bulk of the product was converted to the maleate salt, mp 135°-137° C. from methanol:ether. A sample was recrystallized for analysis; mp 135°-137° C. Anal. Calcd. for $C_{14}H_{20}N_2 \cdot C_4H_4O_4$: C, 65.04; H, 7.28; N, 8.43. Found: C, 64.72; H, 7.43; N, 8.20.

EXAMPLE 10

2,3,6,7-Tetrahydro-N-methyl-1H,5H-benzo(ij)quinolizin-2-amine and
N-Ethyl-2,3,6,7-tetrahydro-N-methyl-1H,5H-benzo(ij)quinolizin-2-amine (Compounds 2 and 3)

N-(2,3,6,7-Tetrahydro-3-oxo-1H,5H-benzo(ij)-quinolizin-2-yl)formamide (4 g, 0.017 mol) was added in 0.5 g aliquots every 10 min to a stirred solution of lithium aluminum hydride (2.77 g, 0.073 mol) in anhydrous ether (500 mL). After stirring overnight at room temperature the reaction was refluxed for 3 hours, cooled on ice and quenched with ethyl acetate and methanol. The solvent was evaporated under reduced pressure and the crude product was partitioned between ethyl acetate (800 mL) and water (40 mL). The ethyl acetate was separated, washed with water, and the ethyl acetate was evaporated to give 3.64 g of crude product. The products were separated by chromatography on silica gel in chloroform to give, as the first product eluted from the column, 1.4 g of N-ethyl-2,3,6,7-tetrahydro-N-methyl-1H,5H-benzo(ij)-quinolizin-2-amine. The compound was converted to the maleate salt, mp 90°-100° C. from methanol:ether. The product was recrystallized for analysis; mp 94°-98° C. Anal. Calcd. for $C_{15}H_{22}N_2 \cdot C_4H_4O_4$: C, 65.87; H, 7.57; N, 8.09. Found: C, 65.53; H, 7.81; N, 8.08.

Continued elution of the column gave 1.3 g of 2,3,6,7-tetrahydro-N-methyl-1H,5H-benzo(ij)quinolizin-2-amine which was converted to the maleate salt, mp 151°-155° C. from methanol:ether. Anal. Calcd. for $C_{13}H_{18}N_2 \cdot C_4H_4O_4$: C, 64.13; H, 6.97; N, 8.80. Found: C, 63.79; H, 7.16; N, 8.62.

EXAMPLE 11

Diethyl
((1-oxopropyl)amino)(8-quinolinylmethyl)propanedioate (compound XIb)

Diethyl (1-oxopropyl)malonate (15.14 g, 0.065 mol) was added to a stirred solution of sodium ethoxide in ethanol (165 mL of 0.4 M, 0.066 mol). After 5 minutes, 8-(bromomethyl)quinoline (13.15 g, 0.059 mol) was added and the solution was stirred for an additional 15 minutes. The solvent was removed under reduced pressure and the product was dissolved in ethyl acetate (300 mL) which was washed with water (3×10 mL). The ethyl acetate was removed and the residual solid (27.3 g) was crystallized from ethyl acetate:hexane to give 21.6 g of tan crystals, mp 80°-100° C. Recrystallization of an aliquot (4 g) from ethyl acetate:hexane gave 2.87 g of tan crystals, mp 104°-106° C. Anal. Calcd. for $C_{20}H_{24}N_2O_5$: C, 64.50; H, 6.50; N, 7.52. Found: C, 64.25; H, 6.51; N, 7.51.

EXAMPLE 12

Ethyl 2,3,6,7-tetrahydro-3-oxo-2-((1-oxopropyl)amino)-1H,5H-benzo(ij)quinoliz-ine-2-carboxylate (compound XIIb).

A mixture of diethyl ((1-oxopropyl)amino)(8-quinolinylmethyl)-propanedioate (17.47 g, 0.047 mol) and platnium oxide (0.72 g) in glacial acetic acid (150 mL) was hydrogenated (50 lb initial pressure) until hydrogen uptake ceased (1.8 equiv). The mixture was filtered through celite and the solvent removed under reduced pressure. The product was crystallized from ethyl acetate to give 12.08 g of crystals, mp 136°-140° C. A sample was recrystallized from ethyl acetate for analysis; mp 137°-141° C. Anal. Calcd. for $C_{18}H_{22}N_2O_4$: C, 65.44; H, 6.71; N, 8.48. Found: C, 65.66; H, 6.64; N, 8.43.

EXAMPLE 13

N-(2,3,6,7-Tetrahydro-3-oxo-1H,5H-benzo(ij)quinolizin-2-yl)-propanamide (compound XIIIb)

Sodium hydroxide solution (10 mL of 4.0 N, 0.04 mol) was slowly added to ethyl 2,3,6,7-tetrahydro-3-oxo-2-((1-oxopropyl)amino)-1H,5H-benzo(ij)quinolizine-2-carboxylate (3.33 g, 0.010 mol) in methanol (50 mL). After stirring at room temperature for 30 minutes, the solvent was removed under reduced pressure. The resulting solid was dissolved in water (20 mL) and methanol (trace), neutralized with 4N HCl (10 mL, 0.04 mol), cooled to −10° C., and the precipitate was filtered off and air dried to give 2.86 g of 2,3,6,7-tetrahydro-3-oxo-2-((1-oxopropyl)amino)-1H,5H-benzo(ij)-quinolizine-2-carboxylic acid. This was refluxed in ethanol for 20 minutes to effect decarboxylation. The ethanol was removed under reduced pressure and the solid was crystallized from ethyl acetate:hexane to give 1.85 g of N-(2,3,6,7-tetrahydro-3-oxo-1H,5H-benzo(ij)-quinolizin-2-yl)propanamide, mp 149°-152° C. A sample was recrystallized for analysis; mp 152°-154° C. Anal. Calcd. for $C_{15}H_{18}N_2O_2$: C, 69.74; H, 7.02; N, 10.85. Found: C, 69.33; H, 7.33; N, 10.68.

EXAMPLE 14

2,3,6,7-Tetrahydro-N-propyl-1H,5H-benzo(ij)quinolizin-2-amine (compound 4)

N-(2,3,6,7-Tetrahydro-3-oxo-1H,5H-benzo(ij)-quinolizin-2-yl)propanamide (2.5 g, 0.01 mol) was dissolved in anhydrous ether (500 mL). The solution was cooled to 0° C., lithium aluminum hydride (1.46 g, 0.038 mol) was added and the reaction was refluxed for 4 hours. The reaction was quenched with ethyl acetate and methanol, the solvents were removed under reduced pressure and the material was partitioned between ethyl acetate (400 mL) and water (50 mL). Evaporation of the ethyl acetate phase gave 2.35 g of yellow oil. The product was purified by chromatography on silica gel. Elution of the column with 1% and 2.5% methanol:chloroform gave 2.07 g of 2,3,6,7-tetrahydro-N-propyl-1H,5H-benzo(ij)quinolizin-2-amine.

The bulk of the product was converted to the hemifumarate salt which was recrystallized from methanol:ether; mp 190°–194° C. Anal. Calcd. for $C_{15}H_{22}N_2 \cdot \frac{1}{2}C_4H_4O_4$: C, 70.80; H, 8.39; N, 9.71. Found: C, 70.37; H, 8.26; N, 9.65.

EXAMPLE 15

2,3,6,7-Tetrahydro-N,N-dipropyl-1H,5H-benzo(ij)-quinolizin-2-amine (compound 5)

A mixture of 2,3,6,7-tetrahydro-N-propyl-1H,5H-benzo(ij)quinolizin-2-amine (2.33 g, 0.01 mol), propyl iodide (5.16 g, 0.03 mol) and anhydrous potassium carbonate (3 g, 0.02 mol) in dimethylformamide (75 mL) was stirred for 5 hours at 90° C. At this time additional propyl iodide (1.72 g, 0.01 mol) and potassium carbonate (0.05 g, 0.0036 mol) were added and the reaction was continued for an additional 2 hours. The reaction was cooled, filtered to remove inorganic material, and the solvent was removed under reduced pressure. The product was partitioned between ethyl acetate (800 mL) and 4N sodium hydroxide (20 mL, 0.08 mol), the organic layer concentrated, filtered, and chromatographed on silica gel in 5–30% ethyl acetate:hexane to give 2.19 g of 2,3,6,7-tetrahydro-N,N-dipropyl-1H,5H-benzo(ij)quinolizin-2-amine.

A portion of the product was converted to the fumarate salt, mp 112.5°–116° C. Recrystallization from methanol:ether gave light brown crystals, mp 112°–116° C. Anal. Calcd. for $C_{18}H_{28}N_2 \cdot C_4H_4O_4$: C, 68.01; H, 8.30; N, 7.21. Found: C, 67.73; H, 8.47; N, 7.14.

EXAMPLE 16

4-Methyl-1H-benzimidazole (compound XVIII)

Part A 3-Methyl-1,2-benzenediamine (compound XVII)

2-Methyl-6-nitroaniline (15.2 g, 0.1 mol) was dissolved by heating in ethanol (150 mL). The solution was cooled, 10% palladium on carbon (1.0 g) was added and the solution was hydrogenated (50 lb initial hydrogen pressure) until uptake of hydrogen ceased (1 hour). The catalyst was filtered off and the ethanol was removed under reduced pressure to give 11.9 g (98%) of 3-methyl-1,2-benzenediamine as a solid which was used without purification.

Part B. 4-Methyl-1H-benzimidazole (Compound XVIII)

A mixture of 3-methyl-1,2-benzenediamine (11.9 g) and formic acid (150 mL) was heated at 70° C. for 15 minutes. The solvent was removed under reduced pressure and the residual oil was stirred with water (100 mL) and sodium hydroxide solution (65 mL of 4.0 N) was added until the solution was just basic. The precipitate was filtered off, washed with water, and air dried to give 11.6 g (90%) of 4-methyl-1H-benzimidazole, mp 141°–145° C.

EXAMPLE 17 t-Butyl 4-(bromomethyl)-1H-benzimidazole-1-carboxylate (compound XXa)

Part A. t-butyl 4-methyl-1H-benzimidazole-1-carboxylate (compound XIXa)

A mixture of 4-methyl-1H-benzimidazole (11.6 g, 0.088 mol) and di t-butyl dicarbonate (21.1 g, 0.097 mol) was heated at 80° C. in dioxane (200 mL) for 1 hour. The solvent was removed under reduced pressure and the residual oil (24.3 g) was chromatographed on silica gel using ethyl acetate:hexane as the eluant to give 18.7 g (92%) of t-butyl 4-methyl-1H-benzimidazole-1-carboxylate as an oil.

Part B. t-butyl 4-(bromomethyl)-1H-benzimidazole-1-carboxylate (compound XXa)

A mixture of t-butyl 4-methyl-1H-benzimidazole-1-carboxylate (11.6 g, 0.05 mol), N-bromosuccinide (8.9 g, 0.05 mol) and benzoyl peroxide (0.25 g) in carbon tetrachloride (100 mL) was stirred at reflux for 1 hour. The solution was cooled and filtered to remove succinimide by-products and the solvent was removed. The crude product was chromatographed on silica gel using ethyl acetate:hexane (1:20) as the initial eluant to give, as the first major product eluted from the column, 1.6 g of t-butyl 4-(dibromomethyl)-1H-benzimidazole-1-carboxylate; recrystallization from hexane gave 1.04 g of product, mp 101°–104° C. Anal. Calcd. for $C_{13}H_{14}Br_2N_2O_2$: C, 40.03; H, 3.62; Br, 40.92; N, 7.18. Found: C, 39.87; H, 3.83; Br, 41.18; N, 7.19.

Continued elution of the column gave 10.4 g of t-butyl 4-(bromomethyl)-1H-benzimidazole-1-carboxylate. The compound was recrystallized from hexane to give 9.6 g of product, mp 87°–89° C. Anal. Calcd. for $C_{13}H_{15}BrN_2O_2$: C, 50.18; H, 4.86; Br, 25.68; N, 9.00. Found: C, 50.16; H, 5.04; Br, 25.71; N, 9.11.

Continued elution of the column gave 0.95 g of recovered t-butyl 4-(bromomethyl)-1H-benzimidazole-1-carboxylate.

Following the procedure of Example 17 part B but substituting methyl 4-methyl-1H-benzimidazole-1-carboxylate for t-butyl 4-methyl-1H-benzimidazole-1-carboxylate there was obtained methyl 4-(bromomethyl)-1H-benzimidazole-1-carboxylate (compound XXb).

Following the procedure of Example 17 part B but substituting 1-acetyl-4-methyl-1H-benzimidazole for t-butyl 4-methyl-1H-benzimidazole-1-carboxylate there was obtained 1-acetyl-4-(bromomethyl)benzimidazole (compound XXc), mp 109°–112° C. Anal. Calcd. for $C_{10}H_{10}BrN_2O$: C, 47.45; H, 3.58; Br, 31.58; N, 11.07. Found: C, 47.47; H, 3.82; Br, 29.17; N, 11.21.

EXAMPLE 18

5,6-Dihydro-N,N-dipropyl-4H-imidazo(4,5,1-ij)quinolin-5-amine (compound 6)

Part A. Diethyl {(1,1-dimethylethoxycarbonyl)-1H-benzimidazole-4-yl)methyl)-(dipropylamino)propanedioate (compound XXIa)

Potassium hydride (3.3 g of 40% oil suspension, washed with ether to remove oil, 0.03 mol) was added to a stirred solution of diethyl (dipropylamino)-malonate (10.2 g, 0.039 mol) in dry THF (100 mL). After 5 minutes, t-butyl, 4-(bromomethyl)-1H-benzimidazole-1-carboxylate (6.22 g, 0.02 mol) was added and the solution was refluxed for 6 hours. The solvent was removed under reduced pressure and the residual oil was partitioned between ethyl acetate and water. After evaporation of the ethyl acetate, the crude product was chromatographed on silica gel using ethyl acetate:hexane as the eluant to give 7.9 g of diethyl {((1,1-dimethylethoxycarbonyl)-1H-benzimidazole-4-yl)methyl}(dipropylamino)-propanedioate as an oil.

Part B. Ethyl α-(dipropylamino)-1H-benzimidazole-4-propanoate (compound XXII)

A mixture of diethyl {((1,1-dimethylethoxycarbonyl)-1H-benzimidazole-4-yl)methyl}(dipropylamino) propanedioate (3.4 g, 6.9 mmol) was dissolved in ethanol (50 ml) and treated with sodium ethoxide in ethanol (35 mL of 0.8 M, 4 equiv) and water (1.0 mL) and the reaction was refluxed for 4 hours. The solution was then cooled, neutralized by addition of 15 mL of 2.2 N HCl in ethanol, filtered to remove sodium chloride, and the solvent was removed under reduced pressure. The product was partitioned between ethyl acetate and water, and the ethyl acetate was removed, and the crude product was chromatographed on silica gel using chloroform as the initial eluant. Elution of the column with 5% methanol chloroform gave 1.60 g of ethyl α-(dipropylamino)-1H-benzimidazole-4-propanoate. The product was crystallized from ethyl acetate:hexane; mp 78°-80° C. Anal. Calcd. for $C_{18}H_{27}N_3O_2$: C, 68.11; H, 8.57; N, 13.24. Found: C, 68.41; H, 8.51; N, 13.22.

Part C β-(Dipropylamino)-1H-benzimidazole-4-propanol (compound XXIII)

Lithium aluminum hydride (250 mg, 6.6 mmol) was added at 0° C. to a stirred solution of ethyl α-(dipropylamino)-1H-benzimidazole-4-propanoate (1.5 g, 4.7 mmol) in dry THF (50 mL), and the solution was allowed to warm to room temperature. TLC in 10% methanol:chloroform showed that the reaction was complete in 15 minutes. Ethanol (5 mL) was added and the solvents were removed under reduced pressure. The residue was partitioned between ethyl acetate and water. Evaporation of the ethyl acetate gave 1.3 g of β-(dipropylamino)-1H-benzimidazole-4-propanol which was used without further purification.

Part D
5,6-Dihydro-N,N-dipropyl-4H-imidazol(4,5,1-ij)quinolin-5-amine (compound 6)

Triphenylphosphine (625 mg, 2.4 mmol) was added to a stirred solution of β-(dipropylamino)-1H-benzimidazole-4-propanol (600 mg, 2.18 mmol) in methylene chloride (12 mL). After solution was complete, carbon tetrabromide (940 mg, 2.8 mmol) was added and the solution was stirred for 30 minutes. Methylene chloride (20 mL) was added and the solution was extracted with 25 mL 1.0 N hydrochloric acid. The methylene chloride was separated, reextracted with 10 mL 1.0 N HCl, and the combined aqueous extracts were basified (20 mL of 4.0 N NaOH) and extracted with ethyl acetate. After removing the ethyl acetate, the product was chromatographed on silica gel using chloroform as the initial eluant to give 380 mg of product. A sample was crystallized from hexane for analysis; mp 95°-98° C. Anal. Calcd. for $C_{16}H_{23}N_3$: C, 74.66; H, 9.01; N, 16.33. Found: C, 74.28; H, 9.25; N, 16.36.

EXAMPLE 19

5,6-Dihydro-N,N-dimethyl-4H-imidazo(4,5,1-ij)quinoline-5-amine (compound 7)

Part A (Dimethylamino){((1,1-dimethylethoxycarbonyl)-1H-benzimidazole-4-yl)methyl}-propanedioic acid methyl benzyl diester This compound was obtained by following the procedure of Example 18 part A, but substituting (dimethylamino)propanedioic acid methyl benzyl diester (compound VIi) for diethyl (dipropylamino)malonate.

Part B. Methyl α-(dimethylamino)-1H-benzimidazole-4-propanoate.

A mixture of (dimethylamino){((1,1-dimethylethoxycarbonyl)-1H-benzimidazole-4-yl)methyl}-propanedioic acid methyl benzyl diester (6.0 g) and 10% palladium charcoal (1 g) in ethanol (150 mL) was hydrogenated until hydrogen uptake ceased. The solution was filtered and evaporated to give 4.1 g of methyl α-(dimethylamino)-1H-benzimidazole-4-propanoate as an oil.

Part C. β-(Dimethylamino)-1H-benzimidazole-4-propanol

This compound was obtained by following the procedure of Example 18 part C, but substituting methyl α-(dimethylamino)-1H-benzimidazole-4-propanoate for ethyl α-(dipropylamino)-1H-benzimidazole-4-propanoate.

Part D. 5,6-Dihydro-N,N-dimethyl-4H-imidazo(4,5,1-ij)quinolin-5-amine

This compound was obtained by following the procedure of Example 18 part C but substituting β-(dimethylamino)-1H-benzimidazole-4-propanol for β-(dipropylamino)-1H-benzimidazole-4-propanol.

The bulk of the product was converted to the hydrochloride salt, mp 264°-265° C. from methanol:ether. Anal. Calcd. for $C_{12}H_{15}N_3 \cdot 2HCl$: C, 52.56; H, 6.25; Cl, 25.86; N, 15.33. Found: C, 52.44; H, 6.53; Cl, 25.64; N, 15.18.

EXAMPLE 20

1-(5,6-Dihydro-4H-imidazo(4,5,1-ij)quinolin-5-yl)pyrrolidine (compound 8)

This compound was prepared by following the procedure of Example 19, but substituting (1-pyrrolidinyl)-propanedioic acid methyl benzyl diester (compound VIk) for (dimethylamino)propanedioic acid methyl benzyl diester (compound VIi). The bulk of the product was converted to the dihydrochloride salt, mp 291°-294° C.

EXAMPLE 21

1-(5,6-Dihydro-4H-imidazo(4,5,1-ij)quinolin-5-yl)piperidine (compound 9)

This compound was prepared by following the procedure of Example 19, but substituting (1-piperidinyl)-propanedioic acid methyl benzyl diester (compound VIm) for (dimethylamino)propanedioic acid methyl benzyl diester (compound VIi). The bulk of the product was converted to the dihydrochloride salt, mp 287°-290° C.

EXAMPLE 22

4-(5,6-Dihydro-4H-imidazo(4,5,1-ij)quinolin-5-yl)morpholine (compound 10)

This compound was prepared by following the procedure of Example 19, but substituting (4-morpholinyl)- propanedioic acid methyl benzyl diester (compound VIn) for (dimethylamino)propanedioic acid methyl benzyl diester (compound VIi). The bulk of the product was converted to the dihydrochloride salt, mp 290°-292° C.

EXAMPLE 23

1-(5,6-Dihydro-4H-imidazo(4,5,1-ij)quinolin-5-yl)-imidazole (compound 11)

This compound was prepared by following the procedure of Example 19, but substituting (1-imidazolyl)-propanedioic acid methyl benzyl diester (compound VIp) for (dimethylamino)propanedioic acid methyl benzyl diester (compound VIi). The bulk of the product was converted to the monohydrobromide salt, mp 239°-242° C.

EXAMPLE 24

1-(5,6-Dihydro-4H-imidazo(4,5,1-ij)quinolin-5-yl)-4-methylpiperazine (compound 12)

This compound was prepared by following the procedure of Example 19, but substituting (4-methyl-1-piperazinyl)propanedioic acid methyl benzyl diester (compound VIq) for (dimethylamino)propanedioic acid methyl benzyl diester (compound VIi).

EXAMPLE 25

N-(1-Phenylethyl)-5,6-Dihydro-4H-imidazo(4,5,1-ij)quinolin-5-amine (compound 13)

This compound was prepared by following the procedure of Example 18, but substituting diethyl (1-phenylethylamino)malonate (compound VIg) for diethyl (dipropylamino)malonate (compound VIb).

EXAMPLE 26 t-Butyl 4-(bromomethyl)-5-methoxy-1H-benzimidazole-1-carboxylate

Part A. 3-Chloro-2-methyl-6-nitrobenzenamine

A suspension of 2,6-dichloro-3-nitrotoluene (6.0 g, 29 mmol) in 50% methanolic ammonia (60 mL) was stirred at 130° C. (340 lb pressure) for 18 hours. The autoclave was cooled to −30° C., opened, and the precipitate was filtered off and washed with methanol to give 4.14 g (76%) of 3-chloro-2-methyl-6-nitrobenzenamine.

Part B. 3-Methoxy-2-methyl-6nitrobenzenamine

Sodium methoxide in methanol (110 mL of 25% solution, 0.49 mol, 20 equiv) was added to a stirred suspension of 3-chloro-2-methyl-6-nitrobenzenamine (4.0 g, 23.5 mmol) in methanol (250 mL) and the mixture was stirred at reflux for 18 hours. The solution was cooled, neutralized with methanolic hydrogen chloride, filtered to remove sodium chloride, and the solvent was removed under reduced pressure. The residual solid was partitioned between ethyl acetate and water. Evaporation of the ethyl acetate gave 3.7 g (86%) of 3-methoxy-2-methyl-6-nitrobenzenamine.

Part C. 4-Methoxy-3-methyl-1,2-benzenediamine

A mixture of 3-methoxy-2-methyl-4-nitrobenzenamine (3.5 g, 19.0 mmol) and 10% palladium on carbon (1.0 g) in absolute ethanol (150 mL) was hydrogenated (50 lb initial hydrogen pressure) until hydrogen uptake was complete (30 minutes). The solution was filtered through celite and the ethanol was removed to give 2.84 g (98%) of 4-methoxy-3-methyl-1,2-benzenediamine.

Part D. 5-Methoxy-4-methyl-1H-benzimidazole

A mixture of 4-methoxy-3-methyl-1,2-benzenediamine (2.8 g, 18.4 mmol) and formic acid (30 mL) was heated at 60° C. for 30 minutes. The formic acid was removed under pressure and the product was partitioned between chloroform and water containing sufficient sodium hydroxide to basify the solution. After evaporation of the solvent the crude product was chromatographed (methanol:chloroform) to give 2.55 g (84%) of 5-methoxy-4-methyl-1H-benzimidazole.

Part E. t-Butyl 5-methoxy-4-methyl-1H-benzimidazole-1-carboxylate

A mixture of 5-methoxy-4-methyl-1H-benzimidazole (2.5 g, 15.4 mmol) and di-t-butyl dicarbonate (4.2 g, 19.3 mmol) in dioxane (70 mL) was heated at 100° C. for 1 hour. After evaporation the solvent, the residue was chromatographed on silica gel to give 3.75 g (93%) of t-butyl 5-methoxy-4-methyl-1H-benzimidazole-1-carboxylate.

Part F. t-Butyl 4-(bromomethyl)-5-methoxy-1H-benzimidazole-1-carboxylate

A mixture of N-bromosuccinimide (2.66 g, 15.0 mmol), benzoyl peroxide (0.35 g) and t-butyl 5-methoxy-4-methyl-1H-benzimidazole-1-carboxylate (3.70 g, 14.1 mmol) in carbon tetrachloride (70 mL) was refluxed for 1 hour. The solution was cooled, filtered to remove succinimide by-products, evaporated, dissolved in ethyl acetate and chromatographed on silica gel using ethyl acetate:hexane as the eluant to give 4.8 g of product. This was crystallized from ethyl acetate:hexane to give 3.6 g (75%) of t-butyl 4-(bromomethyl)-5-methoxy-1H-benzimidazole-1-carboxylate, mp 127°-129° C. Anal. Calcd. for $C_{14}H_{17}BrN_2O_3$: C, 49.28; H, 5.02; Br, 23.42; N, 8.21. Found: C, 49.27; H, 4.98; Br, 26.81; N, 7.71.

EXAMPLE 27

5,6-Dihydro-7-methoxy-N,N-dipropyl-4H-imidazo(4,5,1-ij)quinolin-5-amine (compound 14)

The compound was prepared by following the procedure of Example 18, but substituting t-butyl 4-(bromomethyl)-5-methoxy-1H-benzimidazole-1-carboxylate for t-butyl 4-(bromomethyl)-1H-benzimidazole-1H-carboxylate. The product was crystallized from pentane; mp 46°-49° C. Anal. Calcd. for $C_{17}H_{25}N_3O$: C, 71.04; H, 8.77; N, 14.62. Found: C, 70.80; H, 8.89; N, 14.80.

The bulk of the product was converted to the dihydrochloride salt.

EXAMPLE 28

5,6-Dihydro-8-methoxy-N,N-dipropyl-4H-imidazo(4,5,1-ij)quinolin-5-amine (compound 15)

This compound was prepared by following the procedure of Example 18, but substituting t-butyl 4-(bromomethyl)-6-methoxy-1H-benzimidazole-1-carboxylate for t-butyl 4-(bromomethyl)-1H-benzimidazole-1-carboxylate.

EXAMPLE 29

5,6-Dihydro-9-methoxy-N,N-dipropyl-4H-imidazo(4,5,1-ij)quinolin-5-amine (compound 16)

This compound was prepared by following the procedure of Example 18, but substituting t-butyl 4-(bromomethyl)-7-methoxy-1H-benzimidazole-1-carboxylate for t-butyl 4-(bromomethyl)-1H-benzimidazole-1-carboxylate.

EXAMPLE 30

5,6-Dihydro-7-methoxy-N,N-dimethyl-4H-imidazo(4,5,1-ij)quinolin-5-amine (compound 17)

This compound was prepared by following the procedure of Example 18, but substituting t-butyl 4-(bromomethyl)-5-methoxy-1H-benzimidazole-1-carboxylate for t-butyl 4-(bromomethyl)-1H-benzimidazole-1-carboxylate and diethyl (dimethylamino)malonate for diethyl (dipropylamino)malonate.

EXAMPLE 31

7-Chloro-5,6-dihydro-N,N-dipropyl-4H-imidazo(4,5,1-ij)quinolin-5-amine (compound 18)

This compound was prepared by following the procedure of Example 18, but substituting t-butyl 5-chloro-4-(bromomethyl)-1H-benzimidazole-1-carboxylate for t-butyl 4-(bromomethyl)-1H-benzimidazole-1-carboxylate.

EXAMPLE 32

5-(Dipropylamino)-5,6-dihydro-4H-imidazo-(4,5,1-ij)quinolin-7-ol (compound 19)

5,6-Dihydro-7-methoxy-N,N-dipropyl-4H-imidazo(4,5,1-ij)quinolin-5-amine (1.0 g) was heated at 130° C. in 48% hydrobromic acid for 2 hours. The solution was cooled and was then evaporated under reduced pressure. The solid thus obtained was crystallized from methanol:ether; mp 270° C.

EXAMPLE 33

5,6-Dihydro-5-(dipropylamino)-4H-imidazo(4,5,1-ij)quinolin-8-ol (compound 20)

This componud was prepared by following the procedure of Example 32, but substituting 5,6-dihydro-8-methoxy-N,N-dipropyl-4H-imidazo(4,5,1-ij)quinolin-5-amine for 5,6-dihydro-7-methoxy-N,N-dipropyl-4H-imidazo(4,5,1-ij)quinolin-5-amine.

EXAMPLE 34

5,6-Dihydro-5-(dipropylamino)-4H-imidazo(4,5,1-ij)quinolin-9-ol (compound 21)

This compound was prepared by following the procedure of Example 32, but substituting 5,6-dihydro-9-methoxy-N,N-dipropyl-4H-imidazo(4,5,1-ij)quinolin-5-amine for 5,6-dihydro-7-methoxy-N,N-dipropyl-4H-imidazo(4,5,1-ij)quinolin-5-amine.

EXAMPLE 35

N-(3-quinolyl)formamide (compound XXV)

A solution of acetic formic anhydride was prepared by slowly adding 95-97% formic acid (20.80 g, 17.05 mL, 0.45 mol) to acetic anhydride (40.84 g, 37.7 mL, 0.40 mol) at 0° C. The solution was stirred at room temperature for 2 hours, then added to a stirred solution of 3-aminoquinoline (28.84 g, 0.20 mol) in dry tetrahydrofuran (300 mL). After 15 minutes, the solution was evaporated, methanol (50 mL) was added, and the solution stirred for an additional 30 minutes. The solution was then evaporated under reduced pressure and the residual oil was triturated with ether. The resulting white solid was filtered to give 28.7 g (84%) of product, mp 157°-160° C. Anal. Calcd. for $C_{10}H_8N_2O$: C, 69.75; H, 4.68; N, 16.27. Found: C, 69.45; H, 4.78; N, 16.31.

EXAMPLE 36

N-(1-Formyl-1,2,3,4-tetrahydro-3-quinolyl)formamide (compound XXVI)

A mixture of N-(3-quinolyl)formamide (30.0 g, 0.175 mol), platinum oxide (2.0 g) and acetic acid (300 mL) was hydrogenated (50 lb. initial $H_2$ pressure) until 2 equivalents of $H_2$ were consumed (reaction time 3 hours). The mixture was filtered through celite and the acetic acid removed under pressure. It was dissolved in ethyl acetate and washed with NaOH solution and water. Evaporation of the ethyl acetate gave 29.4 g of crude material. This was dissolved in 200 mL THF and acetic formic anhydride (prepared from formic acid (27.2 g, 0.59 mol) and acetic anhydride (53.5 g, 0.52 mol) was added at 0° C. After 15 minutes, the solution was allowed to warm to room temperature, and after an additional 15 minutes, methanol (60 mL) was added. The solution was evaporated and the resulting oil was partitioned between ethyl acetate and 4N sodium hydroxide solution. The sodium hydroxide solution was repeatedly extracted with ethyl acetate. The combined ethyl acetate was evaporated, and the crude product was purified by chromatography on silica gel using 2.5% methanol:chloroform as eluant to give 22.55 g (69%) of product. An analytical sample was crystallized from methanol:ether (1:3); mp 125°-128° C. Anal. Calcd. for $C_{11}H_{12}N_2O_2$: C, 64.69; H, 5.92; N, 13.72. Found: C, 64.60; H, 5.97; N, 13.66.

EXAMPLE 37

N-(1-Formyl-6-bromo-1,2,3,4-tetrahydro-3-quinolyl)-formamide (compound XXVII)

Bromine (10.2 g, 0.064 mol) was added to a stirred solution of N-(1-formyl-1,2,3,4-tetrahydro-3-quinolyl)-formamide (14.0 g, 0.065 mol) in acetic acid (70 mL) containing anhydrous sodium acetate (10.2 g, 0.12 mol). The solution was stirred for 30 minutes and water (500 mL) was added. The precipitate was filtered off and air dried to give 15.8 g (86%) of N-(1-formyl-6-bromo-1,2,3,4-tetrahydro-3-quinolyl)formamide, mp 174°-178° C. A sample was recrystallized from ethanol for analysis; mp 178°-181° C.

EXAMPLE 38

6-Bromo-1,2,3,4-tetrahydro-8-nitro-3-quinolinamine (compound XXIX)

A mixture of N-(1-formyl-6-bromo-1,2,3,4-tetrahydro-3-quinolyl)formamide (12.8 g, 45.2 mmol) and sodium nitrate (12.8 g, 150 mmol) in trifluoracetic acid (100 mL) was stirred at room temperature for 18 hours. The bulk of the solvent was removed under reduced pressure and the residue was partitioned between ethyl acetate and water. The ethyl acetate was washed with sodium hydroxide and water, and the ethyl acetate was removed to give 14.2 g of N-(1-formyl-6-bromo-1,2,3,4-tetrahydro-8-nitro-3-quinolyl)formamide (compound XXVIII) as a solid. This was dissolved in ethanolic hydrogen chloride (100 mL of 4.0 N), the mixture was refluxed for 1 hour, ether (200 mL) was added, and the precipitate was filtered off, washed with ether and dried to give 12.8 g (82% of 6-bromo-1,2,3,4-tetrahydro-8-nitro-3-quinolinamine dihydrochloride, mp >300° C.

EXAMPLE 39

5,6-Dihydro-4H-imidazo(4,5,1-ij)quinolin-5-amine dihydrochloride (compound 22)

A mixture of 6-bromo-1,2,3,4-tetra-8-nitrohydro-3-quinolinamine dihydrochloride (10.69 g, 0.031 mol), and 10% palladium on carbon (1.0 g) in absolute ethanol (175 mL) was hydrogenated (50 lb initial $H_2$ pressure) until the $H_2$ uptake had ceased (reaction time 1.5 hours). The mixture was filtered through celite and the solvent removed under reduced pressure. The residual foam was partitioned between ethyl acetate and 1 N sodium hydroxide solution. Evaporation of the ethyl acetate gave 5.41 g of 3,8-diamino-1,2,3,4-tetrahydroquinoline (compound XXX) as a brown oil.

This oil was dissolved in formic acid (60 mL) and stirred at 55° C. for 5 hours. The formic acid was then removed under high vacuum. The resulting oil was partitioned between ethyl acetate (400 mL) and 4 N sodium hydroxide (60 mL). The aqueous phase was extracted 5 times with ethyl acetate and the combined ethyl acetate extracts were washed with water $2\times25$ mL). The ethyl acetate was evaporated to give 5.5 g of material, a mixture of the desired product (80% and its N-formyl derivative (20%). The crude product was dissolved in methanolic HCl (150 mL) to hydrolyze the N-formyl compound. After 1.5 hours at room temperature, the precipitate which formed was filtered and washed with methanol:ether (1:3) to give 6.33 g (82%) of 5,6-dihydro-4H-imidazo(4,5,1-ij)quinolin-5-amine dihydrochloride, mp >300° C. Anal. Calcd. for $C_{10}H_{11}N_3.2HCl$: C, 48.80; H, 5.32; Cl, 28.81; N, 17.07. Found: C, 48.68; H, 5.44; Cl, 28.60; N, 16.92.

EXAMPLE 40

5,6-Dihydro-N-propyl-4H-imidazo(4,5,1-ij)quinoline-5-amine (compound 23)

Propionaldehyde (11.0 g, 0.19 mol) and sodium cyanoborohydride (0.85 g, 0.014 mol) were added at 0° C. to a stirred solution of 5,6-dihydro-4H-imidazo(4,5,1-ij)quinolin-5-amine dihydrochloride (3.0 g, 0.012 ml) in methanol (250 mL). After 20 minutes, methanolic ammonia (10 mL) was added and the solution was concentrated to an oil and partitioned between ethyl acetate and sodium hydroxide solution. The ethyl acetate phase was washed with water, evaporated, dissolved in chloroform and chromatographed on silica gel using 5% methanol:chloroform as eluant to get, as the first product eluted from the column, 0.9 g (32%) of 5,6-dihydro-N,N-dipropyl-4H-imidazo(4,5,1-ij)quinoline-5-amine.

Continued elution of the column gave 1.65 g (65%) of the monopropylamine derivative. This was dissolved in methanol and ethereal HCl and ether added. The precipitate was filtered off and recrystallized twice from methanol:ether to give 1.32 g of 5,6-dihydro-N-propyl-4H-imidazo(4,5,1-ij)quinoline-5-amine sesquihydrochloride, mp 294°-297° C. (dec). Anal. Calcd. for $C_{13}H_{17}N_3.1.5HCl$: C, 57.83; H, 6.91; Cl, 19.70; N, 15.56. Found: C, 57.84; H, 7.04; Cl, 19.46; N, 15.26.

EXAMPLE 41

5,6-Dihydro-8-methyl-N,N-dipropyl-4H-imidazo(4,5,1-ij)quinolin-5-amine (Compound 24)

This compound was prepared by following the procedure of Example 40, but substituting 5,6-dihydro-8-methyl-4H-imidazo(4,5,1-ij)quinolin-5-amine dihydrochloride for 5,6-dihydro-4H-imidazo(4,5,1-ij)quinolin-5-amine dihydrochloride. The compound was crystallized from hexane; mp 91°-94° C. Anal. Calcd. for $C_{17}H_{25}N_3O$: C, 75.23; H, 9.28; N, 15.48. Found: C75.08; H, 8.88; N, 15.67.

EXAMPLE 42

5,6-Dihydro-2-methyl-N,N-dipropyl-4H-imidazo(4,5,1-ij)quinolin-5-amine (Compound 25)

t-Butyl (8-amino-1,2,3,4-tetrahydro-3-quinolyl)carbamate (2.72 g) was treated with acetic anhydride (1.16 g) in THF (150 mL) for 2.5 hours. The reaction was evaporated and the crude product was dissolved in methanolic hydrogen chloride. After 5 hours, the solvent was removed to give 3.1 g of 5,6-dihydro-2-methyl-4H-imidazo(4,5,1-ij)quinolin-5-amine dihydrochloride.

This was converted to 5,6-dihydro-2-methyl-N,N-dipropyl-4H-imidazo(4,5,1-ij)quinolin-5-amine using the procedure of Example 40. The product was converted to the dihydrochloride salt, mp 202°-205° C. Anal. Calcd. for $C_{13}H_{17}N_3.2HCl$: C, 59.28; H, 7.91; Cl 20.59; N, 12.20. Found: C, 58.51; H, 8.02; Cl, 21.90; N, 11.41.

EXAMPLE 43 t-Butyl (6-bromo-1,2,3,4-tetrahydro-8-nitro-3-quinolinyl)carbamate (compound XXXI)

A mixture of 6-bromo-1,2,3,4-tetrahydro-8-nitro-3-quinolinamine (3.45 g, 0.01 mol), di t-butyl dicarbonate (3.0 g, 0.014 mol) and triethylamine (2.0 g, 0.02 mol) in DMF (50 mL) was stirred at room temperature for 1 hour. Water (7 mL) was slowly added to the stirred solution. The precipitate was filtered off and washed with water and air dried to give 3.7 g of bright orange solid, mp 193°-195° C. Anal. Calcd. for $C_{14}H_{18}BrN_3O_4$: C, 45.17; H, 4.87; Br, 21.47; N, 11.29. Found: C, 45.25; H, 4.97; Br, 21.34; N, 11.38.

EXAMPLE 44 t-Butyl (1,2,5,6-tetrahydro-2-oxo-4H-imidazo(4,5,1-ij)quinolin-5-yl)carbamate (compound XXXIII)

Part A. t-butyl (8-amino-1,2,3,4-tetrahydro-3-quinolinyl)carbamate

A mixture of t-butyl (6-bromo-1,2,3,4-tetrahydro-8-nitro-3-quinolinyl)-carbamate (3.72 g, 0.01 mol), absolute ethanol (150 mL) and 10% palladium on carbon (0.60 g) was hydrogenated (50 lb hydrogen pressure) for 18 hours. The mixture was filtered through celite and the solvent removed. The residual foam was partitioned between ethyl acetate and 1 N sodium hydroxide, and the ethyl acetate phase was evaporated under reduced pressure to give 2.72 g of t-butyl (8-amino-1,2,3,4-tetrahydro-3-quinolyl)carbamate (compound XXXII) as an oil.

Part B. t-Butyl (1,2,5,6-tetrahydro-2-oxo-4H-imidazo(4,5,1-ij)quinolin-5-yl)carbamate (compound XXXIII)

t-Butyl (8-amino-1,2,3,4-tetrahydro-3-quinolyl)carbamate (2.70 g) was dissolved in THF (100 mL) and stirred while a solution of phosgene in THF (20.7 mL of 0.40 M, 0.093 mol) was added. After 5 minutes, triethylamine (2.08 g, 0.020 mol) was added and the solution stirred for an additional 10 minutes. The THF was removed under reduced pressure and the material was partitioned between chloroform (250 mL) and water (20 mL). The chloroform was washed with 4N sodium hydroxide (5 mL) and evaporated. The crude material was combined with that of an earlier reaction (0.002 mol scale) and purified by chromatography on silica gel in 1% methanol:chloroform to give 2.28 g of product. Crystallization from methanol:ether (1:1) gave 1.60 g (54%) white solid, mp 235°-236° C. Anal. Calcd. for $C_{15}H_{19}N_3O_3$: C, 62.26; H, 6.62; N, 14.52. Found: C, 61.65; H, 6.94; N, 14.23.

EXAMPLE 45

5-Amino-5,6-dihydro-4H-imidazo(4,5,1-ij)quinolin-2(1H)-one (compound 26)

t-Butyl (1,2,5,6-tetrahydro-2-oxo-4H-imidazo(4,5,1-ij)quinolin-5-yl)carbamate (1.65 g, 0.057 mol) was dissolved in methanol HCl (85 mL) and stirred at room temperature for 1 hour. The solvent was removed under reduced pressure to give 1.29 g of crude product. An analytical sample was recrystallized from methanol and ether to give a pink solid, mp >300° C. Anal. Calcd. for $C_{10}H_{11}N_3O.HCl.\frac{1}{2}H_2O$: C, 51.58; H, 5.58; Cl, 15.11; N, 17.90. Found: C, 51.04; H, 5.47; Cl, 15.10; N, 17.86.

EXAMPLE 46

5-(Dimethylamino)-5,6-dihydro-4H-imidazo(4,5,1-ij)quinolin-2(1H)-one hydrochloride (compound 27)

5-Amino-5,6-dihydro-4H-imidazo-4,5,1-ij)quinolin-2(1H)-one (0.73 g, 3.2 mmol) was dissolved in 1N sodium hydroxide solution (3.2 mL). To this was added absolute ethanol (100 mL), 37% formaldehyde solution (1.3 mL), 10% palladium on carbon (0.65 g), and the mixture was hydrogenated (50 lb. initial H$_2$ pressure) until H$_2$ uptake ceased (reaction time 5 hours). The mixture was filtered through celite and the solvent removed under reduced pressure to yield a clear oil. The crude material was combined with that of a previous reaction (2.5 mmol), dissolved in chloroform and gravity filtered to remove paraformaldehyde. The compound was purified by chromatographing on silica gel in 10% methanol:chloroform to give 0.88 g (71%) of 5-(dimethylamino)-5,6-dihydro-4H-imidazo(4,5,1-ij)quinolin-2(1H)-one an oil.

The bulk of the product was converted to the hydrochloride salt, mp 220°-223° C. Anal. Calcd. for $C_{12}H_{15}N_3O.HCl.\frac{1}{2}H_2O$: C, 54.85; H, 6.52; Cl, 13.49; N, 15.99. Found: C, 54.97; H, 6.33; Cl, 13.08; N, 15.55.

EXAMPLE 47

5-(Propylamino)-5,6-dihydro-4H-imidazo(4,5,1-ij)quinolin-2(1H)-one (compound 28)

Sodium cyanoborohydride (0.17 g) was added in small portions over a 5-hour period to a stirred solution of 1.90 g (8.4 mmol) 5-amino-5,6-dihydro-4H-imidazo(4,5,1-ij)quinolin-2(1H)-one, 0.85 mL sodium methoxide and 1.5 g propionaldehyde in methanol (175 mL). Methanolic ammonia solution was added, and after 30 minutes, the solvent was evaporated. The residual oil was partitioned between ethyl acetate and water and the crude product obtained by evaporating the ethyl acetate was dissolved in chloroform and chromatographed on silica gel eluting with 2.5% methanol:chloroform to give 1.24 g (64% yield) of 5,6-dihydro-5-(propylamino)-4H-imidazo(4,5,1-ij)quinolin-2(1H)-one.

The bulk of the product was converted to the hydrochloride salt, mp >300° C. from methanol:ether. Anal. Calcd. for $C_{13}H_{17}N_3O.HCl$: C, 58.31; H, 6.77; Cl, 13.24; N, 15.69. Found: C, 58.16; H, 6.92; Cl, 13.17; N, 15.18.

EXAMPLE 48

5-(Dipropylamino)-5,6-dihydro-4H-imidazo(4,5,1-ij)quinolin-2(1H)-one (compound 29)

Propionaldehyde (12.7 g, 0.21 mol) and sodium cyanoborohydride (2.22 g, 0.035 mol) were added at 0° C. to a stirred solution of 5-amino-5,6-dihydro-4H-imidazo(4,5,1-ij)quinolin-2(1H)-one (2.70 g, 0.012 mol) and sodium methoxide (1 mL of 3.8 M) in methanol (250 mL). The solution was allowed to warm to room temperature and, after 1 hour, methanolic ammonia (10 mL) was added. The solution was stirred an additional 30 minutes and the solvent removed under reduced pressure. The mixture was dissolved in EtOAc (500 mL), washed with 4N NaOH (15 mL) and H$_2$O (2×10 mL) and evaporated. The crude product was dissolved in chloroform:methanol (2:1) and chromatographed on silica gel eluting with chloroform. The solid obtained was triturated with ether:hexane (1:1, 40 mL) and filtered to give 2.12 g (65%) of product, mp 155°-157° C. The analytical sample was recrystallized from ethyl acetate:hexane; mp 155°-158° C. Anal. Calcd. for $C_{16}H_{23}N_3O$: C, 70.29; H, 8.48; N, 15.37. Found: C, 70.36; H, 8.78; N, 15.30.

The bulk of the product was converted to the hydrochloride salt, mp 221°-224° C. (dec). Anal. Calcd. for $C_{16}H_{23}N_3O.HCl$: C, 62.02; H, 7.81; Cl, 11.44; N, 13.56. Found: C, 61.88; H, 7.79; Cl, 11.50; N, 13.48.

EXAMPLE 49

(−) 5-(Dipropylamino)-5,6-dihydro-4H-imidazo(4,5,1-ij)quinolin-2(1H)-one ((−) compound 29)

Part A. (+) and (−) t-Butoxycarbonyl N-(1,2,5,6-tetrahydro-2-oxo-4H-imidazo(4,5,1-ij)quinolin-5-yl)-L-phenylalaninamide A mixture of t-butoxycarbonyl-L-phenylalanine (2.9 g, 11 mmol), 5-amino-5,6-dihydro-4H-imidazo(4,5,1-ij)quinolin-2(1H)-one hydrochloride (2.25 g, 10 mmol), 1-hydroxybenzotriazole (1 65 g, 11 mmol), triethylamine (1.1 g, 11 mmol) and dicyclohexylcarbodiimide (3.09 g, 15 mmol) in dimethylformamide (50 mL) was stirred at room temperature for 2 hours. The solution was filtered to remove dicyclohexylurea, evaporated, and chromatographed to give, as the first product eluted from the column, 1.8 g of (+) t-butoxycarbonyl N-(1,2,5,6-tetrahydro-2-oxo-4H-imidazo(4,5,1-ij)quinolin-5-yl)-L-phenylalaninamide. This was crystallized from methanol; mp 215°-217° C.; $(\alpha)_D^{MeOH}$ +26°. Anal. Calcd. for $C_{24}H_{28}N_4O_4$: C, 66.03; H, 6.47; N, 12.84. Found: C, 66.01; H, 6.54; N, 13.01.

Continued elution of the column gave 1.9 g of (−) t-butoxycarbonyl N-(1,2,5,6-tetrahydro-2-oxo-4H-imidazo(4,5,1-ij)quinolin-5-yl)-L-phenylalaninamide.

Part B. (−) 5-amino-5,6-dihydro-4H-imidazo(4,5,1-ij)quinolin-2(1H)-one (−) t-Butoxycarbonyl N-(1,2,5,6-tetrahydro-2-oxo-4H-imidazo(4,5,1-ij)quinolin-5-yl)-L-phenylalaninamide (1.8 g) was stirred in ethanolic hydrogen chloride (50 mL of 4.0 N) for 1 hour. The solvent was removed and the residual oil was partitioned between chloroform and sodium hydroxide solution. Evaporation of the chloroform gave 1.4 g of (−) N-(1,2,5,6-tetrahydro-2-oxo-4H-imidazo(4,5,1-ij)quinolin-5-yl)phenylalaninamide. This was dissolved in acetonitrile:THF (30 mL of 1:1) and phenyl isothiocycanate (675 mg, 5 mmol) was added. After 1 hour, the solvents were removed and the residual oil was chromatographed on silica gel using chloroform as the initial eluant. Elution of the column with 5% methanol:chloroform gave 1.8 g of (−) N-((phenylamino)thiocarbonyl)-N-(1,2,5,6-tetrahydro-2-oxo-4H-imidazo(4,5,1-ij)quinolin-5-yl)phenylalaninamide. This was dissolved in trifluoroacetic acid (25 mL). After 1 hour the solvent was removed and the residue was dissolved in methanol (5 mL). Ether (50 mL) was added, the solution was cooled to −10° C., and the precipitate was filtered off, washed with ether, and air dried to give 1.2 g of (−) 5-amino-5,6-dihydro-4H-imidazo(4,5,1-ij)quinolin-2(1H)-one trifluoroacetate, mp 247° C. (dec). $(\alpha)_D^{MeOH}$ −18°. Anal. Calcd. for $C_{10}H_{11}N_3O \cdot C_2HF_3O_2$: C, 47.53; H, 3.99; F, 18.80; N, 13.97. Found: C, 47.31; H, 4.26; F, 17.37; N, 13.48.

Part C. (−) 5-(Dipropylamino)-5,6-dihydro-4H-imidazo(4,5,1-ij)quinolin-2(1H)-one This was prepared following the procedure of Example 47, but using (−) 5-amino-5,6-dihydro-4H-imidazo(4,5,1-ij)quinolin-2(1H)-one trifluoroacetate in place of 5amino-5,6-dihydro-4H-imidazo(4,5,1-ij)quinolin-2(1H)-one. The hydrochloride salt of the product crystallized from methanol:ether as a hemihydrate (2.89% water content) with an indefinite melting point; $(\alpha)_D^{MeOH}$ −16.5°. Anal. Calcd. for $C_{16}H_{23}N_3O \cdot HCl \cdot \frac{1}{2}H_2O$: C, 62.02; H, 7.81; N, 13.56; Cl, 11.44. Found: C, 61.88; H, 7.79; N, 13.48; Cl, 11.50. The compound was also converted to the hydrobromide salt which was obtained as a monohydrate, mp 190°–192° C. from methanol/ether.

EXAMPLE 50

(+) 5-(Dipropylamino)-5,6-dihydro-4H-imidazo(4,5,1-ij)quinolin-2(1H)-one hydrochloride This was prepared from (+) t-butoxycarbonyl N-(1,2,5,6-tetrahydro-2-oxo-4H-imidazo(4,5,1-ij)quinolin-5-yl)-L-phenylalaninamide using the procedures described in Example 49, parts B and C. The hydrochloride salt of the product crystallized from methanol:ether as a hydrate (0.99% water content) with an indefinite melting point; $(\alpha)_D^{MeOH}$ +16.5°. Anal. Calcd. for $C_{16}H_{23}N_3O \cdot HCl \cdot \frac{1}{4}H_2O$: C, 61.13; H, 8.01; Cl, 11.28; N, 13.37. Found: C, 61.17; H, 8.08; Cl, 11.12; N, 13.35.

EXAMPLE 51

5-(Dipropylamino)-5,6-dihydro-1-methyl-4H-imidazo(4,5,1-ij)quinolin-2(1H)-one (compound 30)

Potassium hydride (0.28 g of a 35% by wt. mineral oil dispersion, washed with ether to remove oil, 2.7 mmol) in dry THF was added to a stirred solution of 5-dipropylamino)-5,6-dihydro-4H-imidazo(4,5,1-ij)quinolin-2(1H)-one (0.60 g, 2.2 mmol) in dry THF (25 mL). Methyl iodide (0.31 g, 2.2 mmol) in dry THF was then added. After stirred at room temperature for 18 hours, methanol was slowly added to the solution. The solvent was then removed under reduced pressure and the material dissolved in methanol:chloroform (1:1) and chromatographed on silica gel using chloroform as eluant to give 0.50 g (79% yield) of a yellow solid. The product was recrystallized twice from hexane to give 0.28 g (44%) of 5-(dipropylamino)-5,6-dihydro-1-methyl-4H-imidazo(4,5,1-ij)quinolin-2(1H)-one, mp 83°–85° C. Anal. Calcd. for $C_{17}H_{25}N_3O$: C, 71.04; H, 8.77; N, 14.62. Found: C, 71.25; H, 8.91; N, 14.74.

EXAMPLE 52

5-(Dimethylamino)-5,6-dihydro-1-methyl-4H-imidazo(4,5,1-ij)quinolin-2(1H)-one (compound 31)

This compound was prepared by following the procedure of Example 51, but substituting 5-(dimethylamino)-5,6-dihydro-4H-imidazo(4,5,1-ij)quinolin-2(1H)-one for 5-(dipropylamino)-5,6-dihydro-4H-imidazo(4,5,1-ij)quinolin-2(1H)-one.

The product was converted to the hydrochloride salt which was crystallized from methanol:ether; mp 268°–271° C. Anal. Calcd. for $C_{13}H_{17}N_3O \cdot HCl$: C, 58.31; H, 6.77; Cl, 13.24; N, 15.69, Found: C, 58.40; H, 6.92; Cl, 13.05; N, 15.33.

EXAMPLE 53

5-(Dimethylamino)-5,6-dihydro-8-methyl-4H-imidazo(4,5,1-ij)quinolin-2(1H)-one (compound 32)

This compound was prepared by following the procedure of Example 46, but substituting 5-amino-5,6-dihydro-6-methyl-4H-imidazo(4,5,1-ij)quinolin-2(1H)-one for 5-amino-5,6-dihydro-4H-imidazo-(4,5,1-ij)quinolin-2(1H)-one.

The product was converted to the hydrochloride salt which was crystallized from methanol:ether; mp 281°–284° C. Anal. Calcd. for $C_{13}H_{17}N_3O \cdot HCl$: C, 58.31; H, 6.77; Cl, 13.24; N, 15.69. Found: C, 58.00; H. 7.03; Cl, 12.94; N, 15.44.

EXAMPLE 54

6-Bromo-1,2,3,4-tetrahydro-8-nitro-N,N-dipropyl-3-quinolinamine (compound XXXIa)

A mixture of 6-bromo-1,2,3,4-tetrahydro-8-nitro-3-quinolinamine dihydrochloride (11.5 g, 0.033 mol), idopropane (21 g, 0.12 mol) and anhydrous sodium carbonate (20 g, 0.19 mol) in dimethylformamide (100 mL) was stirred at 100° C. for 5 hours. The solution was then evaporated, partitioned between ethyl acetate and water, and the ethyl acetate was evaporated to give a red oil. This was chromatographed on silica gel to give 8.2 g of 6-bromo-1,2,3,4-tetrahydro-8-nitro-N,N-dipropyl-3-quinolinamine. The product was crystallized from ethyl acetate:hexane to give 7.6 g of product, mp 79°–81° C. Anal. Calcd. for $C_{15}H_{22}BrN_3O_2$: C, 50.57; H, 6.23; Br, 22.43; N, 11.79. Found: C, 50.59; H, 6.27; Br, 22.53; N, 11.69.

Continued elution of the column afforded 1.5 g of 6-bromo-1,2,3,4-tetrahydro-8-nitro-N-propyl-3-quinolinamine as an oil.

EXAMPLE 55

6-Bromo-1,2,3,4-tetrahydro-N,N-dimethyl-8-nitro-3-quinolinamine (compound XXXIb)

A mixture of 6-bromo-1,2,3,4-tetrahydro-8-nitro-3-quinolinamine (1.5 g, 5.5 mol), 37% aqueous formaldehyde (1.8 mL) and formic acid (10 mL) was heated at 100° C. for 1 hour. The solution was then evaporated, partitioned between ethyl acetate (200 mL) and 4 N sodium hydroxide solution (10 mL), and the ethyl acetate was evaporated to give a red oil. This was chromatographed on silica gel to give 1.58 g of 6-bromo-1,2,3,4-tetrahydro-8-nitro-N,N-dipropyl-3-quinolinamine. The product was crystallized from ethyl acetate:hexane; mp 88°–91° C. Anal. Calcd. for $C_{11}H_{14}BrN_3O_2$: C, 44.01; H, 4.70; Br, 26.62; N, 14.00. Found: C, 44.04; H, 4.89; Br, 26.62; N, 13.97.

EXAMPLE 56

5-(Dipropylamino)-5,6-dihydro-4H-imidazo(4,5,1-ij)quinolin-2(1H)-thione (Compound 33)

Part A. 1,2,3,4-Tetrahydro-$N^3$,$N^3$-dipropyl-3,8-quinolinediamine (compound XXXVb)

A mixture of 6-bromo-1,2,3,4-tetrahydro-8-nitro-N,N-dipropyl-3-quinolinamine (2.7 g) and 10% palladium charcoal (0.5 g) in ethanol (150 mL) was hydrogenated for 18 hours. The solution was filtered and the ethanol evaporated to give 1.9 g of 1,2,3,4-tetrahydro-$N^3$,$N^3$-dipropyl-3,8-quinolinediamine as an oil.

Part B. 5-(Dipropylamino)-5,6-dihydro-4H-imidazo(4,5,1-ij)quinolin-2(1H)-thione

Di (2-pyridyl)thiocarbonate (1.6 g, 7.2 mmol) was added to a stirred solution of 1,2,3,4-tetrahydro-$N^3$,$N^3$-dipropyl-3,8-quinolinediamine (1.6 g, 6.7 mmol) in THF (50 mL). The solution was stirred for 1 hour, evaporated, and partitioned between chloroform and water. The chloroform phase was evaporated and chromatographed on silica gel using ethyl acetate:hexane (1:9) as the initial eluant to give 1.6 g of product. Crystallization from cyclohexane gave 1.3 g (67% of 5-(dipropylamino)-5,6-hydro-4H-imidazo(4,5,1-ij)quinolin-2(1H)-thione, mp 150°-151° C. Anal. Calcd. for $C_{16}H_{23}N_3S$: C, 66.39; H, 8.01; N, 14.52; S, 11.08. Found: C, 66.50; H, 8.18; N, 14.56; S, 11.02.

EXAMPLE 57

5,6-Dihydro-2-methylthio-N,N-dipropyl-4H-imidazo(4,5,1-ij)quinolin-5-amine (compound 34)

This compound was prepared using the procedure of Example 51, but substituting 5-(dipropylamino)-5,6-dihydro-4H-imidazo(4,5,1-ij)quinolin-2(1H)-thione for 5-(dipropylamino)-5,6-dihydro-4H-imidazo(4,5,1-ij)quinolin-2(1H)-one. The product was crystallized from pentane; mp 49°-52° C. Anal. Calcd. for $C_{17}H_{25}N_3S$: C, 67.28; H, 8.30; N, 13.85; S, 10.57. Found: C, 67.57; H, 8.27; N, 14.00; S, 10.44.

EXAMPLE 58

5,6-Dihydro-$N^5$,$N^5$-dipropyl-4H-imidazo(4,5,1-ij)quinoline-2,5-diamine (compound 35)

This compound was prepared using the procedure of Example 56 part B, but substituting cyanogen bromide for di (2-pyridyl)thiocarbonate. The product was purified by chromatography and tritutated with ether; mp 160°-170° C. Anal. Calcd. for $C_{16}H_{24}N_4$: C, 70.55; H, 8.88; N, 20.57. Found: C, 68.96; H, 9.03; N, 20.57.

EXAMPLE 59

5,6-Dihydro-$N^2$-methyl-$N^5$,$N^5$-dipropyl-4H-imidazo(4,5,1-ij)quinoline-2,5diamine (compound 36)

This compound was prepared using the procedure of Example 51, but substituting 5,6-dihydro-$N^5$,$N^5$-dipropyl-4H-imidazo(4,5,1-ij)quinoline-2,5-diamine for 5-(dipropylamino)-5,6-dihydro-4H-imidazo(4,5,1-ij)quinolin-2(1H)-one. The product was separated by chromatography from the accompanying 5,6-dihydro-1-methyl-$N^5$,$N^5$-dipropyl-4H-imidazo( 4,51-ij)quinoline-2,5-diamine.

EXAMPLE 60

5-(Dipropylamino)-5,6-dihydro-4H-imidazo(4,5,1-ij) quinolin-2-yl)cyanamide (compound 37)

This compound was prepared using the procedure of Example 56 part B, but substituting diphenyl cyanocarbonimidate for di (2-pyridyl)thiocarbonate.

EXAMPLE 61

5,6-Dihydro-N,N-dipropyl-1H,4H-thiadiazolo(4,3,2-ij)quinoline-5-amine 2,2-dioxide (compound 38)

This compound was prepared using the procedure of Example 56 part B, but substituting sulfamide for di (2-pyridyl)thiocabonate and carrying the reaction out at 150° C. in absence of solvent.

EXAMPLE 62

1,2,6,7-Tetrahydro-6-(dipropylamino)-3H,5H-pyrido(1,2,3-de)quinoxalin-3-one (compound 39)

This compound was prepared using the procedure of Example 56, but substituting ethyl bromoacetate for di (2-pyridyl)thiocarbonate and carrying the reaction out at the reflux temperature. The crude product was chromatographed to give, as the major product and first compound eluted from the column, 1,2,6,7-tetrahydro-6-(dipropylamino)-3H,5H-pyrido(1,2,3-de)quinoxalin-3-one. The product was crystallized from ethyl acetate:-hexane; mp 97°-99° C. Anal Calcd. for $C_{17}H_{25}N_3O$: C, 71.04; H, 8.77; N, 14.62. Found: C. 71.20; H, 8.90; N, 14.85.

Continued elution of the column have a small amount of 1,2,6,7-tetrahydro-6-(dipropylamino)-3H,5H-pyrido(1,2,3-de)quinoxalin-2-one.

EXAMPLE 63

1,2,6,7-Tetrahydro-6-(dipropylamino)-3H,5H-pyrido(1,2,3-de)quinoxalin-2-one (compound 40)

This compound was prepared using the procedure of Example 56, but substituting chloroacetic anhydride for di (2-pyridyl)thiocarbonate. The initially formed $N^8$-(chloroacetyl)-1,2,3,4-tetrahydro-$N^3$,$N^3$-dipropyl-3,8-quinolinediamine was heated at 150° C. in DMF to effect cyclization to 1,2,6,7-tetrahydro-6-(dipropylamino)-3H,5H-pyrido (1,2,3-de)quinoxalin-2-one which was thereby obtained as the hydrochloride salt which was crystallized from methanol:ether; mp 250°-255° C. (dec). Anal. Calcd. for $C_{17}H_{25}N_3O \cdot HCl$: C, 63.04; H, 8.09; Cl, 10.95; N, 12.98. Found: C, 62.39; H, 8.34; Cl, 10.85; N, 12.84.

EXAMPLE 64

6,7-Dihydro-6-(dipropylamino)-3H,5H-pyrido(1,2,3-de)quinoxalin-3-one (compound 41)

This compound was prepared using the procedure of Example 56, but substituting butyl glyoxylate for di (2-pyridyl)thiocarbonate and carrying the reaction out at the reflux temperature.

The bulk of the product was converted to the p-toluenesulfonate salt, mp 188°-190° C. from methanol:ether.

EXAMPLE 65

6,7-Dihydro-6-(dipropylamino)-1H,5H-pyrido(1,2,3-de)quinoxalin-2,3-dione (compound 42)

This compound was prepared using the procedure of Example 56, but substituting ethyl oxalyl chloride for di (2-pyridyl)thiocarbonate and carrying the reaction out at the reflux temperature. The product was crystallized from ethyl acetate:hexane; mp 166°-168° C. Anal. Calcd. for $C_{17}H_{23}N_3O_2$: C, 67.75; H, 7.69; N, 13.94. Found: C, 67.66; H, 7.96; N, 13.80.

The bulk of the product was converted to the hydrochloride salt which was crystallized from methanol:ether; mp 250°-255° C. (dec).

EXAMPLE 66

5-(Dimethylamino)-5,6-dihydro-4H-imidazo(4,5,1-ij)quinolin-2(1H)-thione (compound 43)

Part A. 1,2,3,4-Tetrahydro-$N^3$,$N^3$-dimethyl-3,8-quinolinediamine (compound XXXVb)

A mixture of 6-bromo-1,2,4-tetrahydro-8-nitro-N,N-dimethyl-3-quinolinamine (1.15 g, 3.8 mmol) and 10% palladium charcoal (0.5 g) in ethanol (150 mL) was hydrogenated for 18 hours. The solution was filtered and the ethanol evaporated to give 0.73 g of 1,2,3,4-tetrahydro-$N^3$,$N^3$-dimethyl-3,8-quinolinedimaine as an oil.

Part B. 5-(Dimethylamino)-5,6-dihydro-4H-imidazo(4,5,1-ij)quinolin-2(1H)-thione

Di (2-pyridyl)thiocarbonate (0.92 g, 4.0 mmol) was added to a stirred solution of 1,2,3,4-tetrahydro-$N^3$,$N^3$-dimethyl-3,8-quinolinedimaine (0.73 g, 3.8 mmol) in THF (50 mL). The solution was stirred for 1 hour, evaporated, and partitioned between chloroform and water. The chloroform phase was evaporated and chromatographed on silica gel using ethyl acetate:hexane (1:9) as the initial eluant to give 0.68 g of product. Crystallization from cyclohexane gave 0.60 g of 5-(dimethylamino)-5,6-dihydro-4H-imidazo(4,5,1-ij)quinolin-2(1H)-thione, mp 203°-205° C. Anal. Calcd. for $C_{12}H_{15}N_3S$: C, 61.77; H, 6.48; N, 18.01; S, 13.74. Found: C, 61.77; H, 6.53; N, 17.73; S.

EXAMPLE 67

Alternate synthesis of 1,2,3,4-Tetrahydro-$N^3$,$N^3$-dimethyl-3,8-quinolinediamine (compound XXXVb)

Part A. Diethyl (formylamino)(2-nitrophenyl)methyl)propanedioate

Diethyl (formylamino)malonate (20.3 g, 0.1 mol) was added to a stirred solution of sodium ethoxide (250 mL of 0.4M). 2-Nitrobenzylchloride (17.2 g, 0.1 mol) was added, the mixture was refluxed for 2 hours and the solvent was then removed under reduced pressure. The material was partitioned between ethyl acetate and water, the ethyl acetate was separated and evaporated to give 40.3 g of crude product. The compound was crystallized from ethyl acetate:hexane to give 25.5 g of diethyl (formylamino)(2-nitrophenyl)methyl)propanedioate; mp 129°-132° C.

Part B. Ethyl 3-(formylamino)-1,2,3,4-tetrahydro-2-oxo-3-quinolinecarboxylate

A mixture of diethyl (formylamino)(2-nitrophenyl)methyl)propanedioate (8.54 g, 0.025 mol) and 10% palladium on carbon (2.0 g) in absolute ethanol (200 mL) was hydrogenated (50 lb initial $H_2$ pressure) until hydrogen uptake ceased. The mixture was filtered through celite and refluxed for 2 hours to achieve cyclization. The solvent was removed under reduced pressure to give 6.6 g of product which was crystallized from methanol to give 5.0 g of white crystals. mp 187°-190° C. Anal. Calcd. for $C_{13}H_{14}N_2O_4$: C, 59.53; H, 5.38; N, 10.68. Found: C, 59.77; H, 5.36; N, 10.75.

Part C. 3-(Formylamino)-3,4-dihydro-2(1H)quinolinone

Sodium hydroxide (50 mL of 4.0N, 0.20 mol) was added to a stirred solution of ethyl 3-(formylamino)-1,2,4,-tetrahydro-2-oxo-3-quinolinecarboxylate (11.3 g, 0.043 mol) in methanol (250 mL). After 30 minutes, a white precipitate appeared and, after 45 minutes water (50 mL) was added to the reaction. After refluxing overnight, hydrochloric acid (50 mL of 4.0N, 0.20 mol) was added and the solvents were removed under reduced pressure. The residual solid was refluxed in ethanol (200 mL) for 1 hour, filtered to remove salt, and cooled to afford 6.8 g of product, mp 197°-200° C. Anal. Calcd. for $C_{10}H_{10}N_2O_2$: C, 63.15; H, 5.30; N, 14.73. Found: C, 63.03; H, 5.37; N, 14.71.

Part D. 3-(Formylamino)-6-bromo-3,4-dihydro-8-nitro-2(1H)quinolinone

Bromine (16.0 g, 0.1 mol) was added to a stirred solution of 3-(formylamino)-3,4-dihydro-2(1H)quinolinone (19.0 g, 0.1 mol) and anhydrous sodium acetate (12.7 g, 0.2 mol) in acetic acid (500 mL). After 1 hour, water (1.5 L) was added and the precipitate was filtered off and air dried to give 17.8 g of 3-(formylamino)-6-bromo-3,4-dihydro-2(1H)quinolinone, mp 275°-282° C. (dec). This was dissolved in trifluoracetic acid (300 mL) and sodium nitrate (9.0 g) was added to the stirred solution. After 1 hour, water was added and the precipitate was filtered off and air dried to give 18.2 g of 3-(formylamino)-6-bromo-3,4-dihydro-8-nitro-2(1H)quinolinone, mp 232°-235° C.

Part E. 3-(Amino)-6-bromo-3,4-dihydro-8-nitro-2(1H)quinolinone

This compound was prepared using the procedure of Example 9 part A, but substituting 3-(formylamino)-6-bromo-3,4-dihydro-8-nitro-2(1H) quinolinone for N-(2,3,6,7-tetrahydro-3-oxo-1H,5H-benzo(ij)quinolizin-2-yl)-formamide.

Part F. 3-(Dimethylamino)-6-bromo-3,4-dihydro-8-nitro-2(1H)quinolinone

This compound was prepared using the procedure of Example 55, but substituting 3-(formylamino)-6-bromo-3,4-dihydro-8-nitro-2(1H)quinolinone for 6-bromo-1,2,3,4-tetrahydro-8-nitro-3-quinolinamine. The product was crystallized from ethyl acetate; mp 162°-165° C.

Part G. 3,8-Diamino-3,4-dihydro-$N^3$,$N^3$-dimethyl-2(1H)quinolinone

This compound was prepared using the procedure of Example 56 part A, but substituting 3-(dimethylamino)-6-bromo-3,4-dihydro-8-nitro-2(1H)quinolinone for 6-bromo-1,2,3,4-tetrahydro-8-nitro-N,N-dipropyl-3-quinolinamine.

Part H. 1,2,3,4-Tetrahydro-$N^3$,$N^3$-dimethyl-3,8-quinolinediamine

This compound was prepared using the procedure of Example 14, but substituting 3,8-diamino-3,4-dihydro-$N^3$,$N^3$-dimethyl-2(1H)quinolinone for N-(2,3,6,7-tetrahydro-3-oxo-1H,5H-benzo(ij)quinolizin-2-yl)propanamide.

EXAMPLE 68

5,6-Dihydro-N,N-dimethyl-2-methylthio-4H)imidazo(4,5,1-ij)quinoline-5-amine (compound 44)

This compound was prepared using the procedure of Example 51, but substituting 5-(dimethylamino)-5,6-dihydro-4H-imidazo(4,5,1-ij)quinolin-2(1H)-thione for 5-(dipropylamino)-5,6-dihydro-4H-imidazo(4,5,1-ij)quinolin-2(1H)-one. The product was crystallized from ethyl acetate:hexane; mo 84°-86° C. Anal. Calcd. for $C_{13}H_{17}N_3S$: C, 63.12; H, 6.93; N, 16.99; S, 12.96. Found: C, 63,08; H, 7.02; N, 16.97; S, 12.82.

EXAMPLE 69

5,6-Dihydro-$N^5$, $N^5$-dimethyl-4H-imidazo)4,5,1ij)quinoline- 2,5-diamine (compound 45)

This compound was prepared using the procedure of Example 66, but substituting cyanogen bromide for di (2-pyridyl)thiocarbonate.

EXAMPLE 70

5,6-Dihydro-N,N-dimethyl-4H-thiodiazolo(4,3,2-ij)quinoline-5-amine 2,2-dioxide (Compound 46)

This compound was prepared using the procedure of Example 66, but substituting sulfamide for di (2-pyridyl)thiocarbonate and carrying the reaction out at 150° C. in absence of solvent.

EXAMPLE 71

1,2,6,7-Tetrahydro-6-(dimethylamino)-3H,5H-pyrido(1,2,3-de)quinoxalin-3-one (compound 47)

This compound was prepared using the procedure of Example 66, but substituting ethyl bromoacetate for di (2-pyrridyl)thiocarbonate and carrying the reaction out at the reflux temperature.

EXAMPLE 72

1,2,6,7-Tetrahydro-6-(dimethylamino)-3H,5H-pyrido(1,2,3-de)quinoxalin-2-one (compound 48)

This compound was prepared using the procedure of Example 66, but substituting chloroacetic anhydride for di (2-pyridyl)thiocarbonate and cyclizing the initially formed $N^8$-(chloroacetyl)-1,2,3,4-tetrahydro-$N^3$,$N^3$-dimethyl-3,8-quinolinediamine by heating at 150°0 C. in DMF.

EXAMPLE 73

6,7-Dihydro-6-(dimethylamino)-3H,5H-pyrido[1,2,3-de)quinoxalin-3-one (compound 49)

This compound was prepared using the procedure of Example 66, but substituting butyl glyoxylate for di (2-pyridyl)thiocarbonate and carrying the reaction out at the reflux temperature.

EXAMPLE 74

6,7-Dihydro-6-(dimethylamino)-1H,5H-pyrido(1,2,3-di)quinoxalin-2,3-dione (compound 50)

This compound was prepared using the procedure of Example 66, but substituting ethyl oxalyl chloride for di (2-pyridyl)thiocarbonate and carrying the reaction out at the reflux temperature.

EXAMPLE 75

Alternate synthesis of 5-(dipropylamino)5,6-dihydro4H-imidazo(4,5,1-ij)quinolin-2(1H)-one (compound 29)

Part A. 4-Methyl-1H-benzimidazolidinone 1,1-Carbonyldiimidazole (30.5 g, 0.19 mol) was added, with cooling, to a stirred solution of 3-methyl-1,2-benzenediamine (22.98 g, 0.19 mol) in dimethylformamide (200 mL) and the mixture was heated at 100° C. for 1 hour. The solvent was removed under reduced pressure until solid began to appear. Water (200 mL) was slowly added, with stirring, to precipitate the desired product. The precipitate was filtered off and air-dried overnight to give 26.28 g brown solid, mp >280° C., which was used without further purification.

Part B. 2-Chloro-4-methyl-1H-benzimidazole

Hydrogen chloride gas was bubbled through a stirred mixture of 4-methyl-1H-benzimidazolidone (5 g, 0.034 mol) in phosphorus oxychloride (50 mL) for 1 hour at 120° C. The solvent was removed and the resulting solid was dissolved in water (50 mL). Ammonium hydroxide (20 mL) was carefully added until the mixture was basic. The aqueous phase was then extracted with chloroform, filtered through celite, and evaporated to give 5.2 g, of brown oil. The product was chromatographed on silica gel in chloroform, and was eluted with 1% methanol:chloroform to give 3.96 g of brown oil. Crystallization from ethyl acetate:hexane gave 2.72 g of brown crystals, mp 137.5°-139.5° C.

Part C. Methyl 2-chloro-4-methyl-1H-benzimidzole-1-carboxylate

Potassium hydride (0.85 g of 35% in oil, washed with ether to remove oil, 7.4 mmol) was added to a stirred solution of 2-chloro-4-methyl-1H-benzimidazole (1.23 g, 7.4 mmol) in THF (25 mL). Methyl chloroformate (0.7 g, 7.4 mmol) was added and the reaction was stirred 10 minutes. The solvent was removed and the material was partitioned between ethyl acetate and water. Evaporation of the organic layer gave 1.68 g of which solid. Crystallization from hexane gave 1.42 g of white crystals, mp 90°-91° C. Anal. Calcd. for $C_{10}H_9ClN_2O_2$: C, 53.47; H, 4.04; Cl, 15.78; N, 12.47. Found: C, 53.63; H, 4.11; Cl, 15.81; N, 12.45.

Part D. Methyl 4-(bromomethyl)-2-chloro-1H-benzimidazole-1-carboxylate

A mixture of methyl 4-methyl-2-chloro-1H-benzimidazole-1-carboxylate (17.5 g, 0.078 mol), N-bromosuccinimide (13.9 g, 0.078 mol) and benzoyl peroxide (2.0 g) in carbon tetrachloride (175 mL) was stirred at reflux for 2 hours. The solution was cooled, filtered to remove succinimide by-products, evaporated and crystallized from ethyl acetate:hexane to give 17.1 g of methyl-4-(bromomethyl)-2-chloro-1H-benzimidazole-1-carboxylate as a pale yellow solid.

Part E. 2-Chloro-5,6-dihydro-N,N-dipropyl-4H-imidazo)4,5,1-ij)quinoline-5-amine (compound 51)

This compound was prepared using the procedure of Example 18, but substituting methyl-4-(bromomethyl)-2-chloro-1H-benzimidazole-1-carboxylate for methyl-4-(bromomethyl)-1H-benzimidazole-1-carboxylate. The bulk of the product was converted to the dihydrochloride salt, mp 165°-170° C.

Part F. 5-(Dipropylamino)-5,6-dihydro-4H-imidazo(4,5,1-ij)quinoline-2(1H)-one (compound 29)

2-Chloro-5,6-dihydro-N,N-dipropyl-4H-imidazo(4,5,1-ij)quinolin-5-amine was refluxed in acetic acid for 1 hour. The solvent was removed and the residue was partitioned between ethyl acetate and sodium hydroxide solution. Evaporation of the ethyl acetate afforded 5-(dipropylamino)-5,6-dihydro-4H-imidazo(4,5,1-ij)quinoline-2(1H)-one.

EXAMPLE 76

1-(1,2,5,6-Tetrahydro-2-oxo-4H-imidazo(4,5,1-ij)quinolin-5-yl)pyrrolidine (compound 52)

This compound was prepared by following the procedure of Example 44 part B, but substituting 1-(8-amino-1,2,3,4-tetrahydro-3-quinolyl)pyrrolidine for t-butyl (8-amino-1,2,3,4-tetrahydro-3-quinolyl)carbamate.

EXAMPLE 77

1-(1,2,5,6-Tetrahydro-2-oxo-4H-imidazo(4,5,1-ij)quinolin-5-yl)piperidine (compound 53)

This compound was prepared by following the procedure of Example 44 part B, but substituting 1-(8-amino-1,2,3,4-tetrahydro-3-quinolyl)piperidine for t-butyl (8-amino-1,2,3,4-tetrahydro-3-quinolyl)carbamate.

EXAMPLE 78

4-(1,2,5,6-Tetrahydro-2-oxo-4H-imidazo(4,5,1-ij)quinolin-5-yl)morpholine (compound 54)

This compound was prepared by following the procedure of Example 44 part B, but substituting 1-(8-amino-1,2,3,4-tetrahydro-3-quinolyl)morpholine for t-butyl (8-amino-1,2,3,4-tetrahydro-3-quinolyl)carbamate.

EXAMPLE 79

1-(2,2,5,6-Tetrahydro-2-oxo-4H-imidazo(4,5,1-ij)quinolin-5-yl)imidazole (compound 55)

This compound was prepared by following the procedure of Example 44 part B, but substituting 1-(8-amino-1,2,3,4-tetrahydro-3-quinolyl)imidazole for t-butyl (8-amino-1,2,3,4-tetrahydro-3-quinolyl)carbamate.

EXAMPLE 80

1-(1,2,5,6-Tetrahydro-2-oxo-4H-imidazo(4,5,1-ij)quinolin-5-yl-4-methylpiperazine (compound 56)

This compound was prepared by following the procedure of Example 44 part B, but substituting 1-(8-amino-1,2,3,4-tetrahydro-3-quinolyl)-4-methylpiperazine for t-butyl (8-amino-1,2,3,4-tetrahydro-3-quinolyl)-carbamate.

EXAMPLE 81

5-((Phenylmethyl)methylamino)-5,6-dihydro-4H-imidazo(4,5,1-ij)quinoline-2(1H)-one (compound 57)

This compound was prepared by following the procedure of Example 44 part B, but substituting 1,2,3,4-tetrahydro-$N^3$-methyl-$N^3$-(phenylmethyl)quinoline-3,8-diamine for t-butyl (8-amino-1,2,3,4-tetrahydro-3-quinolyl)carbamate. The bulk of the product was converted to the hydrochloride salt, mp 145°–149° C. from methanol/ether.

EXAMPLE 82

5-(Dipropylamino)-7-chloro-5,6-dihydro-4H-imidazo(4,5,1-ij)quinolin-2(1H)-one (compound 58)

This compound was prepared by following the procedure of Example 44 part B, but substituting 5-chloro-1,2,3,4-tetrahydro-$N^3$,$N^3$-dipropyl-3,8-quinolinediamine for t-butyl (8-amino-1,2,3,4-tetrahydro-3-quinolyl)carbamate.

EXAMPLE 83

5-(Dipropylamino)-5,6-dihydro-7-methyl-4H-imidazo(4,5,1-ij)quinoline-2(1H)-one (compound 59)

This compound was prepared by following the procedure of Example 44 part B, but substituting 1,2,3,4-tetrahydro-5-methoxy-$N^3$,$N^3$-dipropyl-3,8-quinolinediamine for t-butyl (8-amino-1,2,3,4-tetrahydro-3-quinolyl)carbamate.

EXAMPLE 84

5-(Dipropylamino)-5,6-dihydro-8-methoxy-4H-imidazo(4,5,1-ij)quinolin-2(1H)-one (compound 60)

This compound was prepared by following the procedure of Example 44 part B, but substituting 1,2,3,4-tetrahydro-6-methoxy-$N^3$,$N^3$-dipropyl-3,8-quinolinediamine for t-butyl (8-amino-1,2,3,4-tetrahydro-3-quinolyl)carbamate.

EXAMPLE 85

5-(Dipropylamino)-5,6-dihydro-9-methoxy-4H-imidazo(4,5,1-ij)quinoline-2(1H)-one (compound 61)

This compound was prepared by following the procedure of Example 44 part B, but substituting 1,2,3,4-tetrahydro-7-methoxy-$N^3$,$N^3$-dipropyl-3,8-quinolinediamine for t-butyl (8-amino-1,2,3,4-tetrahydro-3-quinolyl)carbamate.

EXAMPLE 86

5-(Dimethylamino)-5,6-dihydro-8-methoxy-4H-imidazo(4,5,1-ij)quinoline-2(1H)-one (compound 62)

This compound was prepared by following the procedure of Example 44 part B, but substituting, 1,2,3,4-tetrahydro-6methoxy-$N^3$,$N^3$-dimethyl- 3,8-quinolinediamine for t-butyl (8-amino-1,2,3,4-tetrahydro-3-quinolyl)carbamate.

EXAMPLE 87

5-(Dimethylamino)-5,6-dihydro-4H-imidazo(4,5,1-ij)quinolin-8-ol (compound 63)

This compound was prepared by following the procedure of Example 32, but substituting 5-(dimethylamino)-5,6-dihydro-8-methoxy-4H-imidazo(4,5,1-ij)quinoline-2(1H)-one for 5,6-dihydro-7-methoxy-N,N-dipropyl-4H-imidazo(4,5,1-ij)quinolin-5-amine.

EXAMPLE 88

5,6-Dihydro-6-methyl-N,N-dimethyl-4H-imidazo(4,5,1-ij)quinoline-5-amine (compound 64)

Part A. 4-Ethyl-1H-benzimidazole

This compound was prepared following the procedure of Example 16, but substituting 4-bromo-2-ethyl-6-nitroaniline for 2-methyl-6-nitroaniline.

Part B. t-Butyl 4-(1-bromoethyl)-1H-benzimidazole-1-carboxylate

This compound was prepared following the procedure of Example 17, but substituting 4-ethyl-1H-benzimidazole for 4-methyl-1H-benzimidazole.

Part C. 5,6-Dihydro-6-methyl-N,N-dimethyl-4H-imidazo(4,5,1-ij)quinolin-5-amine

This compound, a mixture of diasteromers, was prepared following the procedure of Example 19, but substituting t-butyl 4-(1-bromomethyl)-1H-benzimidazole-1-carboxylate for t-butyl 4-(1-bromomethyl)-1H-benzimidazole-1-carboxylate.

EXAMPLE 89

5,6-Dihydro-6-methyl-N,N-dipropyl-4H-imidazo(4,5,1-ij)quinolin-5-amine (compound 65)

This compound, a mixture of diasteromers, was prepared following the procedure of Example 88 part C, but substituting methyl benzyl (dipropylamino)malonate for methyl benzyl (dimethylamino) malonate. The product was crystallized from hexane; mp 78°-84° C. Anal. Calcd. for $C_{17}H_{23}N_3O$: C, 75.23; H, 9.28; H, 15.48. Found: C, 75.00; H, 9.47; N, 15.54.

EXAMPLE 90

5-(Dimethylamino)-5,6-dihydro-6-methyl-4H-imidazo(4,5,1-ij)quinolin-2(1H)-one hydrochloride (compound 66)

This compound, a mixture of diastereomers, was prepared following the procedure of Example 44 part B, but substituting 1,2,3,4-tetrahydro-4-methyl-$N^3$,$N^3$-dimethyl-3,8-quinolinediamine for t-butyl-(8-amino-1,2,3,4-tetrahydro-3-quinolyl)carbamate.

EXAMPLE 91

5-(Dipropylamino)-5,6-dihydro-6-methyl-4H-imidazo(4,5,1-ij)quinolin-2(1H)-one hydrochloride (compound 67)

This compound, a mixture of diastereomers, was prepared following the procedure of Example 44 part B, but substituting 1,2,3,4-tetrahydro-4-methyl-$N^3$,$N^3$-dipropyl-3,8-quinolinediamine for t-butyl (8-amino-1,2,3,4-tetrahydro-3-quinolyl)carbamate.

EXAMPLE 92

5,6-Dihydro-4-methyl-N,N-dipropyl-4H-imidazo(4,5,1-ij) quinolin-5-amine (compound 68)

Part A. β-(dipropylamino)-1H-benzimidazole-4-propanal

Oxalyl chloride (1.2 mL, 0.014 mol) was added with stirring to methylene chloride (20 mL) at −78° C. Ten minutes after addition was complete, DMSO (2 mL) was added and stirring was continued for an additional 10 minutes. β-Dipropylamino)-1H-benzimidazole-4-propanol (2.1 g, 7.5 mmol) in methylene chloride was added and, after 30 minutes, the solution was allowed to warm to room temperature. Water was added, the methylene chloride was separated and evaporated, and the residue was chromatographed on silica gel to give β-(dipropylamino)-1H-benzimidazole-4-propanal as an oil.

Part B. β-(dipropylamino)-α-methyl-1H-benzimidazole-4-propanol

Methyl magnesium bromide (3.3 mL) of 3.0M in ether, 6 mmol) was added to a stirred solution of β-(dipropylamino)-1H-benzimidazole-4-propanal (1.45 g, 5 mmol) in THF (25 mL). The solution was stirred for 1 hour, evaporated, and partitioned between ethyl acetate and water. The ethyl acetate was evaporated and the residue was chromatographed on silica gel to give β-(dipropylamino)-α-methyl-1H-benzimidazole-4-propanol as an oil.

Part C. 5,6-Dihydro-4-methyl-N,N-dipropyl-4H-imidazo(4,5,1-ij)quinolin-5-amine

This compound, a mixture of diastereomers, was prepared following the procedure of Example 18 part D, but substituting β-(dipropylamino)-α-methyl-1H-benzimidzole-4-propanol for β-(dipropylamino)1H-benzimidzole-4-propanol.

EXAMPLE 93

5,6-Dihydro-4-methyl-N,N-dimethyl-4H-imidazo(4,5,1-ij)quinolin-5-amine (compound 69)

This compound, a mixture of diastereomers, was prepared following the procedure of Example 18 part D, but substituting β-(dimethylamino)-α -methyl-1H-benzimidazole-4-propanol for β-(dipropylamino)-1H-benzimidazole-4-propanol.

EXAMPLE 94

5-(Dipropylamino)-5,6-dihydro-4-methyl-4H-imidazo-(4,5,1-ij)quinolin-2(1H)-one hydrochloride (compound 70)

This compound, a mixture of diastereomers, was prepared following the procedure of Example 44 part B, but substituting 1,2,3,4-tetrahydro-2-methyl-$N^3$, $N^3$-dipropyl-3,8-quinolinediamine for t-butyl (8-amino-1,2,3,4-tetrahydro-3-quinolyl)carbamate.

EXAMPLE 95

5-(Dimethylamino)-5,6,-dihydro-4-methyl-4H-imidazo-(4,5,1-ij)quinolin-2(1H)-one hydrochloride (compound 71)

This compound, a mixture of diastereomers, was prepared following the procedure of Example 44 part B, but substituting 1,2,3,4-tetrahydro-2-methyl-$N^3$, $N^3$-dimethyl-3,8-quinolinediamine for t-butyl (8-amino-1,2,3,4-tetrahydro-3-quinolyl)carbamate.

EXAMPLE 96

5-(Dipropylamino)-5,6-dihydro-2H,4H-oxazolo(5,4,3-ij)quinolin-2-one (compound 72)

Part A. N-Acetyl-N-(2-methoxy-6-methylphenyl)acetamide (compound XLV)

Palladium charcoal (1.0 g of 10%) was added to a solution of 3-methyl-2-nitroanisole (16.8 g, 0.1 mol) in ethanol (150 mL) and the solution was hydrogenated (50 lb initial hydrogen pressure) until hydrogen uptake ceased (2 hours). The solution was filtered and evaporated to give 13.8 g of 2-methoxy-6-methylbenzenamine (compound XLIV) as an oil. The product was dissolved in acetic anhydride (100 mL) and the resulting solution was refluxed for 1 hour. Part of the solvent (50 mL) was slowly removed over a 1-hour period, after which time the solution was cooled and the remainder of the solvent was removed under reduced pressure. The residual oil was crystallized from ethyl acetate:hexane (200 mL of 1:2) to give 20.5 g of N-acetyl-N-(2-methoxy-6-methylphenyl)-acetamide, mp 116°-119° C. Anal Calcd for $C_{12}H_{15}NO_3$: C, 65.14; H, 6.83; N, 6.33. Found: C, 65.44; H, 7.04; N, 6.39.

Part B. N-Acetyl-N-(2-(bromomethyl)-6-methoxyphenyl)acetamide (compound XLVI)

A mixture of N-acetyl-N-(2-methoxy-6-methylphenyl)acetamide (25.0 g, 0.11 mol), N-bromosuccinimide (20.1 g, 0.11 mol), and benzoyl peroxide (4.5 g, 0.019 mol) in carbon tetrachloride (300 mL) was stirred under reflux for 3 hours. The solution was cooled, filtered, and evaporated, and the residual solid was crystallized from ethyl acetate:hexane to give 21.0 g of N-acetyl-N-(2-(bromomethyl)-6-methoxyphenyl)acetamide, 95% pure by GC analysis.

Part C. Diethyl (dipropylamino){(2-diacetylamino)-3-methoxyphenyl)-methyl}propanedioate (compound XLVII)

Potassium hydride (13.4 g of 35%, 117 mmol) was added to a stirred solution of diethyl dipropylaminomalonate (34.6 g, 133 mmol) in the THF (200 mL). N-Acetyl-N-(2-(bromomethyl)-6-methoxyhenyl)acetamide (10.0 g, 33 mmol) was added and the solution was heated under reflux for 1 hour. The solution was evaporated and the residual oil was partitioned between ethyl acetate and water. After evaporation of the ethyl acetate, the residue was chromatographed on silica gel using ethyl acetate:hexane (1:10 as the eluant to give 9.2 g of diethyl (dipropylamino){(2-diacetylamino)-3-methoxyphenyl)methyl}propanedioate. Crystallization from ethyl acetate:hexane gave 8.4 g of product, mp 72°-75° C. Anal Calcd for $C_{25}H_{38}N_2O_7$: C, 62.74; H, 8.00; N, 5.85. Found: C, 62.59; H, 8.00; N, 5.87.

Part D. 3-(Dipropylamino)-3,4-dihydro-8-methoxy-2(1H)quinolinone (compound XLVIII)

Diethyl (dipropylamino){2-diacetylamino)-3-methoxyphenyl)methyl}propanedioate (6.34 g) was dissolved in sodium ethoxide in ethanol (150 mL of 1.4M). After 20 min, the solution was heated under reflux for 15 hours; water was added to the reaction after 1 hour (1 mL), 3 hours (2 mL), 4 hours (5 mL) and 5 hours (15 mL). The solution was filtered to remove precipitated inorganic material and the solvents were removed under reduced pressure, and the residue was partitioned between ethyl acetate and water. The oil obtained after evaporation of the ethyl acetate was chromatographed on silica gel to give 3.3 g of 3-(dipropylamino)-3,4-dihydro-8-methoxy-2(1H)quinolinone. The product was crystallized from pentane to give 2.0 g of product, mp 50°-54° C. Anal Calcd for $C_{16}H_{24}N_2O_2$: C, 69.53; H, 8.75; N, 10.14. Found: C, 69.56; H, 8.98; N, 10.24.

Part E. 1,2,3,4-Tetrahydro-8-methoxy-N,N-dipropyl-3-quinolinamine (compound XLIX)

Lithium aluminum hydride (1.08 g, 27.7 mmol) was added to a stirred solution of 3-(dipropylamino)-3,4-dihydro-8-methoxy-2(1H)quinolinone (1.05 g, 3.8 mmol) in THF (50 mL) and the solution was heated to 50° C. for 1 hour. After cooling, ethyl acetate followed by methanol were added to destroy excess hydride, and the solvent was evaporated. The residue was partitioned between ethyl acetate and water. Evaporation of the ethyl acetate gave 0.98 g of 1,2,3,4-tetrahydro-8-methoxy-N,N-dipropyl-3-quinolinamine as an oil.

Part F. 1,2,3,4-Tetrahydro-8-hydroxy-N,N-dipropyl-3-quinolinamine (compound L)

A solution of 1,2,3,4-tetrahydro-8-methoxy-N,N-dipropyl-3-quinolinamine (0.98 g) in hydrobromic acid (20 mL of 48%) was heated at 155° C. for 6 hours. The solution was cooled, evaporated, and partitioned between ethyl acetate and saturated sodium bicarbonate solution. The aqueous phase was re-extracted with ethyl acetate and the combined organic phases were evaporated to give 0.88 g of 1,2,3,4-tetrahydro-8-hydroxy-N,N-dipropyl-3-quinolinamine as an oil.

Part G. 5-(Dipropylamino)-5,6-dihydro-2H,4H-oxazolo(5,4,3-ij)quinolin-2-one (compound 72)

Carbonyldiimidazole (0.46 g, 2.8 mmol) was added to a stirred solution of 1,2,3,4-tetrahydro-8-hydroxy-N,N-dipropyl-3-quinolinamine (0.59 g, 2.4 mmol) in THF (10 mL). After 5 minutes, the solvent was removed and the residue was dissolved in ethyl acetate and chromatographed on silica gel using 5% ethyl acetate in hexane as the initial eluant to give 0.57 g of 5-(dipropylamino)-5,6-dihydro-2H,4H-oxazolo(5,4,3-ij)quinolin-2-one as an oil.

The bulk of the product was converted to the p-toluenesulfonate salt, mp 192°-194° C. from methanol:ether. Anal Calcd for $C_{16}H_{22}N_2O_2 \cdot C_7H_8O_3S$: C, 61.86; H, 6.77; N, 6.28; S, 7.18. Found: C, 61.90; H, 6.97; N, 6.28; S, 7.18.

EXAMPLE 97

5-(Propylamino)-5,6-dihydro-2H,4H-oxazolo(5,4,3-ij)quinolin-2-one (compound 73)

Part A. 5-(N-(phenylmethyl)propylamino)-5,6-dihydro-2H,4H-oxazolo(5,4,3-ij)quinolin-2-one This compound was obtained by following the procedure of Example 96, but substituting diethyl (N-(phenylmethyl)propylamino)malonate for diethyl (dipropylamino)malonate.

Part B. 5-(Propylamino)-5,6-dihydro-2H,4H-oxazolo(5,4,3-ij)quinolin-2-one

This compound was obtained by following the procedure of Example 66 part A, but substituting 5-(N-(phenylmethyl)propylamino)-5,6-dihydro-2H,4H-oxazolo(5,4,3-ij)quinolin-2-one for 6-bromo-1,2,3,4-tetrahydro-8-nitro-N,N-dimethyl-3-quinolinamine.

EXAMPLE 98

5-(Dimethylamino)-5,6-dihydro-2H,4H-oxazolo(5,4,3-ij)quinolin-2-one (compound 74)

This compound was prepared following the procedure of Example 96, but substituting diethyl (dimethylamino)malonate for diethyl (dipropylamino)malonate.

EXAMPLE 99

5-(N-methyl-1-(phenyl)ethylamino)-5,6-dihydro-2H,4H-oxazolo(5,4,3-ij)quinolin-2-one (compound 75)

This compound was prepared following the procedure of Example 96, but substituting diethyl (N-methyl-2-(phenyl)ethylamino)malonte for diethyl (dipropylamino)malonate.

EXAMPLE 100

1-(5,6-Dihydro-2-oxo-2H,4H-oxazolo(5,4,3-ij)quinolin-5-yl)pyrrolidine (compound 76)

This compound was prepared by following the procedure of Example 96, but substituting (1-pyrrolidinyl)propanedioic acid methyl benzyl diester (compound VIk) for diethyl dipropylaminomalonate.

EXAMPLE 101

1-(5,6-Dihydro-2-oxo-2H,4H-oxazolo(5,4,3-ij)quinolin-5-yl)piperidine (compound 77)

This compound was prepared by following the procedure of Example 96, but substituting (1-piperidinyl)- propanedioic acid methyl benzyl diester (compound VIm) for diethyl dipropylaminomalonate.

EXAMPLE 102

4-(5,6-Dihydro-2-oxo-2H,4H-oxazolo(5,4,3-ij)quinolin-5-yl)morpholine (compound 78)

This compound was prepared by following the procedure of Example 96, but substituting (4-morpholinyl)-propanedioic acid methyl benzyl diester (compound VIn) for diethyl dipropylaminomalonate.

EXAMPLE 103

1-(5,6-Dihydro-2-oxo-2H,4H-oxazolo(5,4,3-ij)quinolin-5-yl)imidazole (compound 79)

This compound was prepared by following the procedure of Example 96, but substituting (1-imidazolyl)-propanedioic acid methyl benzyl diester (compound VIp) for diethyl dipropylaminomalonate.

EXAMPLE 104

5-(Dipropylamino)-5,6-dihydro-2H,4H-oxazolo(5,4,3-ij)quinolin-2-thione (compound 80)

This compound was prepared by following the procedure of Example 56 part B, but substituting 1,2,3,4-tetrahydro-8-hydroxy-N,N-dipropyl-3-quinolinamine for 1,2,3,4-tetrahydro-$N^3,N^3$-dipropyl-3,8-quinolinamine.

EXAMPLE 105

5-(Dimethylamino)-5,6-dihydro-2H,4H-oxazolo(5,4,3-ij)quinolin-2-thione (compound 81)

This compound was prepared by following the procedure of Example 56 part B, but substituting 1,2,3,4-tetrahydro-8-hydroxy-N,N-dimethyl-3-quinolinamine for 1,2,3,4-tetrahydro-$N^3,N^3$-dipropyl-3,8-quinolinediamine.

EXAMPLE 106

6-(Dipropylamino)-6,7-dihydro-5H-pyrido(1,2,3-de)-1,4-benzoxazin-3(H)-one (compound 82)

This compound was prepared by following the procedure of Example 56 part B, but substituting ethyl bromoacetate for di (2-pyridyl)thiocarbonate and the sodium salt of 1,2,3,4-tetrahydro-8-hydroxy-N,N-dipropyl-3-quinolinamine for 1,2,3,4-tetrahydro-$N^3$, $N^3$-dipropyl-3,8-quinolinediamine. The bulk of the product was converted to the maleate salt, mp 124°-127° C.

EXAMPLE 107

6-(Dimethylamino)-6,7-dihydro-5H-pyrido(1,2,3-de)-1.4-benzoxazin-3(2H)-one (compound 83)

This compound was prepared by following the procedure of Example 56 part B, but substituting ethyl bromoacetate for di (2-pyridyl)thiocarbonate and the sodium salt of 1,2,3,4-tetrahydro-8-hydroxy-N,N-dimethyl-3-quinolinamine for 1,2,3,4-tetrahydro-$N^3,N^3$-dipropyl-3,8-quinolinediamine.

EXAMPLE 108

1,2,6,7-Tetrahydro-6-(dipropylamino)-2-methyl-3H,5H-pyrido(1,2,3-de)quinoxalin-3-one (compound 84)

This compound was prepared using the procedure of Example 56, but substituting ethyl α-bromopropionate for di (2-pyridyl)thiocarbonate and carrying the reaction out at the reflux temperature. The crude product was chromatographed to give, as the major product and first compound eluted from the column, 1,2,6,7-tetrahydro-6-(dipropylamino)-2-methyl-3H,5H-pyrido(1,2,3-de)quinoxalin-3-one.

EXAMPLE 109

1,2,6,7-Tetrahydro-6-(dipropylamino)-3-methyl-3H,5H-pyrido(1,2,3-de)quinoxalin-2-one (compound 85)

This compound was prepared using the procedure of Example 56, but substituting chloropropionyl chloride for di (2-pyridyl)thiocarbonate. The initially formed $N^8$-(α-chloropropionyl)-1,2,3,4-tetrahydro-$N^3,N^3$-dipropyl-3,8-quinolinediamine was heated at 150° C. in DMF to effect cyclization to 1,2,6,7-tetrahydro-6-(dipropylamino)-3-methyl-3H,5H-pyrido(1,2,3-de)quinoxalin-2-one.

EXAMPLE 110

5,6-Dihydro-N,N-dipropyl-4H-pyrrolo(3,2,1-ij)quinolin-5-amine (compound 86)

This compound was prepared by following the procedure of Example 18, but substituting methyl 7-(bromomethyl)-1H-indole-1-carboxylate for t-butyl 4-(bromomethyl)-1H-benzimidazole-1-carboxylate.

EXAMPLE 111

5,6-Dihydro-N,N-dimethyl-4H-pyrrolo(3,2,1ij)quinolin-5-amine (compound 87)

This compound was prepared by following the procedure of Example 18, but substituting methyl 7-(bromomethyl)-1H-indole-1-carboxylate for t-butyl 4-(bromomethyl)-1H-benzimidazole-1-carboxylate and diethyl (dimethylamino)malonte for diethyl (dipropylamino)malonate. The bulk of the product was converted to the maleate salt, mp 114°-115° C. from THF/ether.

EXAMPLE 112

5,6-Dihydro-N,N-dipropyl-4H-pyrazolo(4,3,2-i)quinolin-5-amine (compound 88)

This compound was prepared by following the procedure of Example 18, but substituting methyl 7-(bromomethyl)-1H-indazole-1-carboxylate for t-butyl 4-(bromomethyl)-1H-benzimidazole-1-carboxylate.

EXAMPLE 113

5,6-Dihydro-N,N-dimethyl-4H-pyrazolo(4,3,2-ij)quinolin-5-amine (compound 89)

This compound was prepared by following the procedure of Example 18, but substituting methyl 7-(bromomethyl)-1H-indazole-1-carboxylate for t-butyl 4-(bromomethyl)-1H-benzimidazole-1-carboxylate and diethyl (dimethylamino)malonate for diethyl (dipropylamino)malonate.

EXAMPLE 114

5,6-Dihydro-N,N-dipropyl-4H-triazolo(4,5,1-ij)quinolin-5-amine (compound 90)

This compound was prepared by following the procedure of Example 18, but substituting methyl 4-(bromomethyl)-1H-benzotriazole-1-carboxylate for t-butyl 4-(bromomethyl)-1H-benzimidazole-1-carboxylate.

EXAMPLE 115

5,6-Dihydro-N,N-dimethyl-4H-triazolo(4,5,1-ij)quinolin-5-amine (compound 91)

This compound was prepared by following the procedure of Example 18, but substituting methyl 4-(bromomethyl)-1H-benzotriazole-1-carboxylate for t-butyl 4-(bromomethyl)-1H-benzimidazole-1-carboxylate and diethyl (dimethylamino)-malonate for diethyl (dipropylamino)malonate.

EXAMPLE 116

1,2,5,6-Tetrahydro-N,N-dipropyl-4H-pyrrolo(3,2,1-ij)quinolin-5-amine (compound 92)

This compound was prepared by following the procedure of Example 18, but substituting t-butyl 2,3-dihydro-7-(bromomethyl)-1H-indole-1-carboxylate for t-butyl 4-(bromomethyl)-1H-benzimidazole-1-carboxylate. The bulk of the product was converted to the maleate salt, mp 139°–140° C. from THF/ether.

EXAMPLE 117

1,2,5,6-Tetrahydro-N,N-dimethyl-4H-pyrrolo(3,2,1-ij)quinolin-5-amine (compound 93)

This compound was prepared by following the procedure of Example 18, but substituting t-butyl 2,3-dihydro-7-(bromomethyl)-1H-indole-1-carboxylate for t-butyl 4-(bromomethyl)-1H-benzimidazole-1-carboxylate and diethyl (dimethylamino)malonate for diethyl (dipropylamino)malonate.

EXAMPLE 118

5-(Propylamino)-5,6-dihydro-4H-pyrrolo(3,2,1-ij)quinolin-2,3H)-dione (compound 94)

Part A. N-Propyl-N-(6-bromo-1,2,3,4-tetrahydro-8-nitroquinolin-3-yl)formamide.

This product was prepared by following the procedure of Example 35, but substituting 6-bromo-1,2,3,4-tetrahydro-8-nitro-N-propyl-3-quinolinamine for 3-aminoquinoline.

Part B. N-propyl-N-(8-amino-1,2,3,4-tetrahydro-3-quinolyl)formamide

This product was prepared by following the procedure of Example 56 part A, but substituting N-propyl-N-(6-bromo-1,2,3,4-tetrahydro-8-nitro-3-quinolyl) for 6-bromo-1,2,3,4-tetrahydro-8-nitro-N,N-dipropyl-3-quinolinamine.

Part C. N-propyl-N-(5,6-dihydro-2,3-dioxo-4H-pyrrolo(3,2,1-ij)quinolin-5-yl)formamide Oxalyl chloride (1.26 g, 0.01 mol) was added to a stirred solution of N-propyl-N-(6-bromo-1,2,3,4-tetrahydro-8-nitroquinolin-3-yl)formamide (3.14 g, 0.01 mol) in ether (100 mL). After 30 minutes, the ether was removed and the residue was heated at 100° C. for 4 hours to effect cyclization. The crude product was partitioned between ethyl acetate and water, the ethyl acetate phase was evaporated, and the residual product was chromatographed on silica gel to give N-propyl-N-(5,6-dihydro-2,3-dioxo-4H-pyrrolo(3,2,1-ij)quinolin-5-yl)formamide.

Part D. 5-(Propylamino)-5,6-dihydro-4H-pyrrolo(3,2,1-ij)quinolin-2,3-dione (compound 94)

N-Propyl-N-(5,6-dihydro-2,3-dioxo-4H-pyrrolo(3,2,1-ij)quinolin-5-yl)formamide was refluxed for 1 hour with ethanolic hydrogen chloride to give the hydrochloride salt of 5-(propylamino)-5,6-dihydro-4H-pyrrolo(3,2,1-ij)quinolin-2,3-dione.

EXAMPLE 119

5-(Dipropylamino)-5,6-dihydro-4H-pyrrolo(3,2,1-ij)quinolin-1,3-dione (compound 95)

This product was prepared by following the procedure of Example 54, but substituting 5-(propylamino)-5,6-dihydro-4H-pyrrolo(3,2,1-ij)quinolin-2,3H)-dione hydrochloride for 6-bromo-1,2,3,4-tetrahydro-8-nitro-3-quinolinamine dihydrochloride.

EXAMPLE 120

5-(Propylamino)-5,6-dihydro-4H-pyrrolo(3,2,1-ij)quinolin-2(1H)-one (compound 96)

This product was prepared by following the procedure of Example 36, but substituting 5-(propylamino)-5,6-dihydro-4H-pyrrolo(3,2,1-ij)quinolin-2,3-dione for N-(3-quinolyl)formamide.

EXAMPLE 121

5-(Dipropylamino)-5,6-dihydro-4H-pyrrolo(3,2,1-ij)quinolin-2(1H)-one (compound 97)

This product was prepared by following the procedure of Example 36, but substituting 5-(dipropylamino)-5,6-dihydro-4H-pyrrolo(3,2,1-ij)quinolin-2,3-dione for N-(3-quinolyl)formamide. The product was crystallized from hexane, mp 86°–88° C.

EXAMPLE 122

6-(Dipropylamino)-2,3,6,7-tetrahydro-5H-pyrido(3,2,1-ij)quinazolin-3one (compound 98)

Part A. Methyl 3-methyl-2-nitrobenzoate

3-Methyl 2-nitrobenzoic acid (15.0 g) was stirred overnight with methanolic hydrogen chloride (150 mL of 2.2N). The reaction was then refluxed for 3 hours, cooled and filtered to give 9.0 g of methyl 3-methyl-2-nitrobenzoate, mp 72°–75° C. The mother liquors of the filtration contained a mixture of the starting acid and ester product.

Part B. Methyl 3-(bromomethyl)-2-nitrobenzoate

This product was prepared by following the procedure of Example 6, but substituting methyl 3-methyl-2-nitrobenzoate for 8-methylquinoline. The product was purified by chromatography on silica gel and was crystallized from ethyl acetate:hexane; mp 91°–95° C.

Part C. (Dipropylamino)(3-carbomethoxy-2-nitrophenyl)methyl)propanedioic acid methyl benzyl diester This product was prepared by following the procedure of Example 19 part A, but substituting methyl 3-(bromomethyl)-2-nitrobenzoate for t-butyl 4-(bromomethyl)-1H-benzimidazole-1-carboxylate and (dipropylamino)propanedioic acid methyl benzyl diester for diethyl (dipropylamino)malonate.

Part D. Methyl 3-(dipropylamino)-1,2,3,4-tetrahydro-2-oxo-8-quinolinecarboxylate A mixture of (dipropylamino)(3-carbomethoxy-2-nitrophenyl)methyl)propanedioic acid methyl benzyl diester (5.0 g), 10% palladium charcoal (0.5 g) in methanol (150 mL) was hydrogenated until hydrogen uptake ceased. The solution was filtered and the solvent removed to give 3.0 g of methyl α-(dipropylamino)-(2-amino-3-carbomethoxyphenyl)propanoate as an oil. This was refluxed in DMF for 18 hours to effect cyclization. The solvent was removed and the residual oil was chromatographed on silica gel to give 2.4 g of methyl 3-(dipropylamino)-1,2,3,4-tetrahydro-2-oxo-8-quinolinecarboxylate.

Part E. 3-(Dipropylamino)-1,2,3,4-tetrahydro-2-oxo-8-quinolinecarboxylic acid

A mixture of methyl 3-(dipropylamino)-1,2,3,4-tetrahydro-2-oxo-8-quinolinecarboxylate (1.0 g), methanol (15 mL) and 4.0N sodium hydroxide solution (3.3 mL) was stirred at room temperature for 30 minutes. The methanol was removed and the residue was reconstituted in water (5 mL) and neutralized by addition of 4.0N hydrochloric acid (3.3 mL). The precipitate was filtered off, washed with water and air dried to give 0.67 g of 3-(dipropylamino)-1,2,3,4-tetrahydro-2-oxo-8-quinolinecarboxylic acid, mp 214°-217° C. Anal Calcd for $C_{16}H_{22}N_2O_3$: C, 66.18; H, 7.64; N, 9.65. Found: C, 65.99; H, 7.67; N, 9.62.

Part F. 3-(Dipropylamino)-1,2,3,4-tetrahydro-2-oxo-8-quinolinecarboxamide

A mixture of 3-(dipropylamino)-1,2,3,4-tetrahydro-2-oxo-8-quinolinecarboxylic acid (1.0 g), 1-hydroxybenzotriazole (1.65 g, 11 mmol) and dicyclohexylcarbodiimide (3.09 g, 15 mmol) in dimethylformamide (25 mL) was stirred at room temperature for 15 minutes. Ammonia was then bubbled into the solution, and, after 15 minutes the solution was filtered, evaporated and partitioned between ethyl acetate and sodium hydroxide solution. The ethyl acetate was evaporated and the residual solid was purified by chromatography on silica gel using ethyl acetate as the eluant to give 0.98 g of product. This was crystallized from methanol to give 0.78 g of 3-(dipropylamino)-1,2,3,4-tetrahydro-2-oxo-8-quinolinecarboxamide, mp 214°-217° C. Anal Calcd for $C_{16}H_{23}N_3O_2$: C, 66.41; H, 8.01; N, 14.52. Found: C, 66.46; H, 8.30; N, 14.69.

Part G. 1,2,3,4-Tetrahydro-8-(aminomethyl)-N,N-dipropyl-3-quinolinamine

Lithium aluminum hydride (1.5 g) was added to a stirred solution of 3-(dipropylamino)-1,2,3,4-tetrahydro-2-oxo-8-quinolinecarboxamide (0.75 g) in THF (125 mL) and the solution was refluxed for 2 days. The solution was cooled and excess hydride was destroyed by addition of methanol (20 mL) and the solvents were removed under reduced pressure. The residue was partitioned between ethyl acetate (400 mL) and water (15 mL). The ethyl acetate was decanted from the inorganic solids and the solvent removed under reduced pressure. The residual oil was dissolved in chloroform and chromatographed on silica gel. Elution of the column with 5% methanol:chloroform gave 0.40 g of 1,2,3,4-tetrahydro-8-(aminomethyl)-N,N-dipropyl-3-quinolinamine.

Part H. 6-(Dipropylamino)-2,3,6,7-tetrahydro-5H-pyrido(3,2,1-ij)quinazolin-3-one (compound 98)

This compound was prepared by following the procedure of Example 96 part G, but substituting 1,2,3,4-tetrahydro-8-(aminomethyl)-N,N-dipropyl-3-quinolinamine for 1,2,3,4-tetrahydro-8-hydroxy-N,N-dipropyl-3-quinolinamine. The product was crystallized from hexane; mp 116°-119° C.

EXAMPLE 123

6-(Dimethylamino)-2,3,6,7-tetrahydro-5H-pyrido(3,2,1-ij)quinazolin-3-one (compound 99)

This compound was prepared by following the procedure of Example 122, but substituting (dimethylamino)propanedioic acid methyl benzyl diester for (dipropylamino)propanedioic acid methyl benzyl diester in part C of the reaction sequence.

EXAMPLE 124

6l-(Dipropylamino)-6,7-dihydro-1H,5H-pyrido(1,2,3-de)-2,4-benzoxazine-3-one (compound 100)

Part A. 1,2,3,4-Tetrahydro-8-(hydroxymethyl)-N,N-dipropyl-3-quinolinamide

This compound was obtained by following the procedure of Example 122 part G, but substituting methyl 3-(dipropylamino)-1,2,3,4-tetrahydro-2-oxo-8-quinolinecarboxylate for 3-(dipropylamino)-1,2,3,4-tetrahydro-2-oxo-8-quinolineoxamide.

Part B. 6-(Dipropylamino)-6,7-dihydro-1H,5H-pyrido(1,2,3-de)-2,4-benzoxanine-3-one (compound 100)

This compound was prepared by following the procedure of Example 44 part B, but substituting 1,2,3,4-tetrahydro-8-(hydroxymethyl)-N,N-dipropyl-3-quinolinamine for t-butyl(8-amino-1,2,3,4-tetrahydro-3-quinolyl)carbamate. The bulk of the product was converted to the hydrochloride salt, mp 192°-195° C.

EXAMPLE 125

6-(Dimethylamino)-6,7-dihydro-1H,5H-pyrido(3,2,1-ef)-2,4-benzoxanine-3-one (compound 101)

This compound was obtained by following the procedure of Example 124, but substituting methyl 3-(dimethylamino)-1,2,3,4-tetrahydro-2-oxo-8-quinolinecarboxylate for methyl 3-(dipropylamino)-1,2,3,4-tetrahydro-2-oxo-8-quinolinecarboxylate.

EXAMPLE 126

6-(Dipropylamino)-6,7-dihydro-3H,5H-benzo(ij)-quinolizin-3-one (compound 102)

Part A. 5-(Dipropylamino)-1,2,3,4-tetrahydro-8-quinolinecarboxaldehyde

This compound was obtained by following the procedure of Example 92 part A, but substituting 1,2,3,4-tetrahydro-8-(hydroxymethyl)-N,N-dipropyl-3-quinolinamine for β-(dipropylamino)-1H-benzimidazole-4-propanol.

Part B. 6-(Dipropylamino)-6,7-dihydro-3H,5H-benzo(ij)quinolizin-3-one (compound 102)

A mixture of 5-(dipropylamino)-1,2,3,4-tetrahydro-8-quinolinecarboxaldehyde (2.60 g, 0.01 mol), diethyl malonate (1.76 g, 0.011 mol), piperidine (0.3 g) and acetic acid (0.1 mL) in ethanol (20 mL) was refluxed for 6 hours. The solvents were removed and the residue was reconstituted in DMF and refluxed for 3 hours. The DMF was removed and the residue was chromatographed to give 6-(dipropylamino)-6,7-dihydro-3-oxo-3H,5H-benzo(ij)quinolizin-2-carboxylate. This was dissolved in ethanol (50 mL) and treated with sodium hydroxide solution (10 mL of 4N) for 1 hour. The solution was neutralized with hydrochloric acid to give 6-(dipropylamino)-6,7-dihydro-3H,5H-benzo(ij)quinolizin-3-one. The product was crystallized from hexane, mp 82°-84° C.

EXAMPLE 127

6-(Dimethylamino)-6,7-dihydro-3H,5H-benzo(ij)-quinolizin-3-one (compound 103)

This compound was obtained by following the procedure of Example 126, but substituting 1,2,3,4-tetrahydro-8-(hydroxymethyl)-N,N-dimethyl-3-quinolinamine for 1,2,3,4-tetrahydro-8-(hydroxymethyl)-N,N-dipropyl-3-quinolinamine.

EXAMPLE 128

6-(Dipropylamino)-2,3,6,7-tetrahydro-3H,5H-benzo(ij)-quinolizin-3-one (compound 104)

This product was prepared by following the procedure of Example 36, but substituting 6-(dipropylamino)-6,7-dihydro-3H,5H-benzo(ij)quinolizin-3-one for N-(3-quinolyl)formamide. The product was crystallized from pentane, mp 44°–45° C.

EXAMPLE 129

6-(Dimethylamino)-2,3,6,7-tetrahydro-3H,5H-benzo(ij)quinolizin-3-one (compound 105)

This product was prepared by following the procedure of Example 36, but substituting 6-(dipropylamino)-6,7-dihydro-3H,5H-benzo(ij)quinolizin-3-one for N-(3-quinolyl)formamide.

EXAMPLE 130 t-Butyl 1,2,3,4-Tetrahydro-5-(dipropylamino)quinoline-1-carboxylate

A mixture of 1,2,3,4-tetrahydro-$N^3,N^3$-dipropylquinoline (31.4 g, 0.135 mol) and di t-butyl dicarbonate (32.5 g, 0.149 mol) was heated at 100° C. for 1 hour. The product was chromatographed on silica gel using ethyl acetate:hexane as the eluent to give 42.6 g of t-butyl 1,2,3,4-tetrahydro-5-(dipropylamino)quinoline-1-carboxylate, mp 40°–42° C.

A portion of the product was converted to the hydrochloride salt, mp 168° C. (dec) from methanol:ether.

EXAMPLE 131 t-Butyl 1,2,3,4-Tetrahydro-8-methyl-5-(dipropylamino)-quinoline-1-carboxylate (LII)

s-Butyl lithium (17.7 mL of 1.3M in hexane (0.045 mol) was added at −78° C. to a stirred solution of t-butyl 1,2,3,4-tetrahyfro-5-(dipropylamino)quinoline-1-carboxylate (10 g, 0.030 mol) in THF (200 mL). After 15 minutes, methyl iodide (17.1 g, 0.13 mol) was added and the solution was allowed to warm to room temperature. The THF was removed under pressure, and the residual oil was partitioned between ethyl acetate and water. The ethyl acetate was evaporated and the residual oil was chromatographed on silica gel to afford 10.65 g of t-butyl 1,2,3,4-tetrahydro-8-methyl-5-(dipropylamino)quinoline-1-carboxylate as an oil.

EXAMPLE 132

5-(Dipropylamino)-5,6-dihydro-4H-pyrrolo[3,2,1-ij]quinolin-2(1H)-one (compound 97)

Following the procedure of Example 131, but substituting t-butyl 1,2,3,4-tetrahydro-8-methyl-5-(dipropylamino)quinoline-1-carboxylate for t-butyl 1,2,3,4-tetrahydro-5-(dipropylamino)quinoline-1-carboxylate and carbon dioxide for methyl iodide there was obtained 1,2,3,4-tetrahydro-1-(t-butoxycarbonyl)-5-(dipropylamino)quinoline-8-propionic acid. The product was treated with trifluoracetic acid to remove the t-butoxycarbonyl group and effect cyclization to 5-(dipropylamino)-5,6-dihydro-4H-pyrrolo[3,2,1-ij]quinolin-2(1H)-one, mp 84°–86° C.

EXAMPLE 133

Lithium aluminum hydride reduction of 5-(Dipropylamino)-5,6-dihydro-4H-pyrrolo[3,2,1-ij]quinolin-2(1H)-one (compound 97).

A mixture of 5-(dipropylamino)-5,6-dihydro-4H-pyrrolo[3,2,1-ij]quinolin-2(1H)-one (0.75 g) and lithium aluminum hydride (0.21 g) was stirred in ether (20 mL) for 45 minutes. The reaction was quenched with methanol, evaporated and partitioned between ethyl acetate and water. Evaporation of the ethyl gave an oil which was chromatographed on silica gel using ethyl acetate:hexane (1:20) as eluant to give, as the first compound eluted from the column 0.27 g of 5,6-dihydro-N,N-dipropyl-4H-pyrrolo[3,2,1-ij]quinolin-5-amine (compound 87). Continued elution of the column gave 0.34 g of 1,2,5,6-tetrahydro-N,N-dipropyl-4H-pyrrolo[3,2,1-ij]quinolin-5-amine (compound 92).

EXAMPLE 134

5,6-dihydro-5-(dipropylamino)-4H-pyrrolo[3,2,1-ij]quinolin-2,3-dione (compound 95).

Following the procedure of Example 131, but substituting ethyl oxalate for methyl iodide, there was obtained 1,2,3,4-tetrahydro-1-(t-butoxycarbonyl)-α-oxo-5-(dipropylamino)quinoline-8-propionic acid (LIII). The product was treated with trifluoracetic acid to effect cyclization to 5,6-dihydro-5-(dipropylamino)-4H-pyrrolo[3,2,1-ij]quinolin-2,3-dione (compound 95)

EXAMPLE 135

6-(Dipropylamino)-6,7-dihydro-3H,5H-benzo[ij]-quinolizin-3-one (compound 102)

Following the procedure of Example 131, but substituting ethyl formate for methyl iodide there was obtained t-butyl 8-formyl-1,2,3,4-tetrahydro-5-(dipropylamino)quinoline-1-carboxylate (LIV) as an oil. The product (3.6 g) was added to a stirred solution of trimethyl phosphonoacetate (3.64 g) and sodium hydride (0.96 g) in acetonitrile (75 mL). The solution was evaporated, chromatographed to afford 3.6 g of methyl 1,2,3,4-tetrahydro-1-(t-butoxycarbonyl)-α-oxo-5-(dipropylamino)quinoline-8-butenoate (LV) as an oil. The product was treated with trifluoracetic acid to remove the t-butoxycarbonyl protecting group and refluxed in ethanol to effect cyclization to 6-(dipropylamino)-6,7-dihydro-3H,5H-benzo[ij]quinolizin-3-one (compound 102).

EXAMPLE 136

Allylation of 5-(amino)-5,6-dihydro-4H-imidazo[4,5,1-ij]quinolin-2(1H)-one.

Following the procedure of Example 54, but substituting allyl bromide for iodopropane and 5-(amino)-5,6-dihydro-4H-imidazo[4,5,1-ij]quinolin-2(1H)-one for 6-bromo-1,2,3,4-tetrahydro-8-nitro-3-quinolinamine dihydrochloride there were obtained 5-(diallylamino)-5,6-dihydro-4H-imidazo[4,5,1-ij]quinolin-2(1H)-one, mp 150-152 from ethyl acetate and 5-(allylamino)-5,6-dihydro-4H-imidazo[4,5,1-ij]quinolin-2(1H)-one. The latter compound was converted to the hydrochloride salt, mp 260° from methanol:ether.

EXAMPLE 137

Reaction of 5-(amino)-5,6-dihydro-4H-imidazo[4,5,1-ij[quinolin-2(1H)-one with cyclopropylmethyl bromide.

Following the procedure of Example 54, but substituting cyclopropylmethyl bromide for iodopropane and 5-(amino)-5,6-dihydro-4H-imidazo[4,5,1-ij]quinolin-nitro-3-quinolinamine dihydrochloride there were obtained 5-[bis(cyclopropylmethyl)amino]-5,6-dihydro-4H-imidazo[4,5,1-ij]quinolin-2(1H)-one, mp 152-154 from ethyl acetate:hexane and 5-(cyclopropylmethylamino)-5,6-dihydro-4H-imidazo[4,5,1-ij]quinolin-2(1H)-one. The latter compound was converted to the hydrochloride salt, mp 309° C. (dec) from methanol:ether.

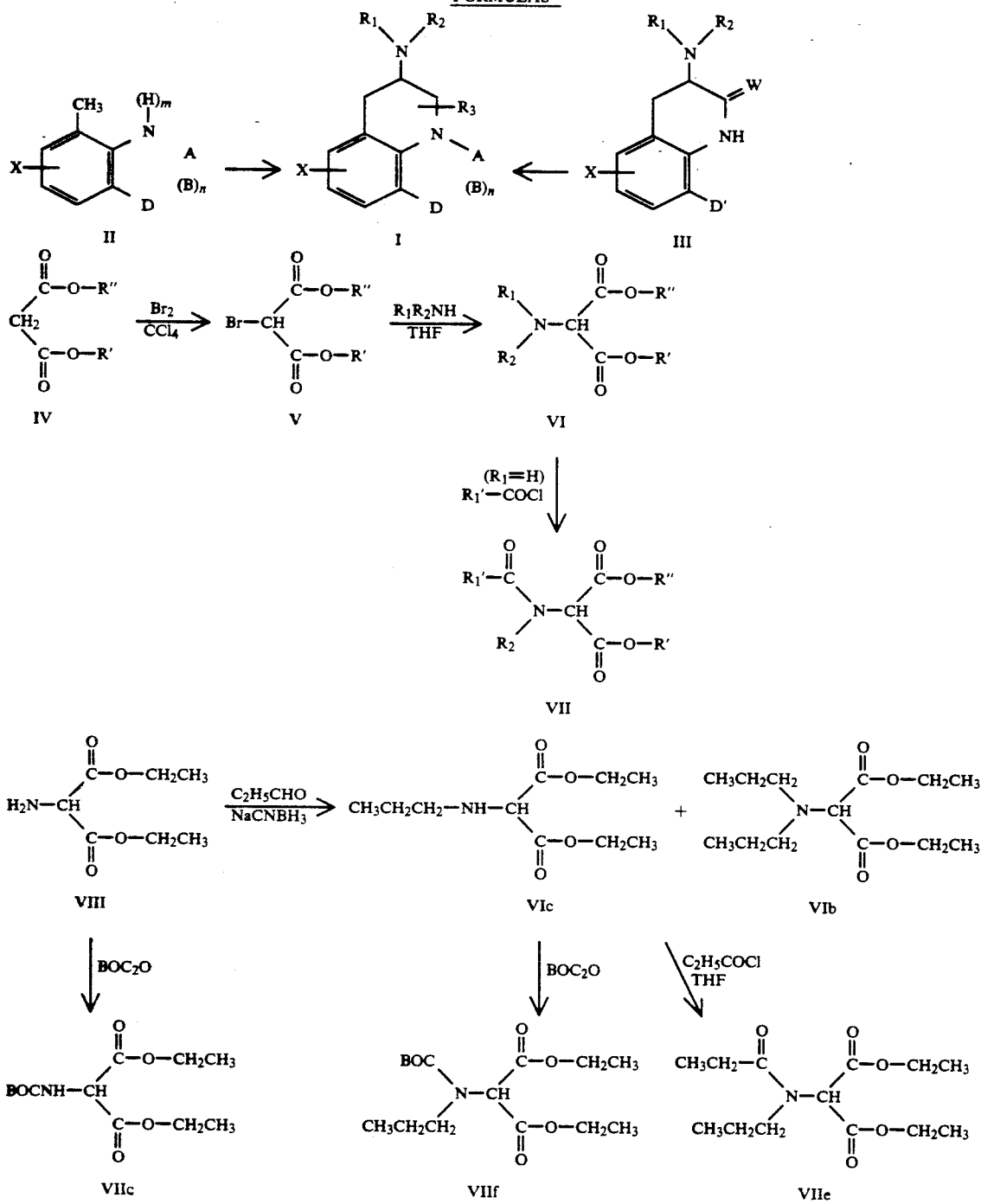

SCHEME 1
Synthesis of 2,3,6,7-Tetrahydro-1H,5H-benzo(ij)quinolizin-2-amines

SCHEME 1
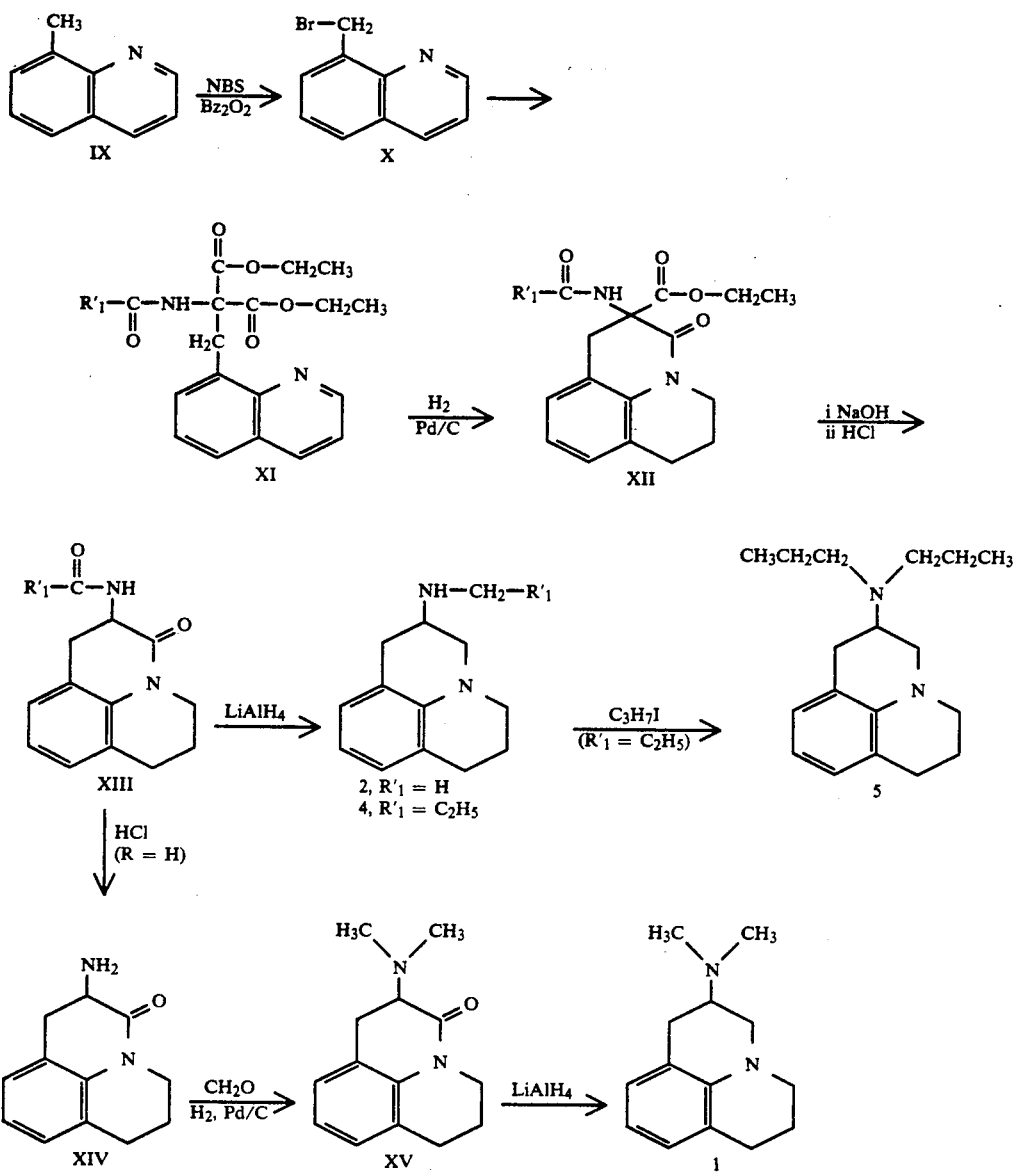
SCHEME 2
Synthesis of 5,6-Dihydro-N,N-dipropyl-4H-imidazo(4,5,1-ij)quinolin-5-amine
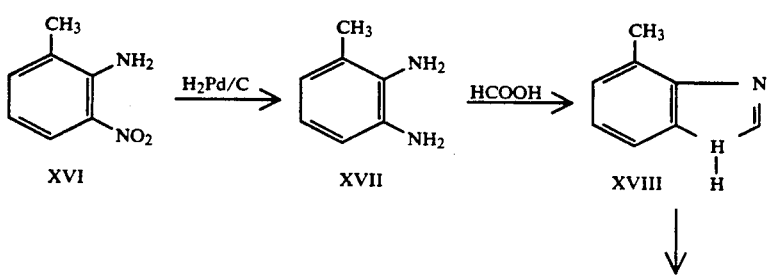

SCHEME 2
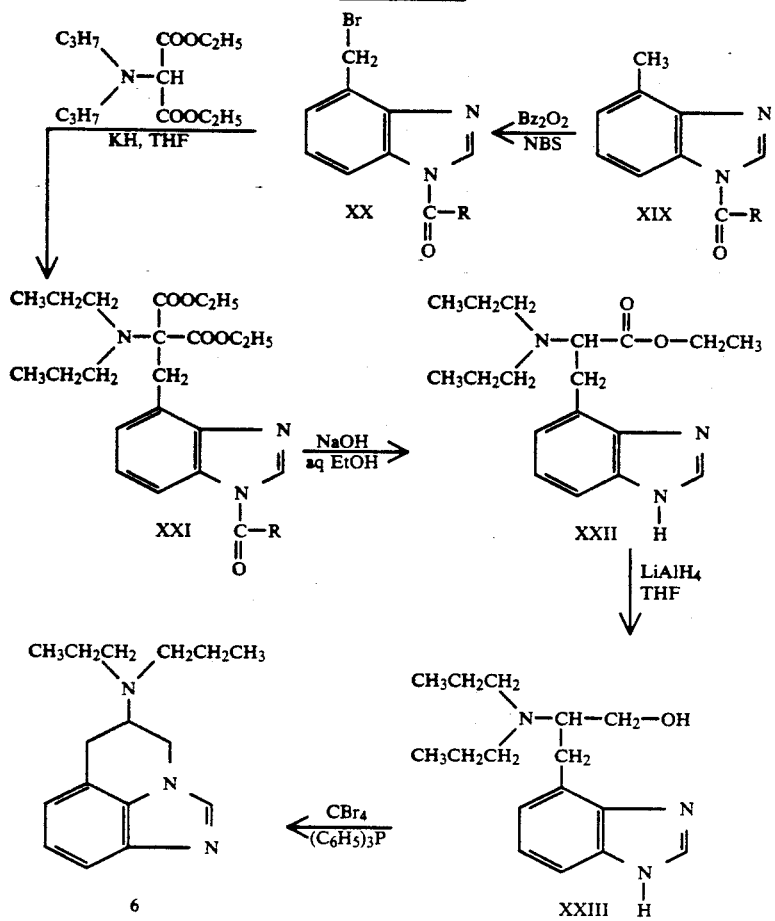
SCHEME 3
Synthesis of 5,6-Dihydro-4H-imidazo(4,5,1-ij)quinolin-5-amines
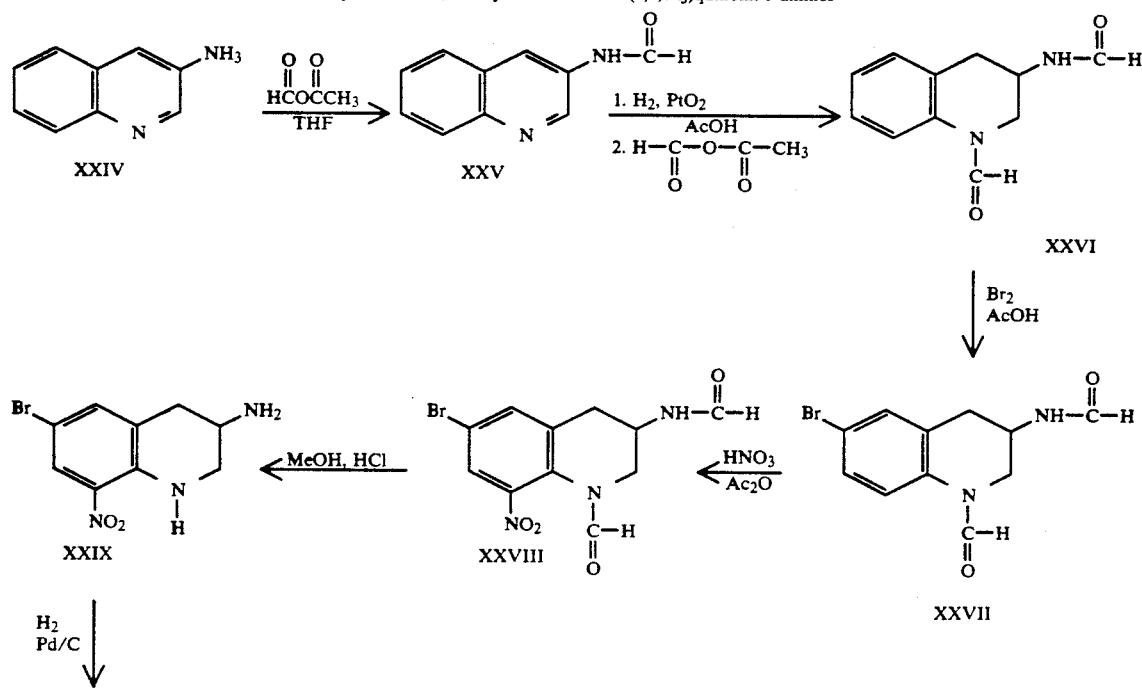

SCHEME 3
Synthesis of 5,6-Dihydro-4H-imidazo(4,5,1-ij)quinolin-5-amines
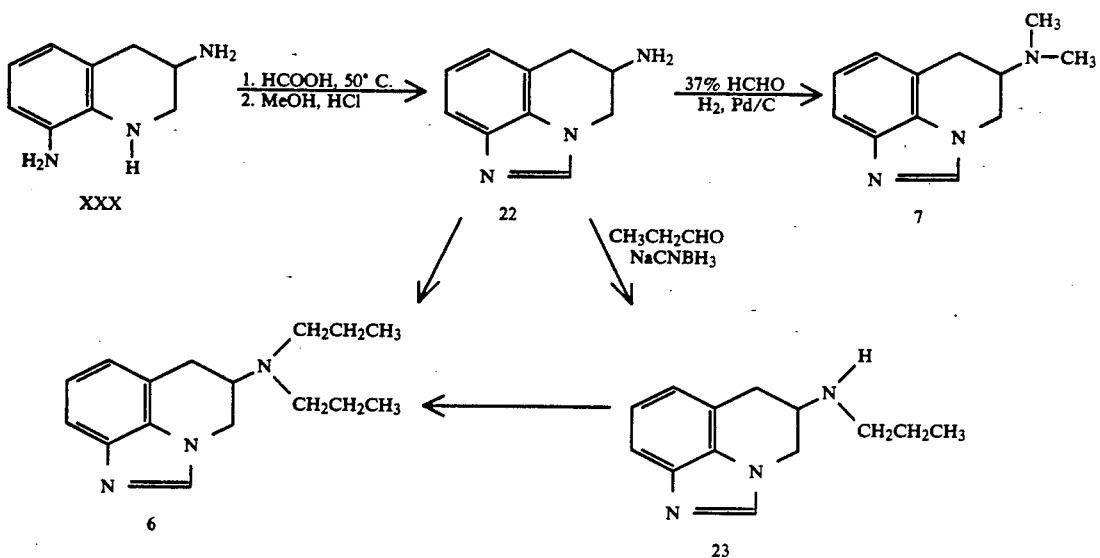
SCHEME 4
Synthesis of 5-Amino-5,6-dihydro-4H-imidazo(4,5,1-ij)quinolin-2-ones
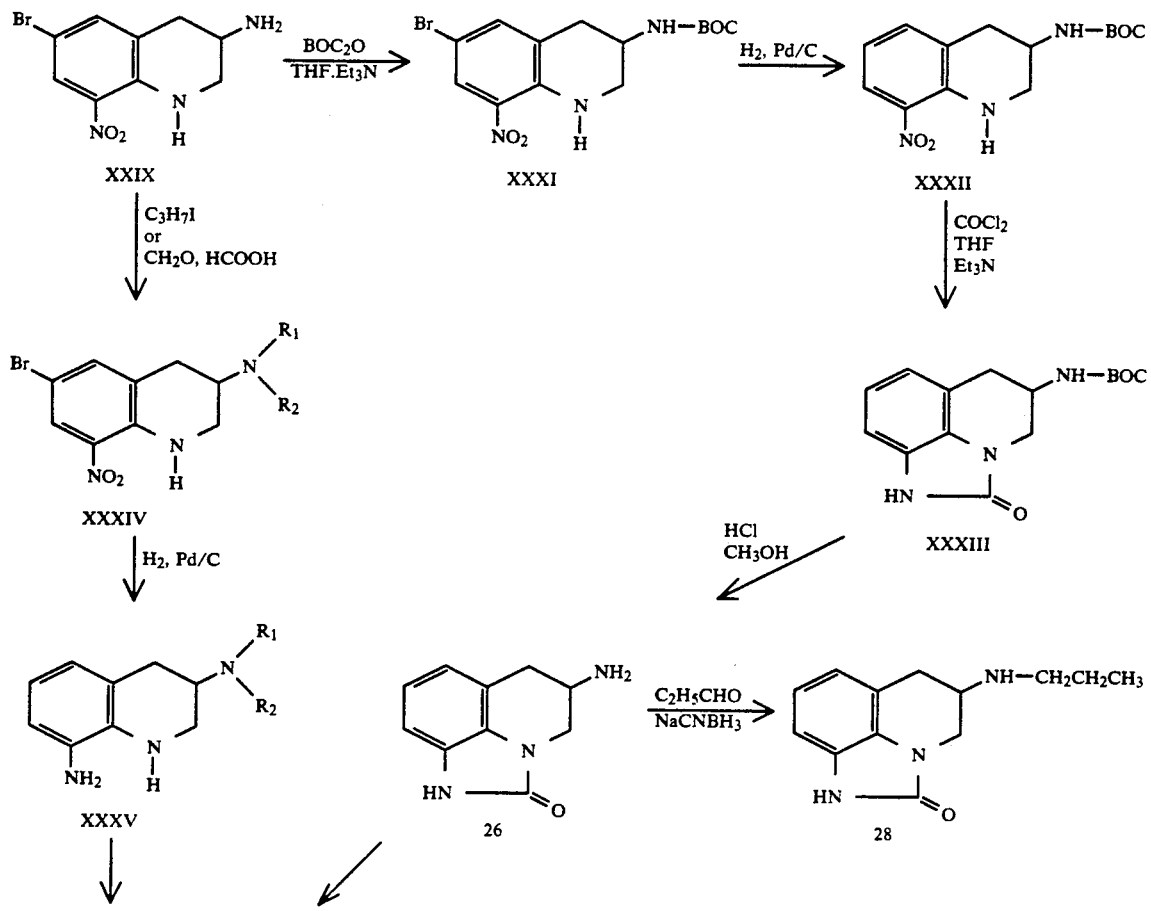

-continued
SCHEME 4
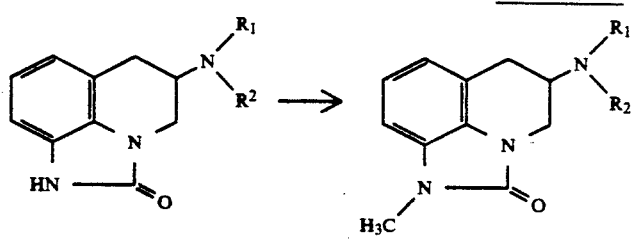
R$_1$ and R$_2$ are both (a) C$_3$H$_7$ or (b) CH$_3$.
SCHEME 5
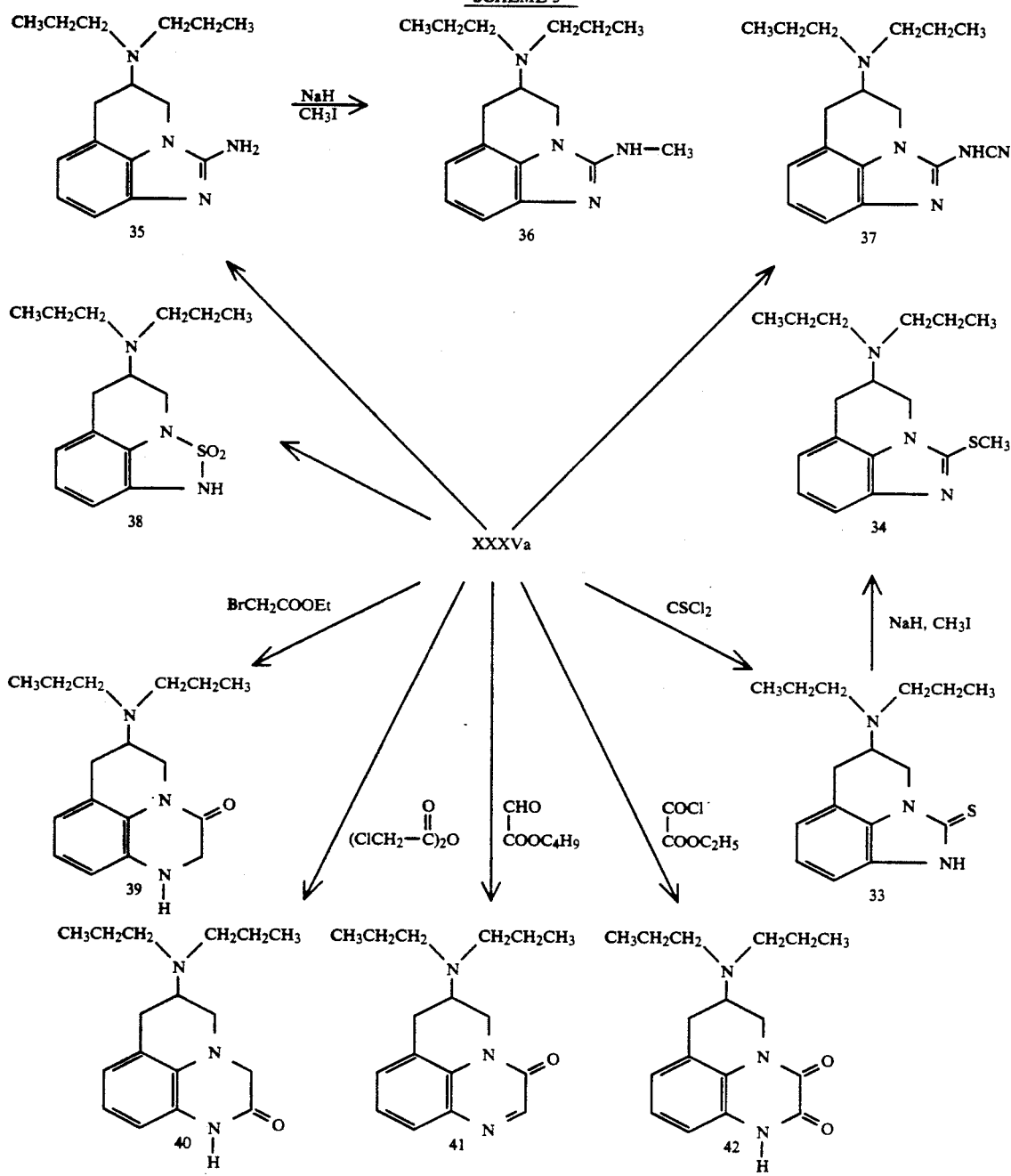

5,273,975
SCHEME 6
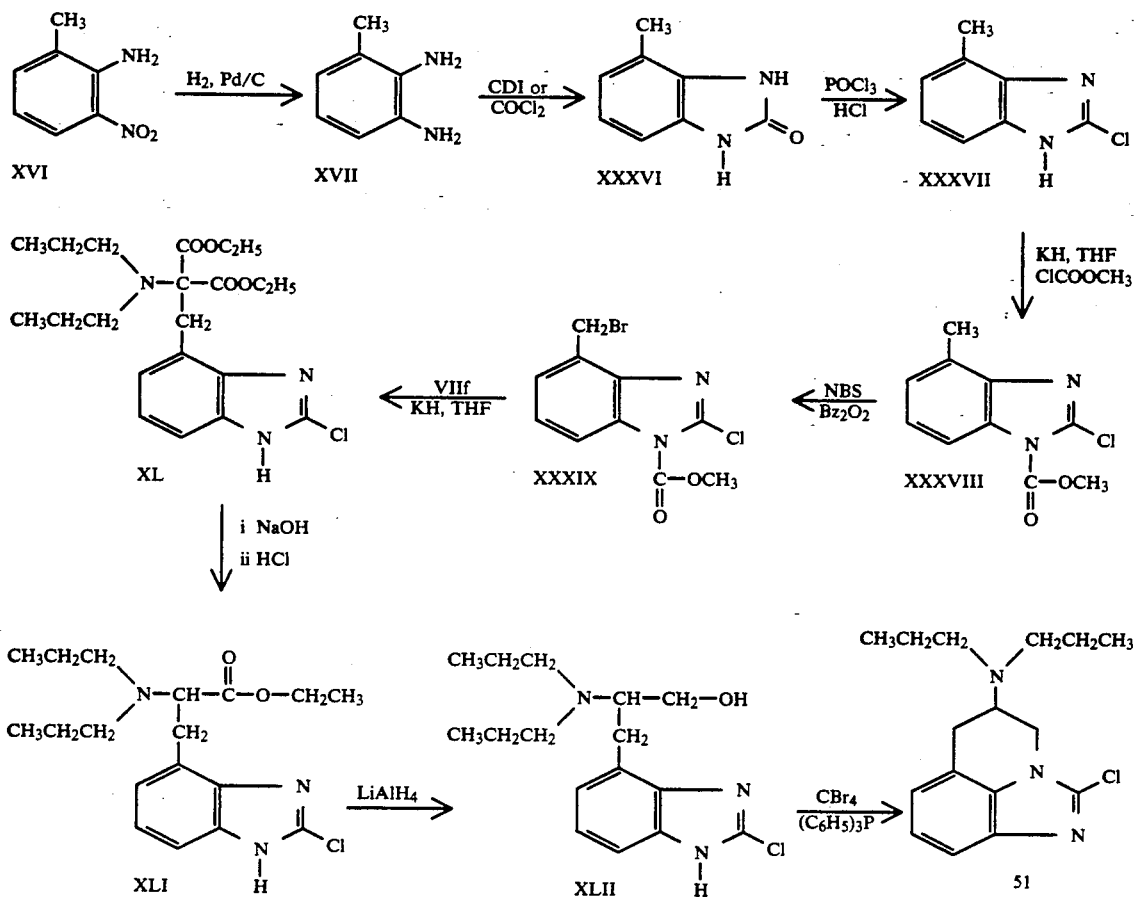
SCHEME 7
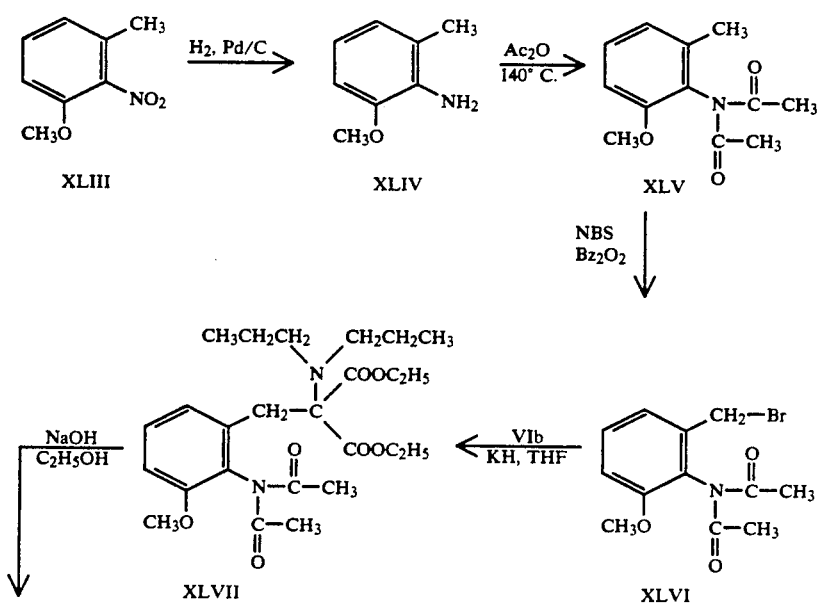

SCHEME 7
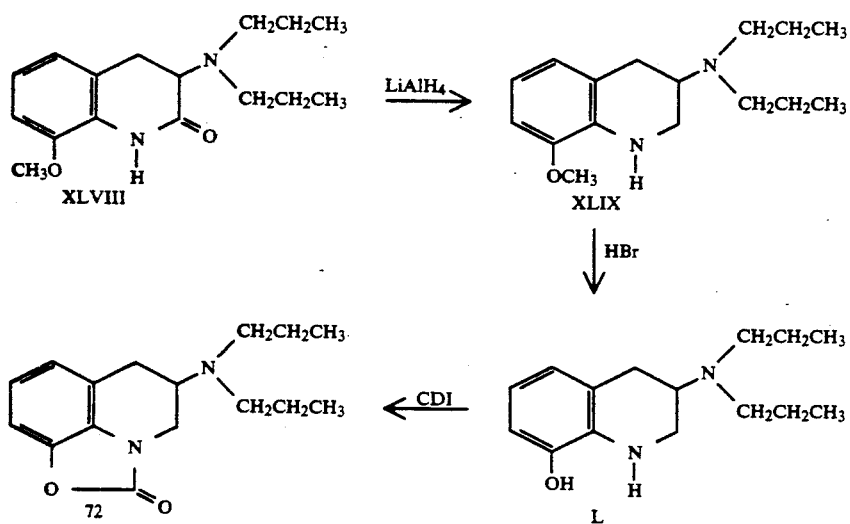
SCHEME 8
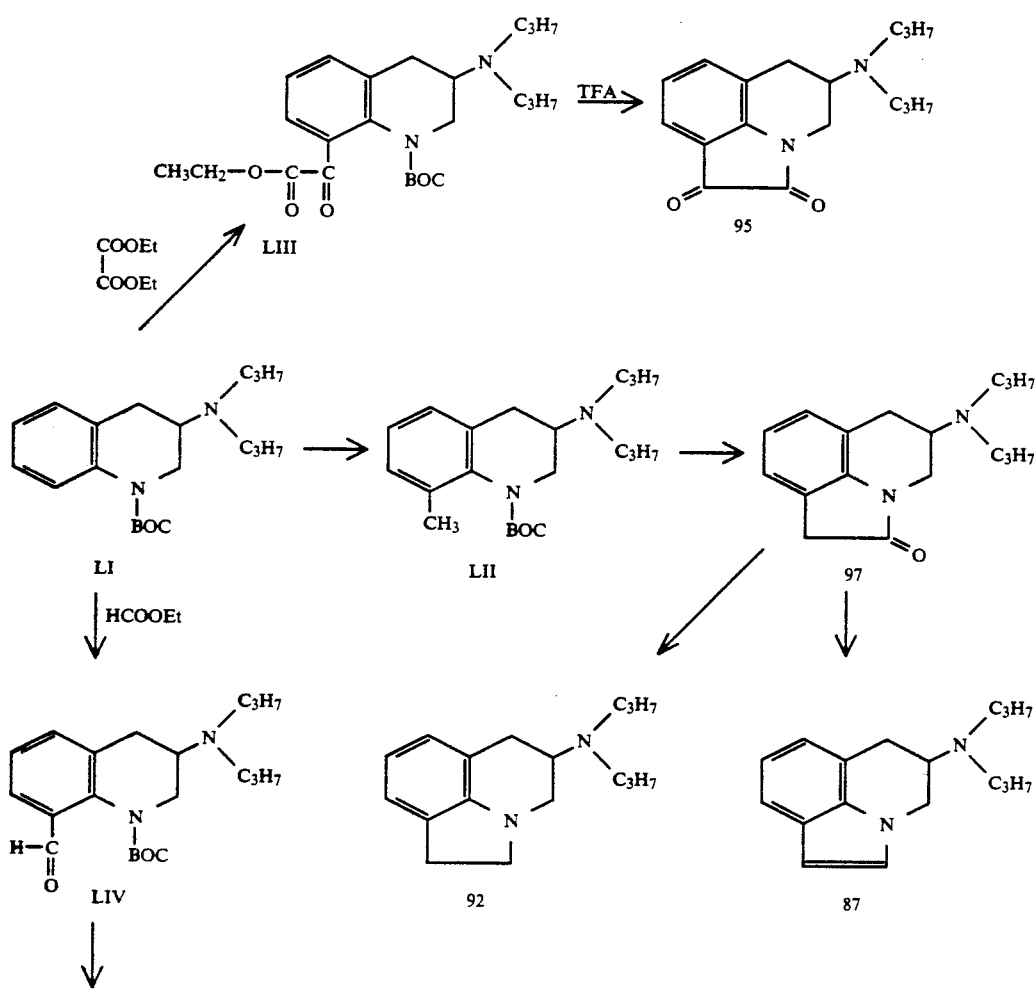

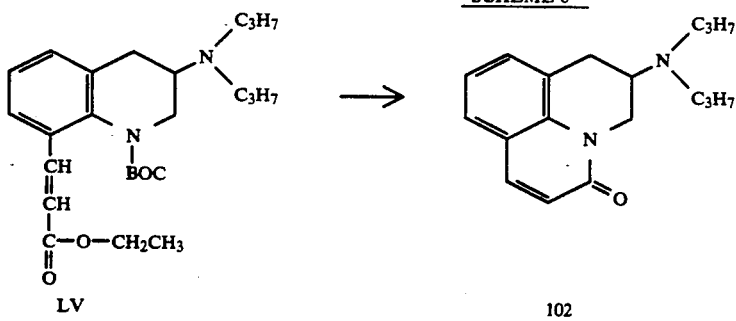

-continued
SCHEME 8

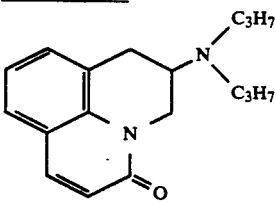

LV

102

We claim:
1. A compound of formula

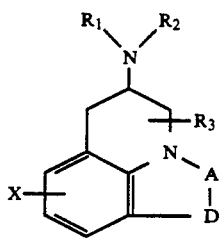

or a pharmaceutically-acceptable salt thereof, wherein $R_1$, $R_2$ and $R_3$ are independently H, $C_{1-6}$ alkyl, $C_{3-5}$ alkenyl, $C_{3-5}$ alkynyl, $C_{3-7}$ cycloalkyl, or $C_{4-10}$ cycloalkyl- or phenyl-substituted $C_{1-6}$ alkyl, or $NR_1R_2$ is pyrrolidine, piperidine, morpholine, 4-methyl piperazine or imidazole;

X is
 a) hydrogen,
 b) $C_{1-6}$ alkyl,
 c) halogen,
 d) hydroxy,
 e) $C_{1-6}$ alkoxy,
 f) cyano,
 g) carboxamide,
 h) carboxyl, or
 i) ($C_{1-6}$ alkoxy)carbonyl;

A is
 a) CH, $CH_2$, CH-halogen, $CHCH_3$, C=O, C=S, C—$SCH_3$, C=NH, C—$NH_2$, C—$NHCH_3$, C—$NHCOOCH_3$, or C—NHCN;
 b) $SO_2$, or
 c) N;
and
D is
 a) CH, $CH_2$, CH-halogen or C=O,
 b) O,
 c) N, NH or N—$CH_3$.

2. The compound of claim 1 wherein D is N or NH.
3. The compound of claim 2 wherein A is CH, $CH_2$, $CHCH_3$, C=O, C=S, C—$SCH_3$, C=NH, C—$NH_2$, C—$NHCH_3$, C—$NHCOOCH_3$, or C—NHCN.
4. The compound of claim 3 wherein A is CH or C=O.
5. The compound of claim 4 which is
 a) 5-(Dimethylamino)-5,6-dihydro-4H-imidazo(4,5,1-ij)quinolin-2(1H)-one hydrochloride b) 5-(Propylamino)-5,6-dihydro-4H-imidazo(4,5,1-ij)quinolin-2(1H)-one
 c) 5-(Dipropylamino)-5,6-dihydro-4H-imidazo(4,5,1-ij)quinolin-2(1H)-one
 d) (—)5-(Dipropylamino)-5,6-dihydro-4H-imidazo(4,5,1-ij)quinolin-2(1H)-one
 e) 5,6-Dihydro-N,N-dipropyl-4H-imidazo(4,5,1-ij)quinolin-5-amine
 f) 5,6-Dihydro-N-propyl-4H-imidazo(4,5,1-ij)quinoline-5-amine
 g) 5,6-Dihydro-5-(dipropylamino)-4H-imidazo(4,5,1-ij)quinolin-8-ol.

6. The compound of claim 1 wherein D is O and A is CH, $CH_2$, $CHCH_3$, C=O, C=S, C—$SCH_3$, C=NH, C—$NH_2$, C—$NHCH_3$, C—$NHCOOCH_3$, or C—NHCN.
7. The compound of claim 6 wherein A is C=O or C=S.
8. The compound of claim 7 which is
 a) 5-(Dipropylamino)-5,6-dihydro-2H,4H-oxazolo(5,4,3-ij)quinolin-2-one
 b) 5-(Propylamino)-5,6-dihydro-2H,4H-oxazolo(5,4,3-ij)quinolin-2-one
 c) 5-(Dimethylamino)-5,6-dihydro-2H,4H-oxazolo(5,4,3-ij)quinolin-2-one.

9. The compound of claim 1 wherein D is CH, $CH_2$, or C=O.
10. The compound of claim 9 which is
 a) 5,6-Dihydro-N,N-dipropyl-4H-pyrrolo(3,2,1-ij)quinolin-5-amine
 b) 5,6-Dihydro-N,N-dimethyl-4H-pyrrolo(3,2,1-ij)quinolin-5-amine
 c) 5,6-Dihydro-N,N-dipropyl-4H-pyrazolo(4,3,2-ij)quinolin-5-amine
 d) 5,6-Dihydro-N,N-dimethyl-4H-pyrazolo(4,3,2-ij)quinolin-5-amine
 e) 1,2,5,6-Tetrahydro-N,N-dipropyl-4H-pyrrolo(3,2,1-ij)quinolin-5-amine
 f) 1,2,5,6-Tetrahydro-N,N-dimethyl-4H-pyrrolo(3,2,1-ij)quinolin-5-amine
 g) 5-(Propylamino)-5,6-dihydro-4H-pyrrolo(3,2,1-ij)quinolin-2,3-dione
 h) 5-(Dipropylamino)-5,6-dihydro-4H-pyrrolo(3,2,1-ij)quinolin-2,3-dione
 i) 5-(Propylamino)-5,6-dihydro-4H-pyrrolo(3,2,1-ij)quinolin-2(1H)-one
 j) 5-(Dipropylamino)-5,6-dihydro-4H-pyrrolo(3,2,1-ij)quinolin-2(1H)-one 11. A method for treating central nervous system disorders in animal or human hosts in need thereof comprising the administration of a pharmaceutically effective amount of a compound of claim 1.

* * * * *